(12) United States Patent
Adachi et al.

(10) Patent No.: US 10,276,803 B2
(45) Date of Patent: Apr. 30, 2019

(54) ORGANIC LIGHT-EMITTING DEVICE, AND LIGHT-EMITTING MATERIAL AND COMPOUND USED THEREFOR

(71) Applicant: KYULUX, INC, Fukuoka-shi, Fukuoka (JP)

(72) Inventors: Chihaya Adachi, Fukuoka (JP); Hiroki Uoyama, Fukuoka (JP); Hiroko Nomura, Fukuoka (JP); Kenichi Goushi, Fukuoka (JP); Takuma Yasuda, Fukuoka (JP); Ryosuke Kondo, Fukuoka (JP); Katsuyuki Shizu, Fukuoka (JP); Hajime Nakanotani, Fukuoka (JP); Junichi Nishide, Fukuoka (JP)

(73) Assignee: KYULUX, INC., Fukuoka (JP)

( * ) Notice: Subject to any disclaimer, the term of this patent is extended or adjusted under 35 U.S.C. 154(b) by 0 days.

(21) Appl. No.: 15/293,889

(22) Filed: Oct. 14, 2016

(65) Prior Publication Data

US 2017/0256720 A1    Sep. 7, 2017

Related U.S. Application Data

(63) Continuation of application No. 14/391,228, filed as application No. PCT/JP2013/060582 on Apr. 8, 2013, now Pat. No. 9,502,668.

(30) Foreign Application Priority Data

Apr. 9, 2012 (JP) .................. 2012-088615
Aug. 3, 2012 (JP) .................. 2012-173277
Dec. 14, 2012 (JP) .................. 2012-274111

(51) Int. Cl.
| | |
|---|---|
| *C07D 209/88* | (2006.01) |
| *H01L 51/00* | (2006.01) |
| *C07D 209/86* | (2006.01) |
| *C09K 11/06* | (2006.01) |
| *C07D 209/18* | (2006.01) |
| *C07D 209/08* | (2006.01) |
| *H01L 51/50* | (2006.01) |

(52) U.S. Cl.
CPC ........ *H01L 51/0072* (2013.01); *C07D 209/08* (2013.01); *C07D 209/18* (2013.01); *C07D 209/86* (2013.01); *C09K 11/06* (2013.01); *H01L 51/50* (2013.01); *C09K 2211/1007* (2013.01); *C09K 2211/1029* (2013.01); *H01L 51/0054* (2013.01); *H01L 51/0067* (2013.01); *H01L 51/0074* (2013.01); *H01L 51/0085* (2013.01); *H01L 51/5012* (2013.01); *H01L 51/5016* (2013.01)

(58) Field of Classification Search
CPC ........... H01L 51/0072; H01L 51/0061; C07D 209/08; C07D 209/18; C07D 209/88; C07D 209/86; C09K 11/06
See application file for complete search history.

(56) References Cited

U.S. PATENT DOCUMENTS

| | | |
|---|---|---|
| 2000/7005725 | 3/2007 | Takiguchi et al. |
| 2009/0072727 A1 | 3/2009 | Takeda |

FOREIGN PATENT DOCUMENTS

| | | |
|---|---|---|
| EP | 2039737 | 3/2009 |
| JP | 2005-174917 | 6/2005 |
| JP | 2008-133225 | 6/2008 |
| JP | 2009-094486 | 4/2009 |
| JP | 2009-076834 | 9/2009 |
| KR | 10-2010-0123172 | 11/2010 |
| KR | 10-2011-0034977 | 4/2011 |
| KR | 10-2011-0034984 | 4/2011 |
| WO | 2008066196 | 6/2008 |

OTHER PUBLICATIONS

Office Action issued in corresponding Taiwanese Patent Application No. 102112555, dated Jun. 23, 2016, including English translation of relevant section.
European Search Report for Application No. 13775410 dated May 10, 2016.
Zhang et al. Journal of Photochemistry and Photobiology A: Chemistry 225(2011) 117-124.
Uoyama et al. Nature (London, UK) (2012), 492 (7428), 234-238.
International Preliminary Report on Patentability for international application No. PCT/JP2013/060582, dated Apr. 2013.
International Search Report for international application No. PCT/JP2013/060582, dated May 14, 2013.
Chinese Office Action dated Jun. 3, 2015, in corresponding Chinese application No. 201380019213.2.
Korean Office Action for corresponding Korean Patent Application No. 10-2014-7030961, dated Feb. 11, 2019, with English Machine Translation.
Herbich et al., Phosphorescent intramolecular charge transfer triplet states, Chemical Physics Letters, 262:633-642 (1996).

*Primary Examiner* — Nyeemah A Grazier
(74) *Attorney, Agent, or Firm* — Browdy and Neimark, PLLC

(57) ABSTRACT

An organic light-emitting device having a light-emitting layer containing a compound represented by the general formula below has a high light emission efficiency. In the general formula, at least one of $R^1$ to $R^5$ represents a cyano group, at least one of $R^1$ to $R^5$ represents a 9-carbazolyl group, a 1,2,3,4-tetrahydro-9-carbazolyl group, a 1-indolyl group or a diarylamino group, and the balance of $R^1$ to $R^5$ represents a hydrogen atom or a substituent.

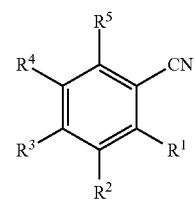

19 Claims, 10 Drawing Sheets

ORGANIC LIGHT-EMITTING DEVICE, AND LIGHT-EMITTING MATERIAL AND COMPOUND USED THEREFOR

TECHNICAL FIELD

The present invention relates to an organic light-emitting device having a high light emission efficiency. The invention also relates to a light-emitting material and a compound used therefor.

BACKGROUND ART

An organic light-emitting device, such as an organic electroluminescent device (organic EL device), has been actively studied for enhancing the light emission efficiency thereof. In particular, various studies for enhancing the light-emitting efficiency have been made by newly developing and combining an electron transporting material, a hole transporting material, a light-emitting material and the like constituting an organic electroluminescent device. There are studies relating to an organic electroluminescent device utilizing a compound containing a carbazole structure and an indole structure, which are found among them, and some proposals have been made hitherto.

For example, PTL 1 describes the use of an organic compound having a carbazole structure and an indole structure represented by the following general formula, as a host material of a light-emitting layer of an organic light-emitting device. In the following general formula, m and n each represent an integer of from 1 to 5, provided that the sum of m and n is an integer of from 2 to 6; X represents an organic group having a valency of (m+n) which may have a substituent; and $R_1$ to $R_{14}$ represent a hydrogen atom, a halogen atom, an alkyl group, an aryl group or a heterocyclic group.

[Chem. 1]

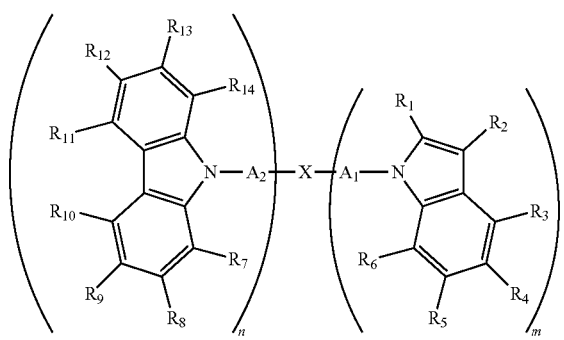

PTL 2 describes the use of a compound having two or more carbazole structures, as a host material of a light-emitting layer of an organic light-emitting device. PTL 3 describes the use of a compound having two or more indole structures, as a host material of a light-emitting layer of an organic light-emitting device.

CITATION LIST

Patent Literatures

PTL 1: JP-A-2005-174917
PTL 2: JP-A-2009-94486
PTL 3: JP-A-2009-76834

SUMMARY OF INVENTION

Technical Problem

As described above, a compound containing a carbazole structure and/or an indole structure has been variously studied, and some proposals relating to application thereof to an organic electroluminescent device have been made. In most of the organic electroluminescent devices having been proposed, however, the proposals therein are the use of a compound containing a carbazole structure and/or an indole structure as a host material of a light-emitting layer. Furthermore, the light emission efficiency thereof is not necessarily high. Moreover, it may not be said that all the compounds containing a carbazole structure and/or an indole structure have been comprehensively studied. In particular, the usefulness of a compound containing a carbazole structure and/or an indole structure as a light-emitting material and the usefulness of a compound containing a carbazole structure or an indole structure and further containing plural cyano groups have almost not been studied. According to the studies having been made, a clear relationship has not yet been found between the chemical structure of the compound containing a carbazole structure and/or an indole structure and the usefulness of the compound as a light-emitting material, and it is the current situation that it is difficult to expect the usefulness as a light-emitting compound based on the chemical structure. The present inventors have considered these problems and have made investigations for evaluating the usefulness of a cyanobenzene derivative having a carbazole structure, an indole structure and the like, as a light-emitting material of an organic light-emitting device. The inventors also have made investigations for providing a general formula of a compound that is useful as a light-emitting material, thereby generalizing a constitution of an organic light-emitting device having a high light emission efficiency.

Solution to Problem

As a result of earnest investigations for achieving the objects, the inventors have clarified that a particular cyanobenzene derivative containing a carbazole structure, an indole structure and the like is extremely useful as a light-emitting material of an organic electroluminescent device. In particular, the inventors have found a compound that is useful as a delayed fluorescent material in cyanobenzene derivatives containing a carbazole structure, an indole structure and the like, and have clarified that an organic light-emitting device having a high light emission efficiency may be provided inexpensively. Based on the knowledge, the inventors have provided the following inventions as measures for solving the problems.

(1) A light-emitting material containing a compound represented by the following general formula (1):

[Chem. 2]

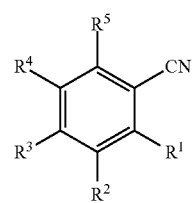

General Formula (1)

wherein in the general formula (1), at least one of $R^1$ to $R^5$ represents a cyano group, at least one of $R^1$ to $R^5$ represents a group represented by the following general formula (11), and the balance of $R^1$ to $R^5$ represents a hydrogen atom or a substituent;

[Chem. 3]

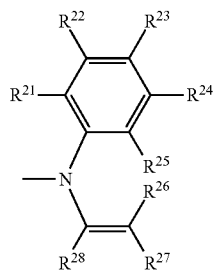

General Formula (11)

wherein in the general formula (11), $R^{21}$ to $R^{28}$ each independently represent a hydrogen atom or a substituent, provided that at least one of the following requirements (A) and (B) is satisfied:
(A) $R^{25}$ and $R^{26}$ jointly form a single bond, and
(B) $R^{27}$ and $R^{28}$ jointly form an atomic group that is required for forming a substituted or unsubstituted benzene ring.

(2) The light-emitting material according to the item, (1), which emits delayed fluorescent light.

(3) The light-emitting material according to the item (1) or (2), wherein at least one of $R^1$ to $R^5$ represents a substituted or unsubstituted 9-carbazolyl group, a substituted or unsubstituted 1,2,3,4-tetrahydro-9-carbazolyl group, a substituted or unsubstituted 1-indolyl group or a substituted or unsubstituted diarylamino group.

(4) The light-emitting material according to the item (1) or (2), wherein at least two of $R^1$ to $R^5$ represent a substituted or unsubstituted 9-carbazolyl group, a substituted or unsubstituted 1,2,3,4-tetrahydro-9-carbazolyl group, a substituted or unsubstituted 1-indolyl group or a substituted or unsubstituted diarylamino group.

(5) The light-emitting material according to the item (1) or (2), wherein at least one of $R^1$ to $R^5$ represents a cyano group, and the balance of $R^1$ to $R^5$ each independently represents any of a hydroxy group, a halogen atom, a substituted or unsubstituted 9-carbazolyl group, a substituted or unsubstituted 1,2,3,4-tetrahydro-9-carbazolyl group, a substituted or unsubstituted 1-indolyl group or a substituted or unsubstituted diarylamino group.

(6) The light-emitting material according to the item (1) or (2), wherein at least one of $R^1$ to $R^5$ represents a cyano group, and the balance of $R^1$ to $R^5$ each independently represents any of a substituted or unsubstituted 9-carbazolyl group, a substituted or unsubstituted 1,2,3,4-tetrahydro-9-carbazolyl group, a substituted or unsubstituted 1-indolyl group or a substituted or unsubstituted diarylamino group.

(7) The light-emitting material according to the item (1) or (2), wherein at least one of $R^1$ to $R^5$ represents a cyano group, and the balance of $R^1$ to $R^5$ each represents a substituted or unsubstituted 9-carbazolyl group.

(8) The light-emitting material according to the item (1) or (2), wherein at least one of $R^1$ to $R^5$ represents a hydroxy group, at least one of $R^1$ to $R^5$ represents a cyano group, and the balance of $R^1$ to $R^5$ each represent a substituted ox unsubstituted 9-carbazolyl group.

(9) The light-emitting material according to any one of the items (1) to (8), wherein at least one of $R^1$ to $R^5$ represents a group represented by any of the following general formulae (12) to (15):

[Chem. 4]

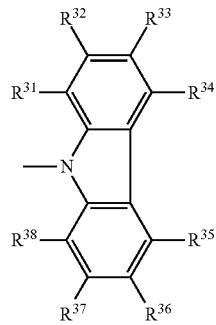

General Formula (12)

wherein in the general formula (12), $R^{31}$ to $R^{38}$ each independently represent a hydrogen atom or a substituent;

[Chem. 5]

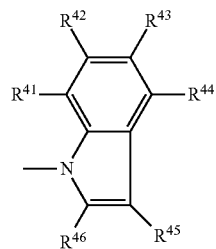

General Formula (13)

wherein in the general formula (13), $R^{41}$ to $R^{46}$ each independently represent a hydrogen atom or a substituent;

[Chem. 6]

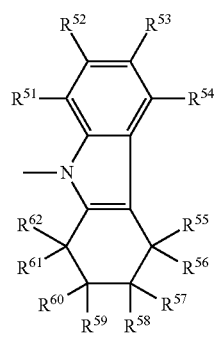

General Formula (14)

wherein in the general formula (14), $R^{51}$ to $R^{62}$ each independently represent a hydrogen atom or a substituent;

[Chem. 7]

General Formula (15)

wherein in the general formula (15), $R^{71}$ to $R^{80}$ each independently represent a hydrogen atom or a substituent.

(10) The light-emitting material according to any one of the items (1) to (9), which contains a compound represented by the following general formula (2):

[Chem. 8]

General Formula (2)

wherein in the general formula (2), at least one of $R^{11}$, $R^{12}$, $R^{14}$ and $R^{15}$ represents a cyano group, at least three of $R^{11}$ to $R^{15}$ each represent a substituted or unsubstituted 9-carbazolyl group, a substituted or unsubstituted 1,2,3,4-tetrahydro-9-carbazolyl group, a substituted or unsubstituted 1-indolyl group or a substituted or unsubstituted diarylamino group, and the balance of $R^{11}$ to $R^{15}$ represents a hydroxyl group.

(11) The light-emitting material according to any one of the items (1) to (9), which contains a compound represented by the following general formula (3):

[Chem. 9]

General Formula (3)

wherein in the general formula (3), one of $R^{81}$ to $R^{85}$ represents a cyano group, two of $R^{81}$ to $R^{85}$ each represent a substituted or unsubstituted 9-carbazolyl group, and the other two thereof each represent a hydrogen atom.

(12) A compound represented by the general formula (2).

(13) An organic light-emitting device containing a substrate having thereon a light-emitting layer containing the light-emitting material according to any one of the items (1) to (11).

(14) The organic light-emitting device according to the item (13), which emits delayed fluorescent light.

(15) The organic Light-emitting device according to the item (13) or (14), which is an organic electroluminescent device.

(16) A delayed fluorescent emitter having a structure represented by the general formula (1).

Advantageous Effects of Invention

The organic light-emitting device of the invention has such a feature that the device has a high light emission efficiency. The delayed fluorescent material of the invention has such a feature that when the material is used in a light-emitting layer of an organic light-emitting device, the organic light-emitting device emits delayed fluorescent light with a light emission efficiency that is drastically enhanced. The compound of the invention is extremely useful as a light-emitting material for the organic light-emitting device.

DESCRIPTION OF EMBODIMENTS

Figure 1:
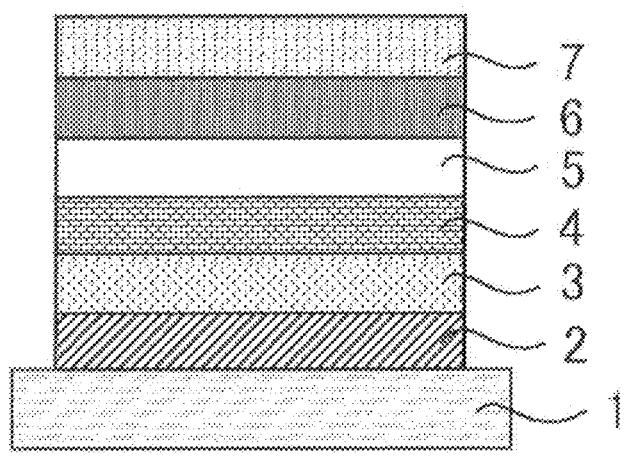
FIG. 1 is a schematic cross sectional view showing an example of a layer structure of an organic electroluminescent device.

The contents of the invention will be described in detail below. The constitutional elements may be described below with reference to representative embodiments and specific examples of the invention, but the invention is not limited to the embodiments and the examples. In the present specification, a numerical range expressed by "from X to Y" means a range including the numerals X and Y as the lower limit and the upper limit, respectively.

Compound Represented by General Formula (1)

The light-emitting material of the invention contains the compound represented by the following general formula (1). The organic light-emitting device of the invention contains the compound represented by the following general formula (1) as a light-emitting material of a light-emitting layer. The compound represented by the general formula (1) will be described.

[Chem. 10]

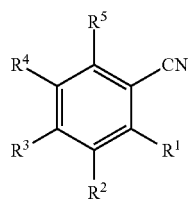

General Formula (1)

In the general formula (1), at least one of $R^1$ to $R^5$ represents a cyano group. In the case where any one thereof is a cyano group, the cyano group may be any of $R^1$ to $R^3$. In the case where any two thereof each are a cyano group, examples thereof include a combination of $R^1$ and $R^3$, and a combination of $R^2$ and $R^4$. In the case where any three thereof each are a cyano group, examples thereof include a combination of $R^1$, $R^3$ and $R^4$.

In the general formula (1), at least one of $R^1$ to $R^5$ represents a group represented by the following general formula (11). In the case where two or more thereof represent a group represented by the general formula (11), the groups may be the same as or different from each other, and are preferably the same as each other.

[Chem. 11]

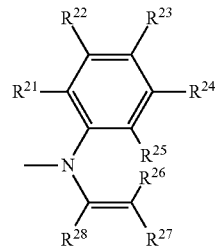

General Formula (11)

In the general formula (12), $R^{21}$ to $R^{28}$ each independently represent a hydrogen atom or a substituent, provided that at least one of the following requirements (A) and (B) is satisfied, and both the requirements (A) and (B) are preferably satisfied:

(A) $R^{25}$ and $R^{26}$ jointly form a single bond, and (B) $R^{27}$ and $R^{28}$ jointly form an atomic group that is required for forming a substituted or unsubstituted benzene ring.

The group represented by the general formula (11) is preferably a substituted or unsubstituted 9-carbazoyl group, a substituted or unsubstituted 1,2,3,4-tetrahydro-9-carbazolyl group, a substituted or unsubstituted 1-indolyl group or a substituted or unsubstituted diarylamino group. Accordingly, it is preferred that at least one of $R^1$ to $R^5$ in the general formula (1) represents a substituted or unsubstituted 9-carbazolyl group, a substituted or unsubstituted 1,2,3,4-tetrahydro-9-carbazolyl group, a substituted or unsubstituted 1-indolyl group or a substituted or unsubstituted diarylamino group. It is more preferred that at least two of $R^1$ to $R^5$ in the general formula (1) represent a substituted or unsubstituted 9-carbazolyl group, a substituted or unsubstituted 1,2,3,4-tetrahydro-9-carbazolyl group, a substituted or unsubstituted 1-indolyl group or a substituted or unsubstituted diarylamino group.

Preferred examples of the group represented by the general formula (11) include groups having a structure represented by any of the following general formulae (12) to (15), and more preferred examples thereof include groups having a structure represented by the following general formula (12).

[Chem. 12]

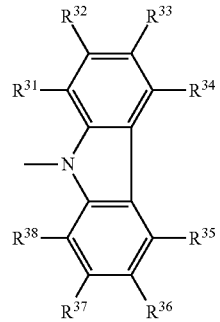

General Formula (12)

-continued

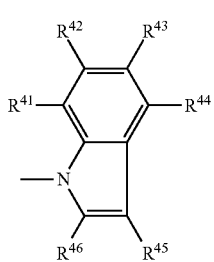

General Formula (13)

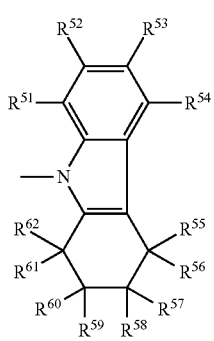

General Formula (14)

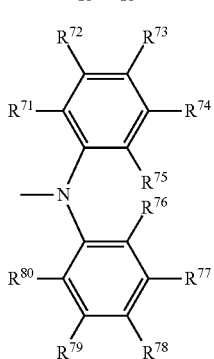

General Formula (15)

In the general formulae (12) to (15), $R^{31}$ to $R^{38}$, $R^{41}$ to $R^{46}$, $R^{51}$ to $R^{52}$, and $R^{71}$ to $R^{80}$ each independently represent a hydrogen atom or a substituent. In the case where the group represented by the general formulae (12) to (15) has a substituent, the substitution position and the number of the substituent are not particularly limited. The number of substituent of the groups is preferably from 0 to 6, more preferably from 0 to 4, and, for example, preferably from 0 to 2. In the case where the groups have plural substituents, the substituents may be the same as or different from each other, and are preferably the same as each other.

In the case where the group represented by the general formula (12) has a substituent, any of $R^{32}$ to $R^{37}$ is preferably a substituent. Preferred examples of the case include the case where $R^{32}$ and $R^{37}$ are substituents, the case where $R^{33}$ and $R^{36}$ are substituents, and the case where $R^{34}$ and $R^{35}$ are substituents.

In the case where the group represented by the general formula (13) has a substituent, any of $R^{42}$ to $R^{45}$ is preferably a substituent. Preferred examples of the case include the case where $R^{42}$ is a substituent, and the case where $R^{43}$ is a substituent.

In the case where the group represented by the general formula (14) has a substituent, any of $R^{52}$ to $R^{60}$ is preferably a substituent. Preferred examples of the case include the case where any of $R^{52}$ to $R^{54}$ is a substituent, and the case where any of $R^{55}$ to $R^{60}$ is a substituent.

In the case where the group represented by the general formula (15) has a substituent, any of $R^{72}$ to $R^{74}$ and $R^{77}$ to $R^{79}$ is preferably a substituent. Preferred examples of the case include the case where $R^{72}$ and $R^{79}$ are substituents, the case where $R^{73}$ and $R^{78}$ are substituents, the case where $R^{74}$ and $R^{77}$ are substituents, and the case where $R^{72}$, $R^{74}$, $R^{77}$ and $R^{79}$ are substituents. More preferred examples of the case include the case where $R^{74}$ and $R^{77}$ are substituents, and the case where $R^{72}$, $R^{74}$, $R^{77}$ and $R^{79}$ are substituents. The substituents herein each are particularly preferably a substituted or unsubstituted alkyl group having from 1 to 20 carbon atoms or a substituted or unsubstituted aryl group having from 6 to 40 carbon atoms, and further preferably an unsubstituted alkyl group having from 1 to 6 carbon atoms, an unsubstituted aryl group having from 6 to 10 carbon atoms, or an aryl group having from 6 to 10 carbon atoms substituted with an aryl group having from 6 to 10 carbon atoms.

Examples of the substituent that may be $R^{21}$ to $R^{28}$ in the general formula (11), $R^{31}$ to $R^{38}$ in the general formula (12), $R^{41}$ to $R^{46}$ in the general formula (13), $R^{51}$ to $R^{62}$ in the general formula (14), and $R^{71}$ to $R^{80}$ in the general formula (15) include a hydroxy group, a halogen atom, a cyano group, an alkyl group having from 1 to 20 carbon atoms, an alkoxy group having from 1 to 20 carbon atoms, an alkylthio group having from 1 to 20 carbon atoms, an alkyl-substituted amino group having from 1 to 20 carbon atoms, an acyl group having from 2 to 20 carbon atoms, an aryl group having from 6 to 40 carbon atoms, a heteroaryl group having from 3 to 40 carbon atoms, a diarylamino group having from 12 to 40 carbon atoms, a substituted or unsubstituted carbazolyl group having from 12 to 40 carbon atoms, an alkenyl group having from 2 to 10 carbon atoms, an alkynyl group having from 2 to 10 carbon atoms, an alkoxycarbonyl group having from 2 to 10 carbon atoms, an alkylsulfonyl group having from 1 to 10 carbon atoms, a haloalkyl group having from 1 to 10 carbon atoms, an amide group, an alkylamide group having from 2 to 10 carbon atoms, a trialkylsilyl group having from 3 to 20 carbon atoms, a trialkylsilylalkyl group having from 4 to 20 carbon atoms, a trialkylsilylalkenyl group having from 5 to 20 carbon atoms, a trialkylsilylalkynyl group having from 5 to 20 carbon atoms, and a nitro group. In these specific examples, the groups that may be further substituted with a substituent may be substituted. More preferred examples of the substituent include a halogen atom, a cyano group, a substituted or unsubstituted alkyl group having from 1 to 20 carbon atoms, an alkoxy group having from 1 to 20 carbon atoms, a substituted or unsubstituted aryl group having from 6 to 40 carbon atoms, a substituted or unsubstituted heteroaryl group having from 3 to 40 carbon atoms, a substituted or unsubstituted diarylamino group having from 12 to 40 carbon atoms, and a substituted or unsubstituted carbazolyl group having from 12 to 40 carbon atoms. Further preferred examples of the substituent include a fluorine atom, a chlorine atom, a cyano group, a substituted or unsubstituted alkyl group having from 1 to 10 carbon atoms, a substituted or unsubstituted alkoxy group having from 1 to 10 carbon atoms, a substituted or unsubstituted dialkylamino group having from 1 to 10 carbon atoms, a substituted or unsubstituted aryl group having from 6 to 15 carbon atoms, and a substituted or unsubstituted heteroaryl group having from 3 to 12 carbon atoms.

The alkyl group referred in the description may be any of linear, branched or cyclic and more preferably has from 1 to 6 carbon atoms, and specific examples thereof include a methyl group, an ethyl group, a propyl group, a butyl group, a t-butyl group, a pentyl group, a hexyl group and an isopropyl group. The aryl group may be a monocyclic ring or a fused ring, and specific examples thereof include a phenyl group and a naphthyl group. The alkoxy group may be any of linear, branched or cyclic and more preferably has from 1 to 6 carbon atoms, and specific examples thereof include a methoxy group, an ethoxy group, a propoxy group, a butoxy group, a t-butoxy group, a pentyloxy group, a hexyloxy group and an isopropoxy group. The two alkyl groups of the dialkylamino group may be the same as or different from each other, and are preferably the same as each other. The two alkyl groups of the dialkylamino group each may independently be any of linear, branched or cyclic and each independently preferably have from 1 to 6 carbon atoms, and specific examples thereof include a methyl group, an ethyl group, a propyl group, a butyl group, a pentyl group, a hexyl group and an isopropyl group. The aryl group may be a monocyclic ring or a fused ring, and specific examples thereof include a phenyl group and a naphthyl group. The heteroaryl group may also be a monocyclic ring or a fused ring, and specific examples thereof include a pyridyl group, a pyridazyl group, a pyrimidyl group, a triazyl group, a triazolyl group and a benzotriazolyl group. The heteroaryl group may be a group that is bonded through the heteroatom or a group that is bonded through the carbon atom constituting the heteroaryl ring.

In the general formula (1), in the case where any one of $R^1$ to $R^5$ represents a group represented by the general formula (11), the group represented by the general formula (11) may be any of $R^1$ to $R^3$. In the case where two thereof each are a group represented by the general formula (11), examples of the case include a combination of $R^1$ and $R^3$, and a combination of $R^2$ and $R^4$. In the case where three thereof each are a group represented by the general formula (11), examples of the case include a combination of $R^1$, $R^3$ and $R^4$.

Any one of the two o-positions of the benzene ring with respect to the group represented by the general formula (11) bonded thereto is preferably a cyano group. Both the two o-positions may be cyano groups. In the case where two or more groups represented by the general formula (11) are bonded to the benzene ring, at least two thereof preferably satisfy the requirement that any one of the two o-positions of the benzene ring with respect to the group represented by the general formula (11) bonded thereto is a cyano group.

In the general formula (1), at least one of $R^1$ to $R^5$ represents a cyano group, at least one of $R^1$ to $R^5$ represents a group represented by the following general formula (11), and the balance of $R^1$ to $R^5$ represents a hydrogen atom or a substituent.

Examples of the preferred substituent that may be $R^1$ to $R^5$ include a hydroxy group, a halogen atom, an alkyl group having from 1 to 20 carbon atoms, an alkoxy group having from 1 to 20 carbon atoms, an alkylthio group having from 1 to 20 carbon atoms, an alkyl-substituted amino group having from 1 to 20 carbon atoms, an acyl group having from 2 to 20 carbon atoms, an aryl group having from 6 to 40 carbon atoms, a heteroaryl group having from 3 to 40 carbon atoms, an alkenyl group having from 2 to 10 carbon atoms, an alkynyl group having from 2 to 10 carbon atoms, an alkoxycarbonyl group having from 2 to 10 carbon atoms, an alkylsulfonyl group having from 1 to 10 carbon atoms, an amide group, an alkylamide group having from 2 to 10 carbon atoms, a trialkylsilyl group having from 3 to 20 carbon atoms, a trialkylsilylalkyl group having from 4 to 20 carbon atoms, a trialkylsilylalkenyl group having from 5 to 20 carbon atoms, a trialkylsilylalkynyl group having from 5 to 20 carbon atoms, and a nitro group. In these specific examples, the groups that may be further substituted with a substituent may be substituted. More preferred examples of the substituent include a hydroxy group, a halogen atom, a substituted or unsubstituted alkyl group having from 1 to 20 carbon atoms, an alkoxy group having from 1 to 20 carbon atoms, a substituted or unsubstituted dialkylamino group having from 1 to 20 carbon atoms, a substituted or unsubstituted aryl group having from 6 to 40 carbon atoms, and a substituted or unsubstituted heteroaryl group having from 3 to 40 carbon atoms. Further preferred examples of the substituent include a hydroxy group, a fluorine atom, a chlorine atom, a substituted or unsubstituted alkyl group having from 1 to 10 carbon atoms, a substituted or unsubstituted alkoxy group having from 1 to 10 carbon atoms, a substituted or unsubstituted dialkylamino group having from 1 to 10 carbon atoms, a substituted or unsubstituted aryl group having from 6 to 15 carbon atoms, and a substituted or unsubstituted heteroaryl group having from 3 to 12 carbon atoms. Still further preferred examples of the substituent include a hydroxy group, a fluorine atom and a chlorine atom.

In the general formula (1), the number of hydrogen atom of $R^1$ to $R^5$ is preferably 3 or less, more preferably 2 or less, further preferably 1 or less, and still further preferably 0.

Preferred examples of the combination of $R^1$ to $R^5$ in the general formula (1) include the case where at least one of $R^1$ to $R^5$ represents a cyano group, and the balance of $R^1$ to $R^5$ each independently represents a hydroxy group, a halogen atom, a substituted or unsubstituted 9-carbazolyl group, a substituted or unsubstituted 1,2,3,4-tetrahydro-9-carbazolyl group, a substituted or unsubstituted 1-indolyl group or a substituted or unsubstituted diarylamino group. Preferred examples of the combination also include the case where at least one of $R^1$ to $R^5$ represents a cyano group, and the balance of $R^1$ to $R^5$ each independently represents a substituted or unsubstituted 9-carbazolyl group, a substituted or unsubstituted 1,2,3,4-tetrahydro-9-carbazolyl group, a substituted or unsubstituted 1-indolyl group or a substituted or unsubstituted diarylamino group. Preferred examples of the combination further include the case where at least one of $R^1$ to $R^5$ in the general formula (1) represents a cyano group, and the balance of $R^1$ to $R^5$ each independently represents any of a hydroxy group, a halogen atom or a substituted or unsubstituted 9-carbazolyl group. Preferred examples of the combination still further include the case where at least one of $R^1$ to $R^5$ in the general formula (1) represents a cyano group, and the balance of $R^1$ to $R^5$ each represents a substituted or unsubstituted 9-carbazolyl group. Preferred examples of the combination still further include the case where at least one of $R^1$ to $R^5$ in the general formula (1) represents a cyano group, at least one of $R^1$ to $R^5$ represents a hydroxy group, and the balance of $R^1$ to $R^5$ each represents a substituted or unsubstituted 9-carbazolyl group. Preferred examples of the combination still further include the case where at least one of $R^1$ to $R^5$ in the general formula (1) represents a cyano group, at least one of $R^1$ to $R^5$ represents a halogen atom, and the balance of $R^1$ to $R^5$ each represents a substituted or unsubstituted 9-carbazolyl group.

Specific examples of the compound represented by the general formula (1) will be shown below, but the compound represented by the general formula (1) capable of being used in the invention is not construed as being limited to the specific examples. In the following specific examples of the compound, in the case where two or more groups represented by any of the general formulae (12) to (15) are present in the molecule, all the groups are the same structure as each other. For example, in the compound 1 in Table 1, $R^1$, $R^2$, $R^4$ and $R^5$ in the general formula (1) are the groups represented by the general formula (12), and all the groups are unsubstituted 9-carbazolyl groups.

TABLE 1

| Compound No. | General Formula (1) | | | | | General Formula (12) | | | |
|---|---|---|---|---|---|---|---|---|---|
| | $R^1$ | $R^2$ | $R^3$ | $R^4$ | $R^5$ | $R^{31}, R^{38}$ | $R^{32}, R^{37}$ | $R^{33}, R^{36}$ | $R^{34}, R^{35}$ |
| 1 | General Formula (12) | General Formula (12) | CN | General Formula (12) | General Formula (12) | H | H | H | H |
| 2 | General Formula (12) | General Formula (12) | CN | General Formula (12) | General Formula (12) | H | $CH_3$ | H | H |
| 3 | General Formula (12) | General Formula (12) | CN | General Formula (12) | General Formula (12) | H | $CH_3O$ | H | H |
| 4 | General Formula (12) | General Formula (12) | CN | General Formula (12) | General Formula (12) | H | H | $CH_3$ | H |
| 5 | General Formula (12) | General Formula (12) | CN | General Formula (12) | General Formula (12) | H | H | $CH_3O$ | H |
| 6 | General Formula (12) | General Formula (12) | CN | General Formula (12) | General Formula (12) | H | H | $t\text{-}C_4H_9$ | H |
| 7 | General Formula (12) | General Formula (12) | CN | General Formula (12) | General Formula (12) | H | H | Cl | H |
| 8 | General Formula (12) | General Formula (12) | CN | General Formula (12) | General Formula (12) | H | H | F | H |
| 9 | General Formula (12) | General Formula (12) | CN | General Formula (12) | General Formula (12) | H | H | H | $CH_3$ |
| 10 | General Formula (12) | General Formula (12) | CN | General Formula (12) | General Formula (12) | H | H | H | $CH_3O$ |
| 11 | General Formula (12) | General Formula (12) | CN | General Formula (12) | H | H | H | H | H |
| 12 | General Formula (12) | General Formula (12) | CN | General Formula (12) | H | H | $CH_3$ | H | H |
| 13 | General Formula (12) | General Formula (12) | CN | General Formula (12) | H | H | $CH_3O$ | H | H |
| 14 | General Formula (12) | General Formula (12) | CN | General Formula (12) | H | H | H | $CH_3$ | H |
| 15 | General Formula (12) | General Formula (12) | CN | General Formula (12) | H | H | H | $CH_3O$ | H |
| 16 | General Formula (12) | General Formula (12) | CN | General Formula (12) | H | H | H | $t\text{-}C_4H_9$ | H |
| 17 | General Formula (12) | General Formula (12) | CN | General Formula (12) | H | H | H | Cl | H |
| 18 | General Formula (12) | General Formula (12) | CN | General Formula (12) | H | H | H | F | H |
| 19 | General Formula (12) | General Formula (12) | CN | General Formula (12) | H | H | H | H | $CH_3$ |
| 20 | General Formula (12) | General Formula (12) | CN | General Formula (12) | H | H | H | H | $CH_3O$ |
| 21 | General Formula (12) | General Formula (12) | CN | H | H | H | H | H | H |
| 22 | General Formula (12) | General Formula (12) | CN | H | H | H | $CH_3$ | H | H |
| 23 | General Formula (12) | General Formula (12) | CN | H | H | H | $CH_3O$ | H | H |
| 24 | General Formula (12) | General Formula (12) | CN | H | H | H | H | $CH_3$ | H |

TABLE 1-continued

| Compound No. | General Formula (1) | | | | | General Formula (12) | | | |
|---|---|---|---|---|---|---|---|---|---|
| | $R^1$ | $R^2$ | $R^3$ | $R^4$ | $R^5$ | $R^{31}, R^{38}$ | $R^{32}, R^{37}$ | $R^{33}, R^{36}$ | $R^{34}, R^{35}$ |
| 25 | General Formula (12) | General Formula (12) | CN | H | H | H | H | $CH_3O$ | H |
| 26 | General Formula (12) | General Formula (12) | CN | H | H | H | H | $t\text{-}C_4H_9$ | H |
| 27 | General Formula (12) | General Formula (12) | CN | H | H | H | H | Cl | H |
| 28 | General Formula (12) | General Formula (12) | CN | H | H | H | H | F | H |
| 29 | General Formula (12) | General Formula (12) | CN | H | H | H | H | H | $CH_3$ |
| 30 | General Formula (12) | General Formula (12) | CN | H | H | H | H | H | $CH_3O$ |
| 31 | General Formula (12) | H | CN | General Formula (12) | H | H | H | H | H |
| 32 | General Formula (12) | H | CN | General Formula (12) | H | H | $CH_3$ | H | H |
| 33 | General Formula (12) | H | CN | General Formula (12) | H | H | $CH_3O$ | H | H |
| 34 | General Formula (12) | H | CN | General Formula (12) | H | H | H | $CH_3$ | H |
| 35 | General Formula (12) | H | CN | General Formula (12) | H | H | H | $CH_3O$ | H |
| 36 | General Formula (12) | H | CN | General Formula (12) | H | H | H | $t\text{-}C_4H_9$ | H |
| 37 | General Formula (12) | H | CN | General Formula (12) | H | H | H | Cl | H |
| 38 | General Formula (12) | H | CN | General Formula (12) | H | H | H | F | H |
| 39 | General Formula (12) | H | CN | General Formula (12) | H | H | H | H | $CH_3$ |
| 40 | General Formula (12) | H | CN | General Formula (12) | H | H | H | H | $CH_3O$ |
| 41 | General Formula (12) | H | CN | H | General Formula (12) | H | H | H | H |
| 42 | General Formula (12) | H | CN | H | General Formula (12) | H | $CH_3$ | H | H |
| 43 | General Formula (12) | H | CN | H | General Formula (12) | H | $CH_3O$ | H | H |
| 44 | General Formula (12) | H | CN | H | General Formula (12) | H | H | $CH_3$ | H |
| 45 | General Formula (12) | H | CN | H | General Formula (12) | H | H | $CH_3O$ | H |
| 46 | General Formula (12) | H | CN | H | General Formula (12) | H | H | $t\text{-}C_4H_9$ | H |
| 47 | General Formula (12) | H | CN | H | General Formula (12) | H | H | Cl | H |
| 48 | General Formula (12) | H | CN | H | General Formula (12) | H | H | F | H |
| 49 | General Formula (12) | H | CN | H | General Formula (12) | H | H | H | $CH_3$ |

TABLE 1-continued

| Compound No. | General Formula (1) | | | | | General Formula (12) | | | |
|---|---|---|---|---|---|---|---|---|---|
| | $R^1$ | $R^2$ | $R^3$ | $R^4$ | $R^5$ | $R^{31}, R^{38}$ | $R^{32}, R^{37}$ | $R^{33}, R^{36}$ | $R^{34}, R^{35}$ |
| 50 | General Formula (12) | H | CN | H | General Formula (12) | H | H | H | $CH_3O$ |
| 51 | General Formula (12) | H | CN | H | H | H | H | H | H |
| 52 | General Formula (12) | H | CN | H | H | H | $CH_3$ | H | H |
| 53 | General Formula (12) | H | CN | H | H | H | $CH_3O$ | H | H |
| 54 | General Formula (12) | H | CN | H | H | H | H | $CH_3$ | H |
| 55 | General Formula (12) | H | CN | H | H | H | H | $CH_3O$ | H |
| 56 | General Formula (12) | H | CN | H | H | H | H | $t-C_4H_9$ | H |
| 57 | General Formula (12) | H | CN | H | H | H | H | Cl | H |
| 58 | General Formula (12) | H | CN | H | H | H | H | F | H |
| 59 | General Formula (12) | H | CN | H | H | H | H | H | $CH_3$ |
| 60 | General Formula (12) | H | CN | H | H | H | H | H | $CH_3O$ |
| 61 | General Formula (12) | General Formula (12) | CN | General Formula (12) | F | H | H | H | H |
| 62 | General Formula (12) | General Formula (12) | CN | General Formula (12) | F | H | $CH_3$ | H | H |
| 63 | General Formula (12) | General Formula (12) | CN | General Formula (12) | F | H | $CH_3O$ | H | H |
| 64 | General Formula (12) | General Formula (12) | CN | General Formula (12) | F | H | H | $CH_3$ | H |
| 65 | General Formula (12) | General Formula (12) | CN | General Formula (12) | F | H | H | $CH_3O$ | H |
| 66 | General Formula (12) | General Formula (12) | CN | General Formula (12) | F | H | H | $t-C_4H_9$ | H |
| 67 | General Formula (12) | General Formula (12) | CN | General Formula (12) | F | H | H | Cl | H |
| 68 | General Formula (12) | General Formula (12) | CN | General Formula (12) | F | H | H | F | H |
| 69 | General Formula (12) | General Formula (12) | CN | General Formula (12) | F | H | H | H | $CH_3$ |
| 70 | General Formula (12) | General Formula (12) | CN | General Formula (12) | F | H | H | H | $CH_3O$ |
| 71 | General Formula (12) | General Formula (12) | CN | F | F | H | H | H | H |
| 72 | General Formula (12) | General Formula (12) | CN | F | F | H | $CH_3$ | H | H |
| 73 | General Formula (12) | General Formula (12) | CN | F | F | H | $CH_3O$ | H | H |
| 74 | General Formula (12) | General Formula (12) | CN | F | F | H | H | $CH_3$ | H |

TABLE 1-continued

| Compound No. | General Formula (1) | | | | | General Formula (12) | | | |
|---|---|---|---|---|---|---|---|---|---|
| | $R^1$ | $R^2$ | $R^3$ | $R^4$ | $R^5$ | $R^{31}, R^{38}$ | $R^{32}, R^{37}$ | $R^{33}, R^{36}$ | $R^{34}, R^{35}$ |
| 75 | General Formula (12) | General Formula (12) | CN | F | F | H | H | CH$_3$O | H |
| 76 | General Formula (12) | General Formula (12) | CN | F | F | H | H | t-C$_4$H$_9$ | H |
| 77 | General Formula (12) | General Formula (12) | CN | F | F | H | H | Cl | H |
| 78 | General Formula (12) | General Formula (12) | CN | F | F | H | H | F | H |
| 79 | General Formula (12) | General Formula (12) | CN | F | F | H | H | H | CH$_3$ |
| 80 | General Formula (12) | General Formula (12) | CN | F | F | H | H | H | CH$_3$O |
| 81 | General Formula (12) | F | CN | General Formula (12) | F | H | H | H | H |
| 82 | General Formula (12) | F | CN | General Formula (12) | F | H | CH$_3$ | H | H |
| 83 | General Formula (12) | F | CN | General Formula (12) | F | H | CH$_3$O | H | H |
| 84 | General Formula (12) | F | CN | General Formula (12) | F | H | H | CH$_3$ | H |
| 85 | General Formula (12) | F | CN | General Formula (12) | F | H | H | CH$_3$O | H |
| 86 | General Formula (12) | F | CN | General Formula (12) | F | H | H | t-C$_4$H$_9$ | H |
| 87 | General Formula (12) | F | CN | General Formula (12) | F | H | H | Cl | H |
| 88 | General Formula (12) | F | CN | General Formula (12) | F | H | H | F | H |
| 89 | General Formula (12) | F | CN | General Formula (12) | F | H | H | H | CH$_3$ |
| 90 | General Formula (12) | F | CN | General Formula (12) | F | H | H | H | CH$_3$O |
| 91 | General Formula (12) | F | CN | F | General Formula (12) | H | H | H | H |
| 92 | General Formula (12) | F | CN | F | General Formula (12) | H | CH$_3$ | H | H |
| 93 | General Formula (12) | F | CN | F | General Formula (12) | H | CH$_3$O | H | H |
| 94 | General Formula (12) | F | CN | F | General Formula (12) | H | H | CH$_3$ | H |
| 95 | General Formula (12) | F | CN | F | General Formula (12) | H | H | CH$_3$O | H |
| 96 | General Formula (12) | F | CN | F | General Formula (12) | H | H | t-C$_4$H$_9$ | H |
| 97 | General Formula (12) | F | CN | F | General Formula (12) | H | H | Cl | H |
| 98 | General Formula (12) | F | CN | F | General Formula (12) | H | H | F | H |
| 99 | General Formula (12) | F | CN | F | General Formula (12) | H | H | H | CH$_3$ |

TABLE 1-continued

| Compound No. | General Formula (1) | | | | | General Formula (12) | | | |
|---|---|---|---|---|---|---|---|---|---|
| | $R^1$ | $R^2$ | $R^3$ | $R^4$ | $R^5$ | $R^{31}, R^{38}$ | $R^{32}, R^{37}$ | $R^{33}, R^{36}$ | $R^{34}, R^{35}$ |
| 100 | General Formula (12) | F | CN | F | General Formula (12) | H | H | H | $CH_3O$ |
| 101 | General Formula (12) | F | CN | F | F | H | H | H | H |
| 102 | General Formula (12) | F | CN | F | F | H | $CH_3$ | H | H |
| 103 | General Formula (12) | F | CN | F | F | H | $CH_3O$ | H | H |
| 104 | General Formula (12) | F | CN | F | F | H | H | $CH_3$ | H |
| 105 | General Formula (12) | F | CN | F | F | H | H | $CH_3O$ | H |
| 106 | General Formula (12) | F | CN | F | F | H | H | $t-C_4H_9$ | H |
| 107 | General Formula (12) | F | CN | F | F | H | H | Cl | H |
| 108 | General Formula (12) | F | CN | F | F | H | H | F | H |
| 109 | General Formula (12) | F | CN | F | F | H | H | H | $CH_3$ |
| 110 | General Formula (12) | F | CN | F | F | H | H | H | $CH_3O$ |
| 111 | General Formula (12) | General Formula (12) | CN | General Formula (12) | OH | H | H | H | H |
| 112 | General Formula (12) | General Formula (12) | CN | General Formula (12) | OH | H | $CH_3$ | H | H |
| 113 | General Formula (12) | General Formula (12) | CN | General Formula (12) | OH | H | $CH_3O$ | H | H |
| 114 | General Formula (12) | General Formula (12) | CN | General Formula (12) | OH | H | H | $CH_3$ | H |
| 115 | General Formula (12) | General Formula (12) | CN | General Formula (12) | OH | H | H | $CH_3O$ | H |
| 116 | General Formula (12) | General Formula (12) | CN | General Formula (12) | OH | H | H | $t-C_4H_9$ | H |
| 117 | General Formula (12) | General Formula (12) | CN | General Formula (12) | OH | H | H | Cl | H |
| 118 | General Formula (12) | General Formula (12) | CN | General Formula (12) | OH | H | H | F | H |
| 119 | General Formula (12) | General Formula (12) | CN | General Formula (12) | OH | H | H | H | $CH_3$ |
| 120 | General Formula (12) | General Formula (12) | CN | General Formula (12) | OH | H | H | H | $CH_3O$ |
| 121 | General Formula (12) | General Formula (12) | CN | OH | OH | H | H | H | H |
| 122 | General Formula (12) | General Formula (12) | CN | OH | OH | H | $CH_3$ | H | H |
| 123 | General Formula (12) | General Formula (12) | CN | OH | OH | H | $CH_3O$ | H | H |
| 124 | General Formula (12) | General Formula (12) | CN | OH | OH | H | H | $CH_3$ | H |

TABLE 1-continued

| Compound No. | General Formula (1) | | | | | General Formula (12) | | | |
|---|---|---|---|---|---|---|---|---|---|
| | $R^1$ | $R^2$ | $R^3$ | $R^4$ | $R^5$ | $R^{31}, R^{38}$ | $R^{32}, R^{37}$ | $R^{33}, R^{36}$ | $R^{34}, R^{35}$ |
| 125 | General Formula (12) | General Formula (12) | CN | OH | OH | H | H | $CH_3O$ | H |
| 126 | General Formula (12) | General Formula (12) | CN | OH | OH | H | H | $t-C_4H_9$ | H |
| 127 | General Formula (12) | General Formula (12) | CN | OH | OH | H | H | Cl | H |
| 128 | General Formula (12) | General Formula (12) | CN | OH | OH | H | H | F | H |
| 129 | General Formula (12) | General Formula (12) | CN | OH | OH | H | H | H | $CH_3$ |
| 130 | General Formula (12) | General Formula (12) | CN | OH | OH | H | H | H | $CH_3O$ |
| 131 | General Formula (12) | OH | CN | General Formula (12) | OH | H | H | H | H |
| 132 | General Formula (12) | OH | CN | General Formula (12) | OH | H | $CH_3$ | H | H |
| 133 | General Formula (12) | OH | CN | General Formula (12) | OH | H | $CH_3O$ | H | H |
| 134 | General Formula (12) | OH | CN | General Formula (12) | OH | H | H | $CH_3$ | H |
| 135 | General Formula (12) | OH | CN | General Formula (12) | OH | H | H | $CH_3O$ | H |
| 136 | General Formula (12) | OH | CN | General Formula (12) | OH | H | H | $t-C_4H_9$ | H |
| 137 | General Formula (12) | OH | CN | General Formula (12) | OH | H | H | Cl | H |
| 138 | General Formula (12) | OH | CN | General Formula (12) | OH | H | H | F | H |
| 139 | General Formula (12) | OH | CN | General Formula (12) | OH | H | H | H | $CH_3$ |
| 140 | General Formula (12) | OH | CN | General Formula (12) | OH | H | H | H | $CH_3O$ |
| 141 | General Formula (12) | OH | CN | OH | General Formula (12) | H | H | H | H |
| 142 | General Formula (12) | OH | CN | OH | General Formula (12) | H | $CH_3$ | H | H |
| 143 | General Formula (12) | OH | CN | OH | General Formula (12) | H | $CH_3O$ | H | H |
| 144 | General Formula (12) | OH | CN | OH | General Formula (12) | H | H | $CH_3$ | H |
| 145 | General Formula (12) | OH | CN | OH | General Formula (12) | H | H | $CH_3O$ | H |
| 146 | General Formula (12) | OH | CN | OH | General Formula (12) | H | H | $t-C_4H_9$ | H |
| 147 | General Formula (12) | OH | CN | OH | General Formula (12) | H | H | Cl | H |
| 148 | General Formula (12) | OH | CN | OH | General Formula (12) | H | H | F | H |
| 149 | General Formula (12) | OH | CN | OH | General Formula (12) | H | H | H | $CH_3$ |

TABLE 1-continued

| Compound No. | General Formula (1) | | | | | General Formula (12) | | | |
|---|---|---|---|---|---|---|---|---|---|
| | $R^1$ | $R^2$ | $R^3$ | $R^4$ | $R^5$ | $R^{31}, R^{38}$ | $R^{32}, R^{37}$ | $R^{33}, R^{36}$ | $R^{34}, R^{35}$ |
| 150 | General Formula (12) | OH | CN | OH | General Formula (12) | H | H | H | $CH_3O$ |
| 151 | General Formula (12) | OH | CN | OH | OH | H | H | H | H |
| 152 | General Formula (12) | OH | CN | OH | OH | H | $CH_3$ | H | H |
| 153 | General Formula (12) | OH | CN | OH | OH | H | $CH_3O$ | H | H |
| 154 | General Formula (12) | OH | CN | OH | OH | H | H | $CH_3$ | H |
| 155 | General Formula (12) | OH | CN | OH | OH | H | H | $CH_3O$ | H |
| 156 | General Formula (12) | OH | CN | OH | OH | H | H | $t-C_4H_9$ | H |
| 157 | General Formula (12) | OH | CN | OH | OH | H | H | Cl | H |
| 158 | General Formula (12) | OH | CN | OH | OH | H | H | F | H |
| 159 | General Formula (12) | OH | CN | OH | OH | H | H | H | $CH_3$ |
| 160 | General Formula (12) | OH | CN | OH | OH | H | H | H | $CH_3O$ |
| 161 | General Formula (12) | General Formula (12) | CN | General Formula (12) | Cl | H | H | H | H |
| 162 | General Formula (12) | General Formula (12) | CN | General Formula (12) | Cl | H | $CH_3$ | H | H |
| 163 | General Formula (12) | General Formula (12) | CN | General Formula (12) | Cl | H | $CH_3O$ | H | H |
| 164 | General Formula (12) | General Formula (12) | CN | General Formula (12) | Cl | H | H | $CH_3$ | H |
| 165 | General Formula (12) | General Formula (12) | CN | General Formula (12) | Cl | H | H | $CH_3O$ | H |
| 166 | General Formula (12) | General Formula (12) | CN | General Formula (12) | Cl | H | H | $t-C_4H_9$ | H |
| 167 | General Formula (12) | General Formula (12) | CN | General Formula (12) | Cl | H | H | Cl | H |
| 168 | General Formula (12) | General Formula (12) | CN | General Formula (12) | Cl | H | H | F | H |
| 169 | General Formula (12) | General Formula (12) | CN | General Formula (12) | Cl | H | H | H | $CH_3$ |
| 170 | General Formula (12) | General Formula (12) | CN | General Formula (12) | Cl | H | H | H | $CH_3O$ |
| 171 | General Formula (12) | General Formula (12) | CN | General Formula (12) | F | H | H | H | H |
| 172 | General Formula (12) | General Formula (12) | CN | General Formula (12) | F | H | $CH_3$ | H | H |
| 173 | General Formula (12) | General Formula (12) | CN | General Formula (12) | F | H | $CH_3O$ | H | H |
| 174 | General Formula (12) | General Formula (12) | CN | General Formula (12) | F | H | H | $CH_3$ | H |

TABLE 1-continued

| Compound No. | General Formula (1) | | | | | General Formula (12) | | | |
|---|---|---|---|---|---|---|---|---|---|
| | $R^1$ | $R^2$ | $R^3$ | $R^4$ | $R^5$ | $R^{31}, R^{38}$ | $R^{32}, R^{37}$ | $R^{33}, R^{36}$ | $R^{34}, R^{35}$ |
| 175 | General Formula (12) | General Formula (12) | CN | General Formula (12) | F | H | H | $CH_3O$ | H |
| 176 | General Formula (12) | General Formula (12) | CN | General Formula (12) | F | H | H | $t-C_4H_9$ | H |
| 177 | General Formula (12) | General Formula (12) | CN | General Formula (12) | F | H | H | Cl | H |
| 178 | General Formula (12) | General Formula (12) | CN | General Formula (12) | F | H | H | F | H |
| 179 | General Formula (12) | General Formula (12) | CN | General Formula (12) | F | H | H | H | $CH_3$ |
| 180 | General Formula (12) | General Formula (12) | CN | General Formula (12) | F | H | H | H | $CH_3O$ |
| 181 | General Formula (12) | General Formula (12) | CN | General Formula (12) | $CH_3O$ | H | H | H | H |
| 182 | General Formula (12) | General Formula (12) | CN | General Formula (12) | $CH_3O$ | H | $CH_3$ | H | H |
| 183 | General Formula (12) | General Formula (12) | CN | General Formula (12) | $CH_3O$ | H | $CH_3O$ | H | H |
| 184 | General Formula (12) | General Formula (12) | CN | General Formula (12) | $CH_3O$ | H | H | $CH_3$ | H |
| 185 | General Formula (12) | General Formula (12) | CN | General Formula (12) | $CH_3O$ | H | H | $CH_3O$ | H |
| 186 | General Formula (12) | General Formula (12) | CN | General Formula (12) | $CH_3O$ | H | H | $t-C_4H_9$ | H |
| 187 | General Formula (12) | General Formula (12) | CN | General Formula (12) | $CH_3O$ | H | H | Cl | H |
| 188 | General Formula (12) | General Formula (12) | CN | General Formula (12) | $CH_3O$ | H | H | F | H |
| 189 | General Formula (12) | General Formula (12) | CN | General Formula (12) | $C_2H_5O$ | H | H | H | $CH_3$ |
| 190 | General Formula (12) | General Formula (12) | CN | General Formula (12) | $C_2H_5O$ | H | H | H | $CH_3O$ |
| 191 | General Formula (12) | General Formula (12) | CN | General Formula (12) | $C_2H_5O$ | H | H | H | H |
| 192 | General Formula (12) | General Formula (12) | CN | General Formula (12) | $C_2H_5O$ | H | $CH_3$ | H | H |
| 193 | General Formula (12) | General Formula (12) | CN | General Formula (12) | $C_2H_5O$ | H | $CH_3O$ | H | H |
| 194 | General Formula (12) | General Formula (12) | CN | General Formula (12) | $C_2H_5O$ | H | H | $CH_3$ | H |
| 195 | General Formula (12) | General Formula (12) | CN | General Formula (12) | $C_2H_5O$ | H | H | $CH_3O$ | H |
| 196 | General Formula (12) | General Formula (12) | CN | General Formula (12) | $C_2H_5O$ | H | H | $t-C_4H_9$ | H |
| 197 | General Formula (12) | General Formula (12) | CN | General Formula (12) | $C_2H_5O$ | H | H | Cl | H |
| 198 | General Formula (12) | General Formula (12) | CN | General Formula (12) | $C_2H_5O$ | H | H | F | H |
| 199 | General Formula (12) | General Formula (12) | CN | General Formula (12) | $C_2H_5O$ | H | H | H | $CH_3$ |

TABLE 1-continued

| Compound No. | General Formula (1) | | | | | General Formula (12) | | | |
|---|---|---|---|---|---|---|---|---|---|
| | $R^1$ | $R^2$ | $R^3$ | $R^4$ | $R^5$ | $R^{31}, R^{38}$ | $R^{32}, R^{37}$ | $R^{33}, R^{36}$ | $R^{34}, R^{35}$ |
| 200 | General Formula (12) | General Formula (12) | CN | General Formula (12) | $C_2H_5O$ | H | H | H | $CH_3O$ |
| 201 | General Formula (12) | General Formula (12) | CN | General Formula (12) | $C_6H_5O$ | H | H | H | H |
| 202 | General Formula (12) | General Formula (12) | CN | General Formula (12) | $C_6H_5O$ | H | $CH_3$ | H | H |
| 203 | General Formula (12) | General Formula (12) | CN | General Formula (12) | $C_6H_5O$ | H | $CH_3O$ | H | H |
| 204 | General Formula (12) | General Formula (12) | CN | General Formula (12) | $C_6H_5O$ | H | H | $CH_3$ | H |
| 205 | General Formula (12) | General Formula (12) | CN | General Formula (12) | $C_6H_5O$ | H | H | $CH_3O$ | H |
| 206 | General Formula (12) | General Formula (12) | CN | General Formula (12) | $C_6H_5O$ | H | H | $t-C_4H_9$ | H |
| 207 | General Formula (12) | General Formula (12) | CN | General Formula (12) | $C_6H_5O$ | H | H | Cl | H |
| 208 | General Formula (12) | General Formula (12) | CN | General Formula (12) | $C_6H_5O$ | H | H | F | H |
| 209 | General Formula (12) | General Formula (12) | CN | General Formula (12) | $C_6H_5O$ | H | H | H | $CH_3$ |
| 210 | General Formula (12) | General Formula (12) | CN | General Formula (12) | $C_6H_5O$ | H | H | H | $CH_3O$ |
| 211 | General Formula (12) | General Formula (12) | CN | General Formula (12) | Formula (21) | H | H | H | H |
| 212 | General Formula (12) | General Formula (12) | CN | General Formula (12) | Formula (21) | H | $CH_3$ | H | H |
| 213 | General Formula (12) | General Formula (12) | CN | General Formula (12) | Formula (21) | H | $CH_3O$ | H | H |
| 214 | General Formula (12) | General Formula (12) | CN | General Formula (12) | Formula (21) | H | H | $CH_3$ | H |
| 215 | General Formula (12) | General Formula (12) | CN | General Formula (12) | Formula (21) | H | H | $CH_3O$ | H |
| 216 | General Formula (12) | General Formula (12) | CN | General Formula (12) | Formula (21) | H | H | $t-C_4H_9$ | H |
| 217 | General Formula (12) | General Formula (12) | CN | General Formula (12) | Formula (21) | H | H | Cl | H |
| 218 | General Formula (12) | General Formula (12) | CN | General Formula (12) | Formula (21) | H | H | F | H |
| 219 | General Formula (12) | General Formula (12) | CN | General Formula (12) | Formula (21) | H | H | H | $CH_3$ |
| 220 | General Formula (12) | General Formula (12) | CN | General Formula (12) | Formula (21) | H | H | H | $CH_3O$ |
| 221 | General Formula (12) | General Formula (12) | CN | General Formula (12) | Formula (22) | H | H | H | H |
| 222 | General Formula (12) | General Formula (12) | CN | General Formula (12) | Formula (22) | H | $CH_3$ | H | H |
| 223 | General Formula (12) | General Formula (12) | CN | General Formula (12) | Formula (22) | H | $CH_3O$ | H | H |
| 224 | General Formula (12) | General Formula (12) | CN | General Formula (12) | Formula (22) | H | H | $CH_3$ | H |

TABLE 1-continued

| Compound No. | General Formula (1) | | | | | General Formula (12) | | | |
|---|---|---|---|---|---|---|---|---|---|
| | $R^1$ | $R^2$ | $R^3$ | $R^4$ | $R^5$ | $R^{31}, R^{38}$ | $R^{32}, R^{37}$ | $R^{33}, R^{36}$ | $R^{34}, R^{35}$ |
| 225 | General Formula (12) | General Formula (12) | CN | General Formula (22) | | H | H | $CH_3O$ | H |
| 226 | General Formula (12) | General Formula (12) | CN | General Formula (22) | | H | H | $t-C_4H_9$ | H |
| 227 | General Formula (12) | General Formula (12) | CN | General Formula (22) | | H | H | Cl | H |
| 228 | General Formula (12) | General Formula (12) | CN | General Formula (22) | | H | H | F | H |
| 229 | General Formula (12) | General Formula (12) | CN | General Formula (22) | | H | H | H | $CH_3$ |
| 230 | General Formula (12) | General Formula (12) | CN | General Formula (22) | | H | H | H | $CH_3O$ |
| 231 | General Formula (12) | General Formula (12) | CN | General Formula (23) | | H | H | H | H |
| 232 | General Formula (12) | General Formula (12) | CN | General Formula (23) | | H | $CH_3$ | H | H |
| 233 | General Formula (12) | General Formula (12) | CN | General Formula (23) | | H | $CH_3O$ | H | H |
| 234 | General Formula (12) | General Formula (12) | CN | General Formula (23) | | H | H | $CH_3$ | H |
| 235 | General Formula (12) | General Formula (12) | CN | General Formula (23) | | H | H | $CH_3O$ | H |
| 236 | General Formula (12) | General Formula (12) | CN | General Formula (23) | | H | H | $t-C_4H_9$ | H |
| 237 | General Formula (12) | General Formula (12) | CN | General Formula (23) | | H | H | Cl | H |
| 238 | General Formula (12) | General Formula (12) | CN | General Formula (23) | | H | H | F | H |
| 239 | General Formula (12) | General Formula (12) | CN | General Formula (23) | | H | H | H | $CH_3$ |
| 240 | General Formula (12) | General Formula (12) | CN | General Formula (23) | | H | H | H | $CH_3O$ |
| 241 | General Formula (12) | General Formula (12) | CN | General Formula (24) | | H | H | H | H |
| 242 | General Formula (12) | General Formula (12) | CN | General Formula (24) | | H | $CH_3$ | H | H |
| 243 | General Formula (12) | General Formula (12) | CN | General Formula (24) | | H | $CH_3O$ | H | H |
| 244 | General Formula (12) | General Formula (12) | CN | General Formula (24) | | H | H | $CH_3$ | H |
| 245 | General Formula (12) | General Formula (12) | CN | General Formula (24) | | H | H | $CH_3O$ | H |
| 246 | General Formula (12) | General Formula (12) | CN | General Formula (24) | | H | H | $t-C_4H_9$ | H |
| 247 | General Formula (12) | General Formula (12) | CN | General Formula (24) | | H | H | Cl | H |
| 248 | General Formula (12) | General Formula (12) | CN | General Formula (24) | | H | H | F | H |
| 249 | General Formula (12) | General Formula (12) | CN | General Formula (24) | | H | H | H | $CH_3$ |

TABLE 1-continued

| Compound No. | General Formula (1) | | | | | General Formula (12) | | | |
|---|---|---|---|---|---|---|---|---|---|
| | $R^1$ | $R^2$ | $R^3$ | $R^4$ | $R^5$ | $R^{31}, R^{38}$ | $R^{32}, R^{37}$ | $R^{33}, R^{36}$ | $R^{34}, R^{35}$ |
| 250 | General Formula (12) | General Formula (12) | CN | General Formula (12) | Formula (24) | H | H | H | CH$_3$O |
| 251 | General Formula (12) | General Formula (12) | CN | General Formula (12) | General Formula (12) | H | C$_6$H$_5$ | H | H |
| 252 | General Formula (12) | General Formula (12) | CN | General Formula (12) | General Formula (12) | H | H | C$_6$H$_5$ | H |
| 253 | General Formula (12) | General Formula (12) | CN | General Formula (12) | H | H | C$_6$H$_5$ | H | H |
| 254 | General Formula (12) | General Formula (12) | CN | General Formula (12) | H | H | H | C$_6$H$_5$ | H |
| 255 | General Formula (12) | General Formula (12) | CN | H | H | H | C$_6$H$_5$ | H | H |
| 256 | General Formula (12) | General Formula (12) | CN | H | H | H | H | C$_6$H$_5$ | H |
| 257 | General Formula (12) | H | CN | General Formula (12) | H | H | C$_6$H$_5$ | H | H |
| 258 | General Formula (12) | H | CN | General Formula (12) | H | H | H | C$_6$H$_5$ | H |
| 259 | General Formula (12) | H | CN | H | General Formula (12) | H | C$_6$H$_5$ | H | H |
| 260 | General Formula (12) | H | CN | H | General Formula (12) | H | H | C$_6$H$_5$ | H |
| 261 | General Formula (12) | H | CN | H | H | H | C$_6$H$_5$ | H | H |
| 262 | General Formula (12) | H | CN | H | H | H | H | C$_6$H$_5$ | H |
| 263 | General Formula (12) | General Formula (12) | CN | General Formula (12) | F | H | C$_6$H$_5$ | H | H |
| 264 | General Formula (12) | General Formula (12) | CN | General Formula (12) | F | H | H | C$_6$H$_5$ | H |
| 265 | General Formula (12) | General Formula (12) | CN | F | F | H | C$_6$H$_5$ | H | H |
| 266 | General Formula (12) | General Formula (12) | CN | F | F | H | H | C$_6$H$_5$ | H |
| 267 | General Formula (12) | F | CN | General Formula (12) | F | H | C$_6$H$_5$ | H | H |
| 268 | General Formula (12) | F | CN | General Formula (12) | F | H | H | C$_6$H$_5$ | H |
| 269 | General Formula (12) | F | CN | F | General Formula (12) | H | C$_6$H$_5$ | H | H |
| 270 | General Formula (12) | F | CN | F | General Formula (12) | H | H | C$_6$H$_5$ | H |
| 271 | General Formula (12) | F | CN | F | F | H | C$_6$H$_5$ | H | H |
| 272 | General Formula (12) | F | CN | F | F | H | H | C$_6$H$_5$ | H |
| 273 | General Formula (12) | General Formula (12) | CN | General Formula (12) | OH | H | C$_6$H$_5$ | H | H |
| 274 | General Formula (12) | General Formula (12) | CN | General Formula (12) | OH | H | H | C$_6$H$_5$ | H |

TABLE 1-continued

| Compound No. | General Formula (1) | | | | | General Formula (12) | | | |
|---|---|---|---|---|---|---|---|---|---|
| | $R^1$ | $R^2$ | $R^3$ | $R^4$ | $R^5$ | $R^{31}, R^{38}$ | $R^{32}, R^{37}$ | $R^{33}, R^{36}$ | $R^{34}, R^{35}$ |
| 275 | General Formula (12) | General Formula (12) | CN | OH | OH | H | $C_6H_5$ | H | H |
| 276 | General Formula (12) | General Formula (12) | CN | OH | OH | H | H | $C_6H_5$ | H |
| 277 | General Formula (12) | OH | CN | General Formula (12) | OH | H | $C_6H_5$ | H | H |
| 278 | General Formula (12) | OH | CN | General Formula (12) | OH | H | H | $C_6H_5$ | H |
| 279 | General Formula (12) | OH | CN | OH | General Formula (12) | H | $C_6H_5$ | H | H |
| 280 | General Formula (12) | OH | CN | OH | General Formula (12) | H | H | $C_6H_5$ | H |
| 281 | General Formula (12) | OH | CN | OH | OH | H | $C_6H_5$ | H | H |
| 282 | General Formula (12) | OH | CN | OH | OH | H | H | $C_6H_5$ | H |
| 283 | General Formula (12) | General Formula (12) | CN | General Formula (12) | Cl | H | $C_6H_5$ | H | H |
| 284 | General Formula (12) | General Formula (12) | CN | General Formula (12) | Cl | H | H | $C_6H_5$ | H |
| 285 | General Formula (12) | General Formula (12) | CN | General Formula (12) | F | H | $C_6H_5$ | H | H |
| 286 | General Formula (12) | General Formula (12) | CN | General Formula (12) | F | H | H | $C_6H_5$ | H |
| 287 | General Formula (12) | General Formula (12) | CN | General Formula (12) | $CH_3O$ | H | $C_6H_5$ | H | H |
| 288 | General Formula (12) | General Formula (12) | CN | General Formula (12) | $CH_3O$ | H | H | $C_6H_5$ | H |
| 289 | General Formula (12) | General Formula (12) | CN | General Formula (12) | $C_2H_5O$ | H | $C_6H_5$ | H | H |
| 290 | General Formula (12) | General Formula (12) | CN | General Formula (12) | $C_2H_5O$ | H | H | $C_6H_5$ | H |
| 291 | General Formula (12) | General Formula (12) | CN | General Formula (12) | $C_6H_5O$ | H | $C_6H_5$ | H | H |
| 292 | General Formula (12) | General Formula (12) | CN | General Formula (12) | $C_6H_5O$ | H | H | $C_6H_5$ | H |
| 293 | General Formula (12) | General Formula (12) | CN | General Formula (12) | Formula (21) | H | $C_6H_5$ | H | H |
| 294 | General Formula (12) | General Formula (12) | CN | General Formula (12) | Formula (21) | H | H | $C_6H_5$ | H |
| 295 | General Formula (12) | General Formula (12) | CN | General Formula (12) | Formula (22) | H | $C_6H_5$ | H | H |
| 296 | General Formula (12) | General Formula (12) | CN | General Formula (12) | Formula (22) | H | H | $C_6H_5$ | H |
| 297 | General Formula (12) | General Formula (12) | CN | General Formula (12) | Formula (23) | H | $C_6H_5$ | H | H |
| 298 | General Formula (12) | General Formula (12) | CN | General Formula (12) | Formula (23) | H | H | $C_6H_5$ | H |
| 299 | General Formula (12) | General Formula (12) | CN | General Formula (12) | Formula (24) | H | $C_6H_5$ | H | H |

TABLE 1-continued

| Compound No. | General Formula (1) | | | | | General Formula (12) | | | |
|---|---|---|---|---|---|---|---|---|---|
| | $R^1$ | $R^2$ | $R^3$ | $R^4$ | $R^5$ | $R^{31}, R^{38}$ | $R^{32}, R^{37}$ | $R^{33}, R^{36}$ | $R^{34}, R^{35}$ |
| 300 | General Formula (12) | General Formula (12) | CN | General Formula (24) | General Formula (12) | H | H | $C_6H_5$ | H |

TABLE 2

| Compound No. | General Formula (1) | | | | | General Formula (12) | | | |
|---|---|---|---|---|---|---|---|---|---|
| | $R^1$ | $R^2$ | $R^3$ | $R^4$ | $R^5$ | $R^{31}, R^{38}$ | $R^{32}, R^{37}$ | $R^{33}, R^{36}$ | $R^{34}, R^{35}$ |
| 301 | General Formula (12) | CN | General Formula (12) | General Formula (12) | General Formula (12) | H | H | H | H |
| 302 | General Formula (12) | CN | General Formula (12) | General Formula (12) | General Formula (12) | H | $CH_3$ | H | H |
| 303 | General Formula (12) | CN | General Formula (12) | General Formula (12) | General Formula (12) | H | $CH_3O$ | H | H |
| 304 | General Formula (12) | CN | General Formula (12) | General Formula (12) | General Formula (12) | H | H | $CH_3$ | H |
| 305 | General Formula (12) | CN | General Formula (12) | General Formula (12) | General Formula (12) | H | H | $CH_3O$ | H |
| 306 | General Formula (12) | CN | General Formula (12) | General Formula (12) | General Formula (12) | H | H | $t-C_4H_9$ | H |
| 307 | General Formula (12) | CN | General Formula (12) | General Formula (12) | General Formula (12) | H | H | Cl | H |
| 308 | General Formula (12) | CN | General Formula (12) | General Formula (12) | General Formula (12) | H | H | F | H |
| 309 | General Formula (12) | CN | General Formula (12) | General Formula (12) | General Formula (12) | H | H | H | $CH_3$ |
| 310 | General Formula (12) | CN | General Formula (12) | General Formula (12) | General Formula (12) | H | H | H | $CH_3O$ |
| 311 | General Formula (12) | CN | General Formula (12) | General Formula (12) | H | H | H | H | H |
| 312 | General Formula (12) | CN | General Formula (12) | General Formula (12) | H | H | H | $CH_3$ | H |
| 313 | General Formula (12) | CN | General Formula (12) | General Formula (12) | H | H | H | $CH_3O$ | H |
| 314 | General Formula (12) | CN | General Formula (12) | H | General Formula (12) | H | H | H | H |
| 315 | General Formula (12) | CN | General Formula (12) | H | General Formula (12) | H | H | $CH_3$ | H |
| 316 | General Formula (12) | CN | General Formula (12) | H | General Formula (12) | H | H | $CH_3O$ | H |
| 317 | General Formula (12) | CN | H | General Formula (12) | General Formula (12) | H | H | H | H |
| 318 | General Formula (12) | CN | H | General Formula (12) | General Formula (12) | H | H | $CH_3$ | H |
| 319 | General Formula (12) | CN | H | General Formula (12) | General Formula (12) | H | H | $CH_3O$ | H |
| 320 | H | CN | General Formula (12) | General Formula (12) | General Formula (12) | H | H | H | H |
| 321 | H | CN | General Formula (12) | General Formula (12) | General Formula (12) | H | H | $CH_3$ | H |

TABLE 2-continued

| Compound No. | General Formula (1) | | | | | General Formula (12) | | | |
|---|---|---|---|---|---|---|---|---|---|
| | $R^1$ | $R^2$ | $R^3$ | $R^4$ | $R^5$ | $R^{31}, R^{38}$ | $R^{32}, R^{37}$ | $R^{33}, R^{36}$ | $R^{34}, R^{35}$ |
| 322 | H | CN | General Formula (12) | General Formula (12) | General Formula (12) | H | H | $CH_3O$ | H |
| 323 | General Formula (12) | CN | General Formula (12) | H | H | H | H | H | H |
| 324 | General Formula (12) | CN | General Formula (12) | H | H | H | H | $CH_3$ | H |
| 325 | General Formula (12) | CN | General Formula (12) | H | H | H | H | $CH_3O$ | H |
| 326 | General Formula (12) | CN | H | General Formula (12) | H | H | H | H | H |
| 327 | General Formula (12) | CN | H | General Formula (12) | H | H | H | $CH_3$ | H |
| 328 | General Formula (12) | CN | H | General Formula (12) | H | H | H | $CH_3O$ | H |
| 329 | H | CN | General Formula (12) | General Formula (12) | H | H | H | H | H |
| 330 | H | CN | General Formula (12) | General Formula (12) | H | H | H | $CH_3$ | H |
| 331 | H | CN | General Formula (12) | General Formula (12) | H | H | H | $CH_3O$ | H |
| 332 | General Formula (12) | CN | H | H | General Formula (12) | H | H | H | H |
| 333 | General Formula (12) | CN | H | H | General Formula (12) | H | H | $CH_3$ | H |
| 334 | General Formula (12) | CN | H | H | General Formula (12) | H | H | $CH_3O$ | H |
| 335 | H | CN | General Formula (12) | H | General Formula (12) | H | H | H | H |
| 336 | H | CN | General Formula (12) | H | General Formula (12) | H | H | $CH_3$ | H |
| 337 | H | CN | General Formula (12) | H | General Formula (12) | H | H | $CH_3O$ | H |
| 338 | H | CN | H | General Formula (12) | General Formula (12) | H | H | H | H |
| 339 | H | CN | H | General Formula (12) | General Formula (12) | H | H | $CH_3$ | H |
| 340 | H | CN | H | General Formula (12) | General Formula (12) | H | H | $CH_3O$ | H |
| 341 | General Formula (12) | CN | H | H | H | H | H | H | H |
| 342 | General Formula (12) | CN | H | H | H | H | H | $CH_3$ | H |
| 343 | General Formula (12) | CN | H | H | H | H | H | $CH_3O$ | H |
| 344 | H | CN | General Formula (12) | H | H | H | H | H | H |
| 345 | H | CN | General Formula (12) | H | H | H | H | $CH_3$ | H |
| 346 | H | CN | General Formula (12) | H | H | H | H | $CH_3O$ | H |

TABLE 2-continued

| Compound No. | General Formula (1) | | | | | General Formula (12) | | | |
|---|---|---|---|---|---|---|---|---|---|
| | $R^1$ | $R^2$ | $R^3$ | $R^4$ | $R^5$ | $R^{31}, R^{38}$ | $R^{32}, R^{37}$ | $R^{33}, R^{36}$ | $R^{34}, R^{35}$ |
| 347 | H | CN | H | General Formula (12) | H | H | H | H | H |
| 348 | H | CN | H | General Formula (12) | H | H | H | CH$_3$ | H |
| 349 | H | CN | H | General Formula (12) | H | H | H | CH$_3$O | H |
| 350 | General Formula (12) | CN | General Formula (12) | General Formula (12) | F | H | H | H | H |
| 351 | General Formula (12) | CN | General Formula (12) | General Formula (12) | F | H | H | CH$_3$ | H |
| 352 | General Formula (12) | CN | General Formula (12) | General Formula (12) | F | H | H | CH$_3$O | H |
| 353 | General Formula (12) | CN | General Formula (12) | F | General Formula (12) | H | H | H | H |
| 354 | General Formula (12) | CN | General Formula (12) | F | General Formula (12) | H | H | CH$_3$ | H |
| 355 | General Formula (12) | CN | General Formula (12) | F | General Formula (12) | H | H | CH$_3$O | H |
| 356 | General Formula (12) | CN | F | General Formula (12) | General Formula (12) | H | H | H | H |
| 357 | General Formula (12) | CN | F | General Formula (12) | General Formula (12) | H | H | CH$_3$ | H |
| 358 | General Formula (12) | CN | F | General Formula (12) | General Formula (12) | H | H | CH$_3$O | H |
| 359 | F | CN | General Formula (12) | General Formula (12) | General Formula (12) | H | H | H | H |
| 360 | F | CN | General Formula (12) | General Formula (12) | General Formula (12) | H | H | CH$_3$ | H |
| 361 | F | CN | General Formula (12) | General Formula (12) | General Formula (12) | H | H | CH$_3$O | H |
| 362 | General Formula (12) | CN | General Formula (12) | F | F | H | H | H | H |
| 363 | General Formula (12) | CN | General Formula (12) | F | F | H | H | CH$_3$ | H |
| 364 | General Formula (12) | CN | General Formula (12) | F | F | H | H | CH$_3$O | H |
| 365 | General Formula (12) | CN | F | General Formula (12) | F | H | H | H | H |
| 366 | General Formula (12) | CN | F | General Formula (12) | F | H | H | CH$_3$ | H |
| 367 | General Formula (12) | CN | F | General Formula (12) | F | H | H | CH$_3$O | H |
| 368 | F | CN | General Formula (12) | General Formula (12) | F | H | H | H | H |
| 369 | F | CN | General Formula (12) | General Formula (12) | F | H | H | CH$_3$ | H |
| 370 | F | CN | General Formula (12) | General Formula (12) | F | H | H | CH$_3$O | H |
| 371 | General Formula (12) | CN | F | F | General Formula (12) | H | H | H | H |

TABLE 2-continued

| Compound No. | General Formula (1) | | | | | General Formula (12) | | | |
|---|---|---|---|---|---|---|---|---|---|
| | $R^1$ | $R^2$ | $R^3$ | $R^4$ | $R^5$ | $R^{31}, R^{38}$ | $R^{32}, R^{37}$ | $R^{33}, R^{36}$ | $R^{34}, R^{35}$ |
| 372 | General Formula (12) | CN | F | F | General Formula (12) | H | H | $CH_3$ | H |
| 373 | General Formula (12) | CN | F | F | General Formula (12) | H | H | $CH_3O$ | H |
| 374 | F | CN | General Formula (12) | F | General Formula (12) | H | H | H | H |
| 375 | F | CN | General Formula (12) | F | General Formula (12) | H | H | $CH_3$ | H |
| 376 | F | CN | General Formula (12) | F | General Formula (12) | H | H | $CH_3O$ | H |
| 377 | F | CN | F | General Formula (12) | General Formula (12) | H | H | H | H |
| 378 | F | CN | F | General Formula (12) | General Formula (12) | H | H | $CH_3$ | H |
| 379 | F | CN | F | General Formula (12) | General Formula (12) | H | H | $CH_3O$ | H |
| 380 | General Formula (12) | CN | F | F | F | H | H | H | H |
| 381 | General Formula (12) | CN | F | F | F | H | H | $CH_3$ | H |
| 382 | General Formula (12) | CN | F | F | F | H | H | $CH_3O$ | H |
| 383 | F | CN | General Formula (12) | F | F | H | H | H | H |
| 384 | F | CN | General Formula (12) | F | F | H | H | $CH_3$ | H |
| 385 | F | CN | General Formula (12) | F | F | H | H | $CH_3O$ | H |
| 386 | F | CN | F | General Formula (12) | F | H | H | H | H |
| 387 | F | CN | F | General Formula (12) | F | H | H | $CH_3$ | H |
| 388 | F | CN | F | General Formula (12) | F | H | H | $CH_3O$ | H |
| 389 | General Formula (12) | CN | General Formula (12) | General Formula (12) | OH | H | H | H | H |
| 390 | General Formula (12) | CN | General Formula (12) | General Formula (12) | OH | H | H | $CH_3$ | H |
| 391 | General Formula (12) | CN | General Formula (12) | General Formula (12) | OH | H | H | $CH_3O$ | H |
| 392 | General Formula (12) | CN | General Formula (12) | OH | General Formula (12) | H | H | H | H |
| 393 | General Formula (12) | CN | General Formula (12) | OH | General Formula (12) | H | H | $CH_3$ | H |
| 394 | General Formula (12) | CN | General Formula (12) | OH | General Formula (12) | H | H | $CH_3O$ | H |
| 395 | General Formula (12) | CN | General Formula (12) | OH | General Formula (12) | H | H | $t-C_4H_9$ | H |
| 396 | General Formula (12) | CH | General Formula (12) | OH | General Formula (12) | H | H | Cl | H |

TABLE 2-continued

| Compound No. | General Formula (1) R¹ | R² | R³ | R⁴ | R⁵ | General Formula (12) R³¹, R³⁸ | R³², R³⁷ | R³³, R³⁶ | R³⁴, R³⁵ |
|---|---|---|---|---|---|---|---|---|---|
| 397 | General Formula (12) | CN | General Formula (12) | OH | General Formula (12) | H | H | F | H |
| 398 | General Formula (12) | CN | OH | General Formula (12) | General Formula (12) | H | H | H | H |
| 399 | General Formula (12) | CN | OH | General Formula (12) | General Formula (12) | H | H | $CH_3$ | H |
| 400 | General Formula (12) | CN | OH | General Formula (12) | General Formula (12) | H | H | $CH_3O$ | H |
| 401 | OH | CN | General Formula (12) | General Formula (12) | General Formula (12) | H | H | H | H |
| 402 | OH | CN | General Formula (12) | General Formula (12) | General Formula (12) | H | H | $CH_3$ | H |
| 403 | OH | CN | General Formula (12) | General Formula (12) | General Formula (12) | H | H | $CH_3O$ | H |
| 404 | General Formula (12) | CN | General Formula (12) | OH | OH | H | H | H | H |
| 405 | General Formula (12) | CN | General Formula (12) | OH | OH | H | H | $CH_3$ | H |
| 406 | General Formula (12) | CN | General Formula (12) | OH | OH | H | H | $CH_3O$ | H |
| 407 | General Formula (12) | CN | OH | General Formula (12) | OH | H | H | H | H |
| 408 | General Formula (12) | CN | OH | General Formula (12) | OH | H | H | $CH_3$ | H |
| 409 | General Formula (12) | CN | OH | General Formula (12) | OH | H | H | $CH_3O$ | H |
| 410 | OH | CN | General Formula (12) | General Formula (12) | OH | H | H | H | H |
| 411 | OH | CN | General Formula (12) | General Formula (12) | OH | H | H | $CH_3$ | H |
| 412 | OH | CN | General Formula (12) | General Formula (12) | OH | H | H | $CH_3O$ | H |
| 413 | General Formula (12) | CN | OH | OH | General Formula (12) | H | H | H | H |
| 414 | General Formula (12) | CN | OH | OH | General Formula (12) | H | H | $CH_3$ | H |
| 415 | General Formula (12) | CN | OH | OH | General Formula (12) | H | H | $CH_3O$ | H |
| 416 | OH | CN | General Formula (12) | OH | General Formula (12) | H | H | H | H |
| 417 | OH | CN | General Formula (12) | OH | General Formula (12) | H | H | $CH_3$ | H |
| 418 | OH | CN | General Formula (12) | OH | General Formula (12) | H | H | $CH_3O$ | H |
| 419 | OH | CN | OH | General Formula (12) | General Formula (12) | H | H | H | H |
| 420 | OH | CN | OH | General Formula (12) | General Formula (12) | H | H | $CH_3$ | H |
| 421 | OH | CN | OH | General Formula (12) | General Formula (12) | H | H | $CH_3O$ | H |

TABLE 2-continued

| Compound No. | General Formula (1) | | | | | General Formula (12) | | | |
|---|---|---|---|---|---|---|---|---|---|
| | $R^1$ | $R^2$ | $R^3$ | $R^4$ | $R^5$ | $R^{31}, R^{38}$ | $R^{32}, R^{37}$ | $R^{33}, R^{36}$ | $R^{34}, R^{35}$ |
| 422 | General Formula (12) | CN | OH | OH | OH | H | H | H | H |
| 423 | General Formula (12) | CN | OH | OH | OH | H | H | CH$_3$ | H |
| 424 | General Formula (12) | CN | OH | OH | OH | H | H | CH$_3$O | H |
| 425 | OH | CN | General Formula (12) | OH | OH | H | H | H | H |
| 426 | OH | CN | General Formula (12) | OH | OH | H | H | CH$_3$ | H |
| 427 | OH | CN | General Formula (12) | OH | OH | H | H | CH$_3$O | H |
| 428 | OH | CN | OH | General Formula (12) | OH | H | H | H | H |
| 429 | OH | CN | OH | General Formula (12) | OH | H | H | CH$_3$ | H |
| 430 | OH | CN | OH | General Formula (12) | OH | H | H | CH$_3$O | H |
| 431 | OH | CN | OH | OH | General Formula (12) | H | H | H | H |
| 432 | OH | CN | OH | OH | General Formula (12) | H | H | CH$_3$ | H |
| 433 | OH | CN | OH | OH | General Formula (12) | H | H | CH$_3$O | H |
| 434 | General Formula (12) | CN | General Formula (12) | Cl | General Formula (12) | H | H | H | H |
| 435 | General Formula (12) | CN | General Formula (12) | Cl | General Formula (12) | H | H | CH$_3$ | H |
| 436 | General Formula (12) | CN | General Formula (12) | Cl | General Formula (12) | H | H | CH$_3$O | H |
| 437 | General Formula (12) | CN | General Formula (12) | Cl | General Formula (12) | H | H | t-C$_4$H$_9$ | H |
| 438 | General Formula (12) | CN | General Formula (12) | Cl | General Formula (12) | H | H | Cl | H |
| 439 | General Formula (12) | CN | General Formula (12) | Cl | General Formula (12) | H | H | F | H |
| 440 | General Formula (12) | CN | General Formula (12) | F | General Formula (12) | H | H | H | H |
| 441 | General Formula (12) | CN | General Formula (12) | F | General Formula (12) | H | H | CH$_3$ | H |
| 442 | General Formula (12) | CN | General Formula (12) | F | General Formula (12) | H | H | CH$_3$O | H |
| 443 | General Formula (12) | CN | General Formula (12) | F | General Formula (12) | H | H | t-C$_4$H$_9$ | H |
| 444 | General Formula (12) | CN | General Formula (12) | F | General Formula (12) | H | H | Cl | H |
| 445 | General Formula (12) | CN | General Formula (12) | F | General Formula (12) | H | H | F | H |
| 446 | General Formula (12) | CN | General Formula (12) | CH$_3$O | General Formula (12) | H | H | H | H |

TABLE 2-continued

| Compound No. | General Formula (1) R$^1$ | R$^2$ | R$^3$ | R$^4$ | R$^5$ | General Formula (12) R$^{31}$, R$^{38}$ | R$^{32}$, R$^{37}$ | R$^{33}$, R$^{36}$ | R$^{34}$, R$^{35}$ |
|---|---|---|---|---|---|---|---|---|---|
| 447 | General Formula (12) | CN | General Formula (12) | CH$_3$O | General Formula (12) | H | H | CH$_3$ | H |
| 448 | General Formula (12) | CN | General Formula (12) | CH$_3$O | General Formula (12) | H | H | CH$_3$O | H |
| 449 | General Formula (12) | CN | General Formula (12) | CH$_3$O | General Formula (12) | H | H | t-C$_4$H$_9$ | H |
| 450 | General Formula (12) | CN | General Formula (12) | CH$_3$O | General Formula (12) | H | H | Cl | H |
| 451 | General Formula (12) | CN | General Formula (12) | CH$_3$O | General Formula (12) | H | H | F | H |
| 452 | General Formula (12) | CN | General Formula (12) | C$_2$H$_5$O | General Formula (12) | H | H | H | H |
| 453 | General Formula (12) | CN | General Formula (12) | C$_2$H$_5$O | General Formula (12) | H | H | CH$_3$ | H |
| 454 | General Formula (12) | CN | General Formula (12) | C$_2$H$_5$O | General Formula (12) | H | H | CH$_3$O | H |
| 455 | General Formula (12) | CN | General Formula (12) | C$_2$H$_5$O | General Formula (12) | H | H | t-C$_4$H$_9$ | H |
| 456 | General Formula (12) | CN | General Formula (12) | C$_2$H$_5$O | General Formula (12) | H | H | Cl | H |
| 457 | General Formula (12) | CN | General Formula (12) | C$_2$H$_5$O | General Formula (12) | H | H | F | H |
| 458 | General Formula (12) | CN | General Formula (12) | C$_6$H$_5$O | General Formula (12) | H | H | H | H |
| 459 | General Formula (12) | CN | General Formula (12) | C$_6$H$_5$O | General Formula (12) | H | H | CH$_3$ | H |
| 460 | General Formula (12) | CN | General Formula (12) | C$_6$H$_5$O | General Formula (12) | H | H | CH$_3$O | H |
| 461 | General Formula (12) | CN | General Formula (12) | C$_6$H$_5$O | General Formula (12) | H | H | t-C$_4$H$_9$ | H |
| 462 | General Formula (12) | CN | General Formula (12) | C$_6$H$_5$O | General Formula (12) | H | H | Cl | H |
| 463 | General Formula (12) | CN | General Formula (12) | C$_6$H$_5$O | General Formula (12) | H | H | F | H |
| 464 | General Formula (12) | CN | General Formula (12) | General Formula (21) | General Formula (12) | H | H | H | H |
| 465 | General Formula (12) | CN | General Formula (12) | General Formula (21) | General Formula (12) | H | H | CH$_3$ | H |
| 466 | General Formula (12) | CN | General Formula (12) | General Formula (21) | General Formula (12) | H | H | CH$_3$O | H |
| 467 | General Formula (12) | CN | General Formula (12) | General Formula (21) | General Formula (12) | H | H | t-C$_4$H$_9$ | H |
| 468 | General Formula (12) | CN | General Formula (12) | General Formula (21) | General Formula (12) | H | H | Cl | H |
| 469 | General Formula (12) | CN | General Formula (12) | General Formula (21) | General Formula (12) | H | H | F | H |
| 470 | General Formula (12) | CN | General Formula (12) | General Formula (22) | General Formula (12) | H | H | H | H |
| 471 | General Formula (12) | CN | General Formula (12) | General Formula (22) | General Formula (12) | H | H | CH$_3$ | H |

TABLE 2-continued

| Compound No. | General Formula (1) | | | | | General Formula (12) | | | |
|---|---|---|---|---|---|---|---|---|---|
| | $R^1$ | $R^2$ | $R^3$ | $R^4$ | $R^5$ | $R^{31}, R^{38}$ | $R^{32}, R^{37}$ | $R^{33}, R^{36}$ | $R^{34}, R^{35}$ |
| 472 | General Formula (12) | CN | General Formula (12) | Formula (22) | General Formula (12) | H | H | CH$_3$O | H |
| 473 | General Formula (12) | CN | General Formula (12) | Formula (22) | General Formula (12) | H | H | t-C$_4$H$_9$ | H |
| 474 | General Formula (12) | CN | General Formula (12) | Formula (22) | General Formula (12) | H | H | Cl | H |
| 475 | General Formula (12) | CN | General Formula (12) | Formula (22) | General Formula (12) | H | H | F | H |
| 476 | General Formula (12) | CN | General Formula (12) | Formula (23) | General Formula (12) | H | H | H | H |
| 477 | General Formula (12) | CN | General Formula (12) | Formula (23) | General Formula (12) | H | H | CH$_3$ | H |
| 478 | General Formula (12) | CN | General Formula (12) | Formula (23) | General Formula (12) | H | H | CH$_3$O | H |
| 479 | General Formula (12) | CN | General Formula (12) | Formula (23) | General Formula (12) | H | H | t-C$_4$H$_9$ | H |
| 480 | General Formula (12) | CN | General Formula (12) | Formula (23) | General Formula (12) | H | H | Cl | H |
| 481 | General Formula (12) | CN | General Formula (12) | Formula (23) | General Formula (12) | H | H | F | H |
| 482 | General Formula (12) | CN | General Formula (12) | Formula (24) | General Formula (12) | H | H | H | H |
| 483 | General Formula (12) | CN | General Formula (12) | Formula (24) | General Formula (12) | H | H | CH$_3$ | H |
| 484 | General Formula (12) | CN | General Formula (12) | Formula (24) | General Formula (12) | H | H | CH$_3$O | H |
| 485 | General Formula (12) | CN | General Formula (12) | Formula (24) | General Formula (12) | H | H | t-C$_4$H$_9$ | H |
| 486 | General Formula (12) | CN | General Formula (12) | Formula (24) | General Formula (12) | H | H | Cl | H |
| 487 | General Formula (12) | CN | General Formula (12) | Formula (24) | General Formula (12) | H | H | F | H |
| 488 | General Formula (12) | CN | General Formula (12) | General Formula (12) | General Formula (12) | H | C$_6$H$_5$ | H | H |
| 489 | General Formula (12) | CN | General Formula (12) | General Formula (12) | General Formula (12) | H | H | C$_6$H$_5$ | H |
| 490 | General Formula (12) | CN | General Formula (12) | General Formula (12) | H | H | C$_6$H$_5$ | H | H |
| 491 | General Formula (12) | CN | General Formula (12) | General Formula (12) | H | H | H | C$_6$H$_5$ | H |
| 492 | General Formula (12) | CN | General Formula (12) | H | General Formula (12) | H | C$_6$H$_5$ | H | H |
| 493 | General Formula (12) | CN | General Formula (12) | H | General Formula (12) | H | H | C$_6$H$_5$ | H |
| 494 | General Formula (12) | CN | H | General Formula (12) | General Formula (12) | H | C$_6$H$_5$ | H | H |
| 495 | General Formula (12) | CN | H | General Formula (12) | General Formula (12) | H | H | C$_6$H$_5$ | H |
| 496 | H | CN | General Formula (12) | General Formula (12) | General Formula (12) | H | C$_6$H$_5$ | H | H |

TABLE 2-continued

| Compound No. | General Formula (1) | | | | | General Formula (12) | | | |
|---|---|---|---|---|---|---|---|---|---|
| | $R^1$ | $R^2$ | $R^3$ | $R^4$ | $R^5$ | $R^{31}, R^{38}$ | $R^{32}, R^{37}$ | $R^{33}, R^{36}$ | $R^{34}, R^{35}$ |
| 497 | H | CN | General Formula (12) | General Formula (12) | General Formula (12) | H | H | $C_6H_5$ | H |
| 498 | General Formula (12) | CN | General Formula (12) | H | H | H | $C_6H_5$ | H | H |
| 499 | General Formula (12) | CN | General Formula (12) | H | H | H | H | $C_6H_5$ | H |
| 500-1 | General Formula (12) | CN | H | General Formula (12) | H | H | $C_6H_5$ | H | H |
| 500-2 | General Formula (12) | CN | H | General Formula (12) | H | H | H | $C_6H_5$ | H |
| 500-3 | H | CN | General Formula (12) | General Formula (12) | H | H | $C_6H_5$ | H | H |
| 500-4 | H | CN | General Formula (12) | General Formula (12) | H | H | H | $C_6H_5$ | H |
| 500-5 | General Formula (12) | CN | H | H | General Formula (12) | H | $C_6H_5$ | H | H |
| 500-6 | General Formula (12) | CN | H | H | General Formula (12) | H | H | $C_6H_5$ | H |
| 500-7 | H | CN | General Formula (12) | H | General Formula (12) | H | $C_6H_5$ | H | H |
| 500-8 | H | CN | General Formula (12) | H | General Formula (12) | H | H | $C_6H_5$ | H |
| 500-9 | H | CN | H | General Formula (12) | General Formula (12) | H | $C_6H_5$ | H | H |
| 500-10 | H | CN | H | General Formula (12) | General Formula (12) | H | H | $C_6H_5$ | H |
| 500-11 | General Formula (12) | CN | H | H | H | H | $C_6H_5$ | H | H |
| 500-12 | General Formula (12) | CN | H | H | H | H | H | $C_6H_5$ | H |
| 500-13 | H | CN | General Formula (12) | H | H | H | $C_6H_5$ | H | H |
| 500-14 | H | CN | General Formula (12) | H | H | H | H | $C_6H_5$ | H |
| 500-15 | H | CN | H | General Formula (12) | H | H | $C_6H_5$ | H | H |
| 500-16 | H | CN | H | General Formula (12) | H | H | H | $C_6H_5$ | H |
| 500-17 | General Formula (12) | CN | General Formula (12) | General Formula (12) | F | H | H | $C_6H_5$ | H |
| 500-18 | General Formula (12) | CN | General Formula (12) | F | General Formula (12) | H | H | $C_6H_5$ | H |
| 500-19 | General Formula (12) | CN | F | General Formula (12) | General Formula (12) | H | H | $C_6H_5$ | H |
| 500-20 | F | CN | General Formula (12) | General Formula (12) | General Formula (12) | H | H | $C_6H_5$ | H |
| 500-21 | General Formula (12) | CN | General Formula (12) | F | F | H | H | $C_6H_5$ | H |
| 500-22 | General Formula (12) | CN | F | General Formula (12) | F | H | H | $C_6H_5$ | H |

TABLE 2-continued

| Compound No. | General Formula (1) R¹ | R² | R³ | R⁴ | R⁵ | General Formula (12) R³¹, R³⁸ | R³², R³⁷ | R³³, R³⁶ | R³⁴, R³⁵ |
|---|---|---|---|---|---|---|---|---|---|
| 500-23 | F | CN | General Formula (12) | General Formula (12) | F | H | H | $C_6H_5$ | H |
| 500-24 | General Formula (12) | CN | F | F | General Formula (12) | H | H | $C_6H_5$ | H |
| 500-25 | F | CN | General Formula (12) | F | General Formula (12) | H | H | $C_6H_5$ | H |
| 500-26 | F | CN | F | General Formula (12) | General Formula (12) | H | H | $C_6H_5$ | H |
| 500-27 | General Formula (12) | CN | F | F | F | H | H | $C_6H_5$ | H |
| 500-28 | F | CN | General Formula (12) | F | F | H | H | $C_6H_5$ | H |
| 500-29 | F | CN | F | General Formula (12) | F | H | H | $C_6H_5$ | H |
| 500-30 | General Formula (12) | CN | General Formula (12) | General Formula (12) | OH | H | H | $C_6H_5$ | H |
| 500-31 | General Formula (12) | CN | General Formula (12) | OH | General Formula (12) | H | H | $C_6H_5$ | H |
| 500-32 | General Formula (12) | CN | OH | General Formula (12) | General Formula (12) | H | H | $C_6H_5$ | H |
| 500-33 | OH | CN | General Formula (12) | General Formula (12) | General Formula (12) | H | H | $C_6H_5$ | H |
| 500-34 | General Formula (12) | CN | General Formula (12) | OH | OH | H | H | $C_6H_5$ | H |
| 500-35 | General Formula (12) | CN | OH | General Formula (12) | OH | H | H | $C_6H_5$ | H |
| 500-36 | OH | CN | General Formula (12) | General Formula (12) | OH | H | H | $C_6H_5$ | H |
| 500-37 | General Formula (12) | CN | OH | OH | General Formula (12) | H | H | $C_6H_5$ | H |
| 500-38 | OH | CN | General Formula (12) | OH | General Formula (12) | H | H | $C_6H_5$ | H |
| 500-39 | OH | CN | OH | General Formula (12) | General Formula (12) | H | H | $C_6H_5$ | H |
| 500-40 | General Formula (12) | CN | OH | OH | OH | H | H | $C_6H_5$ | H |
| 500-41 | OH | CN | General Formula (12) | OH | OH | H | H | $C_6H_5$ | H |
| 500-42 | OH | CN | OH | General Formula (12) | OH | H | H | $C_6H_5$ | H |
| 500-43 | OH | CN | OH | OH | General Formula (12) | H | H | $C_6H_5$ | H |
| 500-44 | General Formula (12) | CN | General Formula (12) | Cl | General Formula (12) | H | H | $C_6H_5$ | H |
| 500-45 | General Formula (12) | CN | General Formula (12) | F | General Formula (12) | H | H | $C_6H_5$ | H |
| 500-46 | General Formula (12) | CN | General Formula (12) | $CH_3O$ | General Formula (12) | H | H | $C_6H_5$ | H |
| 500-47 | General Formula (12) | CN | General Formula (12) | $C_2H_5O$ | General Formula (12) | H | H | $C_6H_5$ | H |

TABLE 2-continued

| Compound No. | General Formula (1) R¹ | R² | R³ | R⁴ | R⁵ | General Formula (12) $R^{31}, R^{38}$ | $R^{32}, R^{37}$ | $R^{33}, R^{36}$ | $R^{34}, R^{35}$ |
|---|---|---|---|---|---|---|---|---|---|
| 500-48 | General Formula (12) | CN | General Formula (12) | $C_6H_5O$ | General Formula (12) | H | H | $C_6H_5$ | H |
| 500-49 | General Formula (12) | CN | General Formula (12) | General Formula (21) | General Formula (12) | H | H | $C_6H_5$ | H |
| 500-50 | General Formula (12) | CN | General Formula (12) | General Formula (22) | General Formula (12) | H | H | $C_6H_5$ | H |
| 500-51 | General Formula (12) | CN | General Formula (12) | General Formula (23) | General Formula (12) | H | H | $C_6H_5$ | H |
| 500-52 | General Formula (12) | CN | General Formula (12) | General Formula (24) | General Formula (12) | H | H | $C_6H_5$ | H |

TABLE 3

| Compound No. | General Formula (1) R¹ | R² | R³ | R⁴ | R⁵ | General Formula (12) $R^{31}, R^{38}$ | $R^{32}, R^{37}$ | $R^{35}, R^{36}$ | $R^{32}, R^{35}$ |
|---|---|---|---|---|---|---|---|---|---|
| 501 | CN | General Formula (12) | General Formula (12) | General Formula (12) | General Formula (12) | H | H | H | H |
| 502 | CN | General Formula (12) | General Formula (12) | General Formula (12) | General Formula (12) | H | $CH_3$ | H | H |
| 503 | CN | General Formula (12) | General Formula (12) | General Formula (12) | General Formula (12) | H | $CH_3O$ | H | H |
| 504 | CN | General Formula (12) | General Formula (12) | General Formula (12) | General Formula (12) | H | H | $CH_3$ | H |
| 505 | CN | General Formula (12) | General Formula (12) | General Formula (12) | General Formula (12) | H | H | $CH_3O$ | H |
| 506 | CN | General Formula (12) | General Formula (12) | General Formula (12) | General Formula (12) | H | H | $t\text{-}C_4H_9$ | H |
| 507 | CN | General Formula (12) | General Formula (12) | General Formula (12) | General Formula (12) | H | H | Cl | H |
| 508 | CN | General Formula (12) | General Formula (12) | General Formula (12) | General Formula (12) | H | H | F | H |
| 509 | CN | General Formula (12) | General Formula (12) | General Formula (12) | General Formula (12) | H | H | H | $CH_3$ |
| 510 | CN | General Formula (12) | General Formula (12) | General Formula (12) | General Formula (12) | H | H | H | $CH_3O$ |
| 511 | CN | General Formula (12) | General Formula (12) | General Formula (12) | H | H | H | H | H |
| 512 | CN | General Formula (12) | General Formula (12) | General Formula (12) | H | H | H | $CH_3$ | H |
| 513 | CN | General Formula (12) | General Formula (12) | General Formula (12) | H | H | H | $CH_3O$ | H |
| 514 | CN | General Formula (12) | General Formula (12) | H | General Formula (12) | H | H | H | H |
| 515 | CN | General Formula (12) | General Formula (12) | H | General Formula (12) | H | H | $CH_3$ | H |
| 516 | CN | General Formula (12) | General Formula (12) | H | General Formula (12) | H | H | $CH_3O$ | H |
| 517 | CN | General Formula (12) | General Formula (12) | H | H | H | H | H | H |

TABLE 3-continued

| Compound No. | General Formula (1) | | | | | General Formula (12) | | | |
|---|---|---|---|---|---|---|---|---|---|
| | $R^1$ | $R^2$ | $R^3$ | $R^4$ | $R^5$ | $R^{31}, R^{38}$ | $R^{32}, R^{37}$ | $R^{35}, R^{36}$ | $R^{32}, R^{35}$ |
| 518 | CN | General Formula (12) | General Formula (12) | H | H | H | H | $CH_3$ | H |
| 519 | CN | General Formula (12) | General Formula (12) | H | H | H | H | $CH_3O$ | H |
| 520 | CN | General Formula (12) | H | General Formula (12) | H | H | H | H | H |
| 521 | CN | General Formula (12) | H | General Formula (12) | H | H | H | $CH_3$ | H |
| 522 | CN | General Formula (12) | H | General Formula (12) | H | H | H | $CH_3O$ | H |
| 523 | CN | H | General Formula (12) | General Formula (12) | H | H | H | H | H |
| 524 | CN | H | General Formula (12) | General Formula (12) | H | H | H | $CH_3$ | H |
| 525 | CN | H | General Formula (12) | General Formula (12) | H | H | H | $CH_3O$ | H |
| 526 | CN | General Formula (12) | H | H | General Formula (12) | H | H | H | H |
| 527 | CN | General Formula (12) | H | H | General Formula (12) | H | H | $CH_3$ | H |
| 528 | CN | General Formula (12) | H | H | General Formula (12) | H | H | $CH_3O$ | H |
| 529 | CN | General Formula (12) | H | H | H | H | H | H | H |
| 530 | CN | General Formula (12) | H | H | H | H | H | $CH_3$ | H |
| 531 | CN | General Formula (12) | H | H | H | H | H | $CH_3O$ | H |
| 532 | CN | H | General Formula (12) | H | H | H | H | H | H |
| 533 | CN | H | General Formula (12) | H | H | H | H | $CH_3$ | H |
| 534 | CN | H | General Formula (12) | H | H | H | H | $CH_3O$ | H |
| 535 | CN | General Formula (12) | General Formula (12) | General Formula (12) | F | H | H | H | H |
| 536 | CN | General Formula (12) | General Formula (12) | General Formula (12) | F | H | H | $CH_3$ | H |
| 537 | CN | General Formula (12) | General Formula (12) | General Formula (12) | F | H | H | $CH_3O$ | H |
| 538 | CN | General Formula (12) | General Formula (12) | F | General Formula (12) | H | H | H | H |
| 539 | CN | General Formula (12) | General Formula (12) | F | General Formula (12) | H | H | $CH_3$ | H |
| 540 | CN | General Formula (12) | General Formula (12) | F | General Formula (12) | H | H | $CH_3O$ | H |
| 541 | CN | General Formula (12) | General Formula (12) | F | F | H | H | H | H |
| 542 | CN | General Formula (12) | General Formula (12) | F | F | H | H | $CH_3$ | H |

TABLE 3-continued

| Compound No. | General Formula (1) | | | | | General Formula (12) | | | |
|---|---|---|---|---|---|---|---|---|---|
| | $R^1$ | $R^2$ | $R^3$ | $R^4$ | $R^5$ | $R^{31}, R^{38}$ | $R^{32}, R^{37}$ | $R^{35}, R^{36}$ | $R^{32}, R^{35}$ |
| 543 | CN | General Formula (12) | General Formula (12) | F | F | H | H | CH$_3$O | H |
| 544 | CN | General Formula (12) | F | General Formula (12) | F | H | H | H | H |
| 545 | CN | General Formula (12) | F | General Formula (12) | F | H | H | CH$_3$ | H |
| 546 | CN | General Formula (12) | F | General Formula (12) | F | H | H | CH$_3$O | H |
| 547 | CN | F | General Formula (12) | General Formula (12) | F | H | H | H | H |
| 548 | CN | F | General Formula (12) | General Formula (12) | F | H | H | CH$_3$ | H |
| 549 | CH | F | General Formula (12) | General Formula (12) | F | H | H | CH$_3$O | H |
| 550 | CN | General Formula (12) | F | F | General Formula (12) | H | H | H | H |
| 551 | CN | General Formula (12) | F | F | General Formula (12) | H | H | CH$_3$ | H |
| 552 | CN | General Formula (12) | F | F | General Formula (12) | H | H | CH$_3$O | H |
| 553 | CN | General Formula (12) | F | F | F | H | H | H | H |
| 554 | CN | General Formula (12) | F | F | F | H | H | CH$_3$ | H |
| 555 | CN | General Formula (12) | F | F | F | H | H | CH$_3$O | H |
| 556 | CN | F | General Formula (12) | F | F | H | H | H | H |
| 557 | CN | F | General Formula (12) | F | F | H | H | CH$_3$ | H |
| 558 | CN | F | General Formula (12) | F | F | H | H | CH$_3$O | H |
| 559 | CN | General Formula (12) | General Formula (12) | General Formula (12) | OH | H | H | H | H |
| 560 | CN | General Formula (12) | General Formula (12) | General Formula (12) | OH | H | H | CH$_3$ | H |
| 561 | CN | General Formula (12) | General Formula (12) | General Formula (12) | OH | H | H | CH$_3$O | H |
| 562 | CN | General Formula (12) | General Formula (12) | OH | General Formula (12) | H | H | H | H |
| 563 | CN | General Formula (12) | General Formula (12) | OH | General Formula (12) | H | H | CH$_3$ | H |
| 654 | CN | General Formula (12) | General Formula (12) | OH | General Formula (12) | H | H | CH$_3$O | H |
| 565 | CN | General Formula (12) | General Formula (12) | OH | General Formula (12) | H | H | Cl | H |
| 566 | CN | General Formula (12) | General Formula (12) | OH | General Formula (12) | H | H | F | H |
| 567 | CN | General Formula (12) | General Formula (12) | OH | OH | H | H | H | H |

TABLE 3-continued

| Compound No. | General Formula (1) | | | | | General Formula (12) | | | |
|---|---|---|---|---|---|---|---|---|---|
| | $R^1$ | $R^2$ | $R^3$ | $R^4$ | $R^5$ | $R^{31}, R^{38}$ | $R^{32}, R^{37}$ | $R^{35}, R^{36}$ | $R^{32}, R^{35}$ |
| 568 | CN | General Formula (12) | General Formula (12) | OH | OH | H | H | $CH_3$ | H |
| 569 | CN | General Formula (12) | General Formula (12) | OH | OH | H | H | $CH_3O$ | H |
| 570 | CN | General Formula (12) | OH | General Formula (12) | OH | H | H | H | H |
| 571 | CN | General Formula (12) | OH | General Formula (12) | OH | H | H | $CH_3$ | H |
| 572 | CN | General Formula (12) | OH | General Formula (12) | OH | H | H | $CH_3O$ | H |
| 573 | CN | OH | General Formula (12) | General Formula (12) | OH | H | H | H | H |
| 574 | CN | OH | General Formula (12) | General Formula (12) | OH | H | H | $CH_3$ | H |
| 575 | CN | OH | General Formula (12) | General Formula (12) | OH | H | H | $CH_3O$ | H |
| 576 | CN | General Formula (12) | OH | OH | General Formula (12) | H | H | H | H |
| 577 | CN | General Formula (12) | OH | OH | General Formula (12) | H | H | $CH_3$ | H |
| 578 | CN | General Formula (12) | OH | OH | General Formula (12) | H | H | $CH_3O$ | H |
| 579 | CN | General Formula (12) | OH | OH | OH | H | H | H | H |
| 580 | CN | General Formula (12) | OH | OH | OH | H | H | $CH_3$ | H |
| 581 | CN | General Formula (12) | OH | OH | OH | H | H | $CH_3O$ | H |
| 582 | CN | OH | General Formula (12) | OH | OH | H | H | H | H |
| 583 | CN | OH | General Formula (12) | OH | OH | H | H | $CH_3$ | H |
| 584 | CN | OH | General Formula (12) | OH | OH | H | H | $CH_3O$ | H |
| 585 | CN | General Formula (12) | General Formula (12) | Cl | General Formula (12) | H | H | H | H |
| 586 | CN | General Formula (12) | General Formula (12) | Cl | General Formula (12) | H | H | $CH_3$ | H |
| 587 | CN | General Formula (12) | General Formula (12) | Cl | General Formula (12) | H | H | $CH_3O$ | H |
| 588 | CN | General Formula (12) | General Formula (12) | Cl | General Formula (12) | H | H | $t\text{-}C_4H_9$ | H |
| 589 | CN | General Formula (12) | General Formula (12) | Cl | General Formula (12) | H | H | Cl | H |
| 590 | CN | General Formula (12) | General Formula (12) | Cl | General Formula (12) | H | H | F | H |
| 591 | CN | General Formula (12) | General Formula (12) | F | General Formula (12) | H | H | H | H |
| 592 | CN | General Formula (12) | General Formula (12) | F | General Formula (12) | H | H | $CH_3$ | H |

TABLE 3-continued

| Compound No. | _____General Formula (1)_____ | | | | | _____General Formula (12)_____ | | | |
|---|---|---|---|---|---|---|---|---|---|
| | $R^1$ | $R^2$ | $R^3$ | $R^4$ | $R^5$ | $R^{31}, R^{38}$ | $R^{32}, R^{37}$ | $R^{35}, R^{36}$ | $R^{32}, R^{35}$ |
| 593 | CN | General Formula (12) | General Formula (12) | F | General Formula (12) | H | H | $CH_3O$ | H |
| 594 | CN | General Formula (12) | General Formula (12) | F | General Formula (12) | H | H | $t\text{-}C_4H_9$ | H |
| 595 | CN | General Formula (12) | General Formula (12) | F | General Formula (12) | H | H | Cl | H |
| 596 | CN | General Formula (12) | General Formula (12) | F | General Formula (12) | H | H | F | H |
| 597 | CN | General Formula (12) | General Formula (12) | $CH_3O$ | General Formula (12) | H | H | H | H |
| 598 | CN | General Formula (12) | General Formula (12) | $CH_3O$ | General Formula (12) | H | H | $CH_3$ | H |
| 599 | CN | General Formula (12) | General Formula (12) | $CH_3O$ | General Formula (12) | H | H | $CH_3O$ | H |
| 600 | CN | General Formula (12) | General Formula (12) | $CH_3O$ | General Formula (12) | H | H | $t\text{-}C_4H_9$ | H |
| 601 | CN | General Formula (12) | General Formula (12) | $CH_3O$ | General Formula (12) | H | H | Cl | H |
| 602 | CN | General Formula (12) | General Formula (12) | $CH_3O$ | General Formula (12) | H | H | F | H |
| 603 | CN | General Formula (12) | General Formula (12) | $C_2H_5O$ | General Formula (12) | H | H | H | H |
| 604 | CN | General Formula (12) | General Formula (12) | $C_2H_5O$ | General Formula (12) | H | H | $CH_3$ | H |
| 605 | CN | General Formula (12) | General Formula (12) | $C_2H_5O$ | General Formula (12) | H | H | $CH_3O$ | H |
| 606 | CN | General Formula (12) | General Formula (12) | $C_2H_5O$ | General Formula (12) | H | H | $t\text{-}C_4H_9$ | H |
| 607 | CN | General Formula (12) | General Formula (12) | $C_2H_5O$ | General Formula (12) | H | H | Cl | H |
| 608 | CN | General Formula (12) | General Formula (12) | $C_2H_5O$ | General Formula (12) | H | H | F | H |
| 609 | CN | General Formula (12) | General Formula (12) | $C_6H_5O$ | General Formula (12) | H | H | H | H |
| 610 | CN | General Formula (12) | General Formula (12) | $C_6H_5O$ | General Formula (12) | H | H | $CH_3$ | H |
| 611 | CN | General Formula (12) | General Formula (12) | $C_6H_5O$ | General Formula (12) | H | H | $CH_3O$ | H |
| 612 | CN | General Formula (12) | General Formula (12) | $C_6H_5O$ | General Formula (12) | H | H | $t\text{-}C_4H_9$ | H |
| 613 | CN | General Formula (12) | General Formula (12) | $C_6H_5O$ | General Formula (12) | H | H | Cl | H |
| 614 | CN | General Formula (12) | General Formula (12) | $C_6H_5O$ | General Formula (12) | H | H | F | H |
| 615 | CN | General Formula (12) | General Formula (12) | General Formula (21) | General Formula (12) | H | H | H | H |
| 616 | CN | General Formula (12) | General Formula (12) | General Formula (21) | General Formula (12) | H | H | $CH_3$ | H |
| 617 | CN | General Formula (12) | General Formula (12) | General Formula (21) | General Formula (12) | H | H | $CH_3O$ | H |

TABLE 3-continued

| Compound No. | General Formula (1) | | | | | General Formula (12) | | | |
|---|---|---|---|---|---|---|---|---|---|
| | R¹ | R² | R³ | R⁴ | R⁵ | R³¹, R³⁸ | R³², R³⁷ | R³⁵, R³⁶ | R³², R³⁵ |
| 618 | CN | General Formula (12) | General Formula (21) | Formula | General Formula (12) | H | H | t-C₆H₉ | H |
| 619 | CN | General Formula (12) | General Formula (21) | Formula | General Formula (12) | H | H | Cl | H |
| 620 | CN | General Formula (12) | General Formula (21) | Formula | General Formula (12) | H | H | F | H |
| 621 | CN | General Formula (12) | General Formula (22) | Formula | General Formula (12) | H | H | H | H |
| 622 | CN | General Formula (12) | General Formula (22) | Formula | General Formula (12) | H | H | CH₃ | H |
| 623 | CN | General Formula (12) | General Formula (22) | Formula | General Formula (12) | H | H | CH₃O | H |
| 624 | CN | General Formula (12) | General Formula (22) | Formula | General Formula (12) | H | H | t-C₄H₉ | H |
| 625 | CN | General Formula (12) | General Formula (22) | Formula | General Formula (12) | H | H | Cl | H |
| 626 | CN | General Formula (12) | General Formula (22) | Formula | General Formula (12) | H | H | F | H |
| 627 | CN | General Formula (12) | General Formula (23) | Formula | General Formula (12) | H | H | H | H |
| 628 | CN | General Formula (12) | General Formula (23) | Formula | General Formula (12) | H | H | CH₃ | H |
| 629 | CN | General Formula (12) | General Formula (23) | Formula | General Formula (12) | H | H | CH₃O | H |
| 630 | CN | General Formula (12) | General Formula (23) | Formula | General Formula (12) | H | H | t-C₄H₉ | H |
| 631 | CN | General Formula (12) | General Formula (23) | Formula | General Formula (12) | H | H | Cl | H |
| 632 | CN | General Formula (12) | General Formula (23) | Formula | General Formula (12) | H | H | F | H |
| 633 | CN | General Formula (12) | General Formula (24) | Formula | General Formula (12) | H | H | H | H |
| 634 | CN | General Formula (12) | General Formula (24) | Formula | General Formula (12) | H | H | CH₃ | H |
| 635 | CN | General Formula (12) | General Formula (24) | Formula | General Formula (12) | H | H | CH₃O | H |
| 636 | CN | General Formula (12) | General Formula (24) | Formula | General Formula (12) | H | H | t-C₄H₉ | H |
| 637 | CN | General Formula (12) | General Formula (24) | Formula | General Formula (12) | H | H | Cl | H |
| 638 | CN | General Formula (12) | General Formula (24) | Formula | General Formula (12) | H | H | F | H |
| 639 | CN | General Formula (12) | General Formula (12) | General Formula (12) | General Formula (12) | H | C₆H₅ | H | H |
| 640 | CN | General Formula (12) | General Formula (12) | General Formula (12) | General Formula (12) | H | H | C₆H₅ | H |
| 641 | CN | General Formula (12) | General Formula (12) | General Formula (12) | H | H | C₆H₅ | H | H |
| 642 | CN | General Formula (12) | General Formula (12) | General Formula (12) | H | H | H | C₆H₅ | H |

TABLE 3-continued

| Compound No. | General Formula (1) | | | | | General Formula (12) | | | |
|---|---|---|---|---|---|---|---|---|---|
| | $R^1$ | $R^2$ | $R^3$ | $R^4$ | $R^5$ | $R^{31}, R^{38}$ | $R^{32}, R^{37}$ | $R^{35}, R^{36}$ | $R^{32}, R^{35}$ |
| 643 | CN | General Formula (12) | General Formula (12) | H | General Formula (12) | H | $C_6H_5$ | H | H |
| 644 | CN | General Formula (12) | General Formula (12) | H | General Formula (12) | H | H | $C_6H_5$ | H |
| 645 | CN | General Formula (12) | General Formula (12) | H | H | H | $C_6H_5$ | H | H |
| 646 | CN | General Formula (12) | General Formula (12) | H | H | H | H | $C_6H_5$ | H |
| 647 | CN | General Formula (12) | H | General Formula (12) | H | H | $C_6H_5$ | H | H |
| 648 | CN | General Formula (12) | H | General Formula (12) | H | H | H | $C_6H_5$ | H |
| 649 | CN | H | General Formula (12) | General Formula (12) | H | H | $C_6H_5$ | H | H |
| 650 | CN | H | General Formula (12) | General Formula (12) | H | H | H | $C_6H_5$ | H |
| 651 | CN | H | H | General Formula (12) | General Formula (12) | H | $C_6H_5$ | H | H |
| 652 | CN | H | H | General Formula (12) | General Formula (12) | H | H | $C_6H_5$ | H |
| 653 | CN | General Formula (12) | H | H | H | H | $C_6H_5$ | H | H |
| 654 | CN | General Formula (12) | H | H | H | H | H | $C_6H_5$ | H |
| 655 | CN | H | General Formula (12) | H | H | H | $C_6H_5$ | H | H |
| 656 | CN | H | General Formula (12) | H | H | H | H | $C_6H_5$ | H |
| 657 | CN | General Formula (12) | General Formula (12) | General Formula (12) | F | H | H | $C_6H_5$ | H |
| 658 | CN | General Formula (12) | General Formula (12) | F | General Formula (12) | H | H | $C_6H_5$ | H |
| 659 | CN | General Formula (12) | General Formula (12) | F | F | H | H | $C_6H_5$ | H |
| 660 | CN | General Formula (12) | F | General Formula (12) | F | H | H | $C_6H_5$ | H |
| 661 | CN | F | General Formula (12) | General Formula (12) | F | H | H | $C_6H_5$ | H |
| 662 | CN | F | F | General Formula (12) | General Formula (12) | H | H | $C_6H_5$ | H |
| 663 | CN | General Formula (12) | F | F | F | H | H | $C_6H_5$ | H |
| 664 | CN | F | General Formula (12) | F | F | H | H | $C_6H_5$ | H |
| 665 | CN | General Formula (12) | General Formula (12) | General Formula (12) | OH | H | H | $C_6H_5$ | H |
| 666 | CN | General Formula (12) | General Formula (12) | OH | General Formula (12) | H | H | $C_6H_5$ | H |
| 667 | CN | General Formula (12) | General Formula (12) | OH | OH | H | H | $C_6H_5$ | H |

TABLE 3-continued

| Compound No. | General Formula (1) | | | | | General Formula (12) | | | | |
|---|---|---|---|---|---|---|---|---|---|---|
| | $R^1$ | $R^2$ | $R^3$ | $R^4$ | $R^5$ | $R^{31}, R^{38}$ | $R^{32}, R^{37}$ | $R^{35}, R^{36}$ | $R^{32}, R^{35}$ | |
| 668 | CN | General Formula (12) | OH | General Formula (12) | OH | H | H | $C_6H_5$ | H | |
| 669 | CN | OH | General Formula (12) | General Formula (12) | OH | H | H | $C_6H_5$ | H | |
| 670 | CN | OH | OH | General Formula (12) | General Formula (12) | H | H | $C_6H_5$ | H | |
| 671 | CN | General Formula (12) | OH | OH | OH | H | H | $C_6H_5$ | H | |
| 672 | CN | OH | General Formula (12) | OH | OH | H | H | $C_6H_5$ | H | |
| 673 | CN | General Formula (12) | General Formula (12) | Cl | General Formula (12) | H | H | $C_6H_5$ | H | |
| 674 | CN | General Formula (12) | General Formula (12) | F | General Formula (12) | H | H | $C_6H_5$ | H | |
| 675 | CN | General Formula (12) | General Formula (12) | $CH_3O$ | General Formula (12) | H | H | $C_6H_5$ | H | |
| 676 | CN | General Formula (12) | General Formula (12) | $C_2H_5O$ | General Formula (12) | H | H | $C_6H_5$ | H | |
| 677 | CN | General Formula (12) | General Formula (12) | $C_6H_5O$ | General Formula (12) | H | H | $C_6H_5$ | H | |
| 678 | CN | General Formula (12) | General Formula (12) | Formula (21) | General Formula (12) | H | H | $C_6H_5$ | H | |
| 679 | CN | General Formula (12) | General Formula (12) | Formula (22) | General Formula (12) | H | H | $C_6H_5$ | H | |
| 680 | CN | General Formula (12) | General Formula (12) | Formula (23) | General Formula (12) | H | h | $C_6H_5$ | H | |
| 681 | CN | General Formula (12) | General Formula (12) | Formula (24) | General Formula (12) | H | H | $C_6H_5$ | H | |

TABLE 4

| Compound No. | General Formula (1) | | | | | General Formula (13) | | | | | |
|---|---|---|---|---|---|---|---|---|---|---|---|
| | $R^1$ | $R^2$ | $R^3$ | $R^4$ | $R^5$ | $R^{41}$ | $R^{42}$ | $R^{43}$ | $R^{44}$ | $R^{45}$ | $R^{46}$ |
| 701 | General Formula (13) | General Formula (13) | CN | General Formula (13) | General Formula (13) | H | H | H | H | H | H |
| 702 | General Formula (13) | General Formula (13) | CN | General Formula (13) | General Formula (13) | H | $CH_3$ | H | H | H | H |
| 703 | General Formula (13) | General Formula (13) | CN | General Formula (13) | General Formula (13) | H | $CH_3O$ | H | H | H | H |
| 704 | General Formula (13) | General Formula (13) | CN | General Formula (13) | General Formula (13) | H | H | $CH_3$ | H | H | H |
| 705 | General Formula (13) | General Formula (13) | CN | General Formula (13) | General Formula (13) | H | H | $CH_3O$ | H | H | H |
| 706 | General Formula (13) | General Formula (13) | CN | General Formula (13) | General Formula (13) | H | H | $t-C_4H_9$ | H | H | H |
| 707 | General Formula (13) | General Formula (13) | CN | General Formula (13) | General Formula (13) | H | H | Cl | H | H | H |
| 708 | General Formula (13) | General Formula (13) | CN | General Formula (13) | General Formula (13) | H | H | F | H | H | H |

TABLE 4-continued

| Compound No. | General Formula (1) | | | | | General Formula (13) | | | | | |
|---|---|---|---|---|---|---|---|---|---|---|---|
| | $R^1$ | $R^2$ | $R^3$ | $R^4$ | $R^5$ | $R^{41}$ | $R^{42}$ | $R^{43}$ | $R^{44}$ | $R^{45}$ | $R^{46}$ |
| 709 | General Formula (13) | General Formula (13) | CN | General Formula (13) | General Formula (13) | H | H | H | $CH_3$ | H | H |
| 710 | General Formula (13) | General Formula (13) | CN | General Formula (13) | General Formula (13) | H | H | H | $CH_3O$ | H | H |
| 711 | General Formula (13) | General Formula (13) | CN | General Formula (13) | General Formula (13) | H | H | H | H | $CH_3$ | H |
| 712 | General Formula (13) | General Formula (13) | CN | General Formula (13) | General Formula (13) | H | H | H | H | $CH_3O$ | H |
| 713 | General Formula (13) | General Formula (13) | CN | General Formula (13) | General Formula (13) | H | H | H | H | $t\text{-}C_4H_9$ | H |
| 714 | General Formula (13) | General Formula (13) | CN | General Formula (13) | General Formula (13) | H | H | H | H | Cl | H |
| 715 | General Formula (13) | General Formula (13) | CN | General Formula (13) | General Formula (13) | H | H | H | H | F | H |
| 716 | General Formula (13) | General Formula (13) | CN | General Formula (13) | General Formula (13) | H | H | H | H | $C_6H_5$ | H |
| 717 | General Formula (13) | General Formula (13) | CN | General Formula (13) | General Formula (13) | H | H | H | H | $p\text{-}CH_3C_6H_4$ | H |
| 718 | General Formula (13) | General Formula (13) | CN | General Formula (13) | General Formula (13) | H | H | H | H | $2,4,6\text{-}(CH_3)_3C_6H_2$ | H |
| 719 | General Formula (13) | General Formula (13) | CN | General Formula (13) | General Formula (13) | H | H | H | H | $p\text{-}CH_3OC_6H_4$ | H |
| 720 | General Formula (13) | General Formula (13) | CN | General Formula (13) | General Formula (13) | H | H | H | H | $p\text{-}(CH_3)_2NC_6H_4$ | H |
| 721 | General Formula (13) | General Formula (13) | CN | General Formula (13) | General Formula (13) | H | H | H | H | $p\text{-}FC_6H_4$ | H |
| 722 | General Formula (13) | General Formula (13) | CN | General Formula (13) | General Formula (13) | H | H | H | H | $p\text{-}CNC_6H_4$ | H |
| 723 | General Formula (13) | General Formula (13) | CN | General Formula (13) | General Formula (13) | H | H | H | H | H | $CH_3$ |
| 724 | General Formula (13) | General Formula (13) | CN | General Formula (13) | General Formula (13) | H | H | H | H | H | $CH_3O$ |
| 725 | General Formula (13) | General Formula (13) | CN | General Formula (13) | General Formula (13) | H | H | H | H | H | $t\text{-}C_4H_9$ |
| 726 | General Formula (13) | General Formula (13) | CN | General Formula (13) | General Formula (13) | H | H | H | H | H | Cl |
| 727 | General Formula (13) | General Formula (13) | CN | General Formula (13) | General Formula (13) | H | H | H | H | H | F |
| 728 | General Formula (13) | General Formula (13) | CN | General Formula (13) | General Formula (13) | H | H | H | H | H | $C_6H_5$ |
| 729 | General Formula (13) | General Formula (13) | CN | General Formula (13) | General Formula (13) | H | H | H | H | H | $p\text{-}CH_3C_6H_4$ |
| 730 | General Formula (13) | General Formula (13) | CN | General Formula (13) | General Formula (13) | H | H | H | H | H | $2,4,6\text{-}(CH_3)_3C_6H_2$ |
| 731 | General Formula (13) | General Formula (13) | CN | General Formula (13) | General Formula (13) | H | H | H | H | H | $p\text{-}CH_3OC_6H_4$ |
| 732 | General Formula (13) | General Formula (13) | CN | General Formula (13) | General Formula (13) | H | H | H | H | H | $p\text{-}(CH_3)_2NC_6H_4$ |
| 733 | General Formula (13) | General Formula (13) | CN | General Formula (13) | General Formula (13) | H | H | H | H | H | $p\text{-}FC_6H_4$ |

TABLE 4-continued

| Compound No. | General Formula (1) | | | | | General Formula (13) | | | | | |
|---|---|---|---|---|---|---|---|---|---|---|---|
| | $R^1$ | $R^2$ | $R^3$ | $R^4$ | $R^5$ | $R^{41}$ | $R^{42}$ | $R^{43}$ | $R^{44}$ | $R^{45}$ | $R^{46}$ |
| 734 | General Formula (13) | General Formula (13) | CN | General Formula (13) | General Formula (13) | H | H | H | H | H | p-CNC$_6$H$_4$ |
| 735 | General Formula (13) | General Formula (13) | CN | General Formula (13) | H | H | H | H | H | H | H |
| 736 | General Formula (13) | General Formula (13) | CN | H | General Formula (13) | H | H | H | H | H | H |
| 737 | General Formula (13) | General Formula (13) | CN | H | H | H | H | H | H | H | H |
| 738 | General Formula (13) | H | CN | General Formula (13) | H | H | H | H | H | H | H |
| 739 | H | General Formula (13) | CN | General Formula (13) | H | H | H | H | H | H | H |
| 740 | General Formula (13) | H | CN | H | H | H | H | H | H | H | H |
| 741 | General Formula (13) | General Formula (13) | CN | General Formula (13) | F | H | H | H | H | H | H |
| 742 | General Formula (13) | General Formula (13) | CN | F | General Formula (13) | H | H | H | H | H | H |
| 743 | General Formula (13) | General Formula (13) | CN | F | F | H | H | H | H | H | H |
| 744 | General Formula (13) | F | CN | General Formula (13) | F | H | H | H | H | H | H |
| 745 | F | General Formula (13) | CN | General Formula (13) | F | H | H | H | H | H | H |
| 746 | General Formula (13) | F | CN | F | F | H | H | H | H | H | H |
| 747 | General Formula (13) | General Formula (13) | CN | General Formula (13) | OH | H | H | H | H | H | H |
| 748 | General Formula (13) | General Formula (13) | CN | OH | General Formula (13) | H | H | H | H | H | H |
| 749 | General Formula (13) | General Formula (13) | CN | OH | OH | H | H | H | H | H | H |
| 750 | General Formula (13) | OH | CN | General Formula (13) | OH | H | H | H | H | H | H |
| 751 | OH | General Formula (13) | CN | General Formula (13) | OH | H | H | H | H | H | H |
| 752 | General Formula (13) | OH | CN | OH | OH | H | H | H | H | H | H |
| 753 | General Formula (13) | General Formula (13) | CN | Cl | General Formula (13) | H | H | H | H | H | H |
| 754 | General Formula (13) | General Formula (13) | CN | Cl | General Formula (13) | H | H | CH$_3$ | H | H | H |
| 755 | General Formula (13) | General Formula (13) | CN | Cl | General Formula (13) | H | H | CH$_3$O | H | H | H |
| 756 | General Formula (13) | General Formula (13) | CN | Cl | General Formula (13) | H | H | t-C$_4$H$_9$ | H | H | H |
| 757 | General Formula (13) | General Formula (13) | CN | Cl | General Formula (13) | H | H | Cl | H | H | H |
| 758 | General Formula (13) | General Formula (13) | CN | Cl | General Formula (13) | H | H | F | H | H | H |

TABLE 4-continued

| Compound No. | General Formula (1) | | | | | General Formula (13) | | | | | |
|---|---|---|---|---|---|---|---|---|---|---|---|
| | $R^1$ | $R^2$ | $R^3$ | $R^4$ | $R^5$ | $R^{41}$ | $R^{42}$ | $R^{43}$ | $R^{44}$ | $R^{45}$ | $R^{46}$ |
| 759 | General Formula (13) | General Formula (13) | CN | F | General Formula (13) | H | H | H | H | H | H |
| 760 | General Formula (13) | General Formula (13) | CN | F | General Formula (13) | H | H | $CH_3$ | H | H | H |
| 761 | General Formula (13) | General Formula (13) | CN | F | General Formula (13) | H | H | $CH_3O$ | H | H | H |
| 762 | General Formula (13) | General Formula (13) | CN | F | General Formula (13) | H | H | $t-C_4H_9$ | H | H | H |
| 763 | General Formula (13) | General Formula (13) | CN | F | General Formula (13) | H | H | Cl | H | H | H |
| 764 | General Formula (13) | General Formula (13) | CN | F | General Formula (13) | H | H | F | H | H | H |
| 765 | General Formula (13) | General Formula (13) | CN | $CH_3O$ | General Formula (13) | H | H | H | H | H | H |
| 766 | General Formula (13) | General Formula (13) | CN | $CH_3O$ | General Formula (13) | H | H | $CH_3$ | H | H | H |
| 767 | General Formula (13) | General Formula (13) | CN | $CH_3O$ | General Formula (13) | H | H | $CH_3O$ | H | H | H |
| 768 | General Formula (13) | General Formula (13) | CN | $CH_3O$ | General Formula (13) | H | H | $t-C_4H_9$ | H | H | H |
| 769 | General Formula (13) | General Formula (13) | CN | $CH_3O$ | General Formula (13) | H | H | Cl | H | H | H |
| 770 | General Formula (13) | General Formula (13) | CN | $CH_3O$ | General Formula (13) | H | H | F | H | H | H |
| 771 | General Formula (13) | General Formula (13) | CN | $C_2H_5O$ | General Formula (13) | H | H | H | H | H | H |
| 772 | General Formula (13) | General Formula (13) | CN | $C_2H_5O$ | General Formula (13) | H | H | $CH_3$ | H | H | H |
| 773 | General Formula (13) | General Formula (13) | CN | $C_2H_5O$ | General Formula (13) | H | H | $CH_3O$ | H | H | H |
| 774 | General Formula (13) | General Formula (13) | CN | $C_2H_5O$ | General Formula (13) | H | H | $t-C_4H_9$ | H | H | H |
| 775 | General Formula (13) | General Formula (13) | CN | $C_2H_5O$ | General Formula (13) | H | H | Cl | H | H | H |
| 776 | General Formula (13) | General Formula (13) | CN | $C_2H_5O$ | General Formula (13) | H | H | F | H | H | H |
| 777 | General Formula (13) | General Formula (13) | CN | $C_6H_5O$ | General Formula (13) | H | H | H | H | H | H |
| 778 | General Formula (13) | General Formula (13) | CN | $C_6H_5O$ | General Formula (13) | H | H | $CH_3$ | H | H | H |
| 779 | General Formula (13) | General Formula (13) | CN | $C_6H_5O$ | General Formula (13) | H | H | $CH_3O$ | H | H | H |
| 780 | General Formula (13) | General Formula (13) | CN | $C_6H_5O$ | General Formula (13) | H | H | $t-C_4H_9$ | H | H | H |
| 781 | General Formula (13) | General Formula (13) | CN | $C_6H_5O$ | General Formula (13) | H | H | Cl | H | H | H |
| 782 | General Formula (13) | General Formula (13) | CN | $C_6H_5O$ | General Formula (13) | H | H | F | H | H | H |
| 783 | General Formula (13) | General Formula (13) | CN | Formula (21) | General Formula (13) | H | H | H | H | H | H |

TABLE 4-continued

| Compound | General Formula (1) | | | | | General Formula (13) | | | | | |
|---|---|---|---|---|---|---|---|---|---|---|---|
| No. | $R^1$ | $R^2$ | $R^3$ | $R^4$ | $R^5$ | $R^{41}$ | $R^{42}$ | $R^{43}$ | $R^{44}$ | $R^{45}$ | $R^{46}$ |
| 784 | General Formula (13) | General Formula (13) | CN | Formula (21) | General Formula (13) | H | H | $CH_3$ | H | H | H |
| 785 | General Formula (13) | General Formula (13) | CN | Formula (21) | General Formula (13) | H | H | $CH_3O$ | H | H | H |
| 786 | General Formula (13) | General Formula (13) | CN | Formula (21) | General Formula (13) | H | H | $t$-$C_4H_9$ | H | H | H |
| 787 | General Formula (13) | General Formula (13) | CN | Formula (21) | General Formula (13) | H | H | Cl | H | H | H |
| 788 | General Formula (13) | General Formula (13) | CN | Formula (21) | General Formula (13) | H | H | F | H | H | H |
| 789 | General Formula (13) | General Formula (13) | CN | Formula (22) | General Formula (13) | H | H | H | H | H | H |
| 790 | General Formula (13) | General Formula (13) | CN | Formula (22) | General Formula (13) | H | H | $CH_3$ | H | H | H |
| 791 | General Formula (13) | General Formula (13) | CN | Formula (22) | General Formula (13) | H | H | $CH_3O$ | H | H | H |
| 792 | General Formula (13) | General Formula (13) | CN | Formula (22) | General Formula (13) | H | H | $t$-$C_4H_9$ | H | H | H |
| 793 | General Formula (13) | General Formula (13) | CN | Formula (22) | General Formula (13) | H | H | Cl | H | H | H |
| 794 | General Formula (13) | General Formula (13) | CN | Formula (22) | General Formula (13) | H | H | F | H | H | H |
| 795 | General Formula (13) | General Formula (13) | CN | Formula (23) | General Formula (13) | H | H | H | H | H | H |
| 796 | General Formula (13) | General Formula (13) | CN | Formula (23) | General Formula (13) | H | H | $CH_3$ | H | H | H |
| 797 | General Formula (13) | General Formula (13) | CN | Formula (23) | General Formula (13) | H | H | $CH_3O$ | H | H | H |
| 798 | General Formula (13) | General Formula (13) | CN | Formula (23) | General Formula (13) | H | H | $t$-$C_4H_9$ | H | H | H |
| 799 | General Formula (13) | General Formula (13) | CN | Formula (23) | General Formula (13) | H | H | Cl | H | H | H |
| 800 | General Formula (13) | General Formula (13) | CN | Formula (23) | General Formula (13) | H | H | F | H | H | H |
| 801 | General Formula (13) | General Formula (13) | CN | Formula (24) | General Formula (13) | H | H | H | H | H | H |
| 802 | General Formula (13) | General Formula (13) | CN | Formula (24) | General Formula (13) | H | H | $CH_3$ | H | H | H |
| 803 | General Formula (13) | General Formula (13) | CN | Formula (24) | General Formula (13) | H | H | $CH_3O$ | H | H | H |
| 804 | General Formula (13) | General Formula (13) | CN | Formula (24) | General Formula (13) | H | H | $t$-$C_4H_9$ | H | H | H |
| 805 | General Formula (13) | General Formula (13) | CN | Formula (24) | General Formula (13) | H | H | Cl | H | H | H |
| 806 | General Formula (13) | General Formula (13) | CN | Formula (24) | General Formula (13) | H | H | F | H | H | H |

TABLE 5

| Compound No. | General Formula (1) | | | | | General Formula (14) | | | | | | | $R^{51}, R^{56}, R^{58}, R^{60}, R^{62}$ |
|---|---|---|---|---|---|---|---|---|---|---|---|---|---|
| | $R^1$ | $R^2$ | $R^3$ | $R^4$ | $R^5$ | $R^{52}$ | $R^{53}$ | $R^{54}$ | $R^{55}$ | $R^{57}$ | $R^{59}$ | $R^{61}$ | |
| 901 | General Formula (14) | General Formula (14) | CN | General Formula (14) | General Formula (14) | H | H | H | H | H | H | H | H |
| 902 | General Formula (14) | General Formula (14) | CN | General Formula (14) | General Formula (14) | $CH_3$ | H | H | H | H | H | H | H |
| 903 | General Formula (14) | General Formula (14) | CN | General Formula (14) | General Formula (14) | $CH_3O$ | H | H | H | H | H | H | H |
| 904 | General Formula (14) | General Formula (14) | CN | General Formula (14) | General Formula (14) | H | $CH_3$ | H | H | H | H | H | H |
| 905 | General Formula (14) | General Formula (14) | CN | General Formula (14) | General Formula (14) | H | $CH_3O$ | H | H | H | H | H | H |
| 906 | General Formula (14) | General Formula (14) | CN | General Formula (14) | General Formula (14) | H | $t-C_4H_9$ | H | H | H | H | H | H |
| 907 | General Formula (14) | General Formula (14) | CN | General Formula (14) | General Formula (14) | H | Cl | H | H | H | H | H | H |
| 908 | General Formula (14) | General Formula (14) | CN | General Formula (14) | General Formula (14) | H | F | H | H | H | H | H | H |
| 909 | General Formula (14) | General Formula (14) | CN | General Formula (14) | General Formula (14) | H | H | $CH_3$ | H | H | H | H | H |
| 910 | General Formula (14) | General Formula (14) | CN | General Formula (14) | General Formula (14) | H | H | $CH_3O$ | H | H | H | H | H |
| 911 | General Formula (14) | General Formula (14) | CN | General Formula (14) | General Formula (14) | H | H | H | $CH_3$ | H | H | H | H |
| 912 | General Formula (14) | General Formula (14) | CN | General Formula (14) | General Formula (14) | H | H | H | $CH_3O$ | H | H | H | H |
| 913 | General Formula (14) | General Formula (14) | CN | General Formula (14) | General Formula (14) | H | H | H | H | $CH_3$ | H | H | H |
| 914 | General Formula (14) | General Formula (14) | CN | General Formula (14) | General Formula (14) | H | H | H | H | $CH_3O$ | H | H | H |
| 915 | General Formula (14) | General Formula (14) | CN | General Formula (14) | General Formula (14) | H | H | H | H | H | $CH_3$ | H | H |
| 916 | General Formula (14) | General Formula (14) | CN | General Formula (14) | General Formula (14) | H | H | H | H | H | $CH_3O$ | H | H |
| 917 | General Formula (14) | General Formula (14) | CN | General Formula (14) | General Formula (14) | H | H | H | H | H | H | $CH_3$ | H |
| 918 | General Formula (14) | General Formula (14) | CN | General Formula (14) | General Formula (14) | H | H | H | H | H | H | $CH_3O$ | H |
| 919 | General Formula (14) | General Formula (14) | CN | General Formula (14) | H | H | H | H | H | H | H | H | H |
| 920 | General Formula (14) | General Formula (14) | CN | H | General Formula (14) | H | H | H | H | H | H | H | H |
| 921 | General Formula (14) | General Formula (14) | CN | H | H | H | H | H | H | H | H | H | H |
| 922 | General Formula (14) | H | CN | General Formula (14) | H | H | H | H | H | H | H | H | H |
| 923 | H | General Formula (14) | CN | General Formula (14) | H | H | H | H | H | H | H | H | H |
| 924 | General Formula (14) | H | CN | H | H | H | H | H | H | H | H | H | H |

TABLE 5-continued

| Compound No. | General Formula (1) | | | | | General Formula (14) | | | | | | | $R^{51}, R^{56}, R^{58}, R^{60}, R^{62}$ |
|---|---|---|---|---|---|---|---|---|---|---|---|---|---|
| | $R^1$ | $R^2$ | $R^3$ | $R^4$ | $R^5$ | $R^{52}$ | $R^{53}$ | $R^{54}$ | $R^{55}$ | $R^{57}$ | $R^{59}$ | $R^{61}$ | |
| 925 | General Formula (14) | General Formula (14) | CN | General Formula (14) | F | H | H | H | H | H | H | H | H |
| 926 | General Formula (14) | General Formula (14) | CN | F | General Formula (14) | H | H | H | H | H | H | H | H |
| 927 | General Formula (14) | General Formula (14) | CN | F | F | H | H | H | H | H | H | H | H |
| 928 | General Formula (14) | F | CN | General Formula (14) | F | H | H | H | H | H | H | H | H |
| 929 | F | General Formula (14) | CN | General Formula (14) | F | H | H | H | H | H | H | H | H |
| 930 | General Formula (14) | F | CN | F | F | H | H | H | H | H | H | H | H |
| 931 | General Formula (14) | General Formula (14) | CN | General Formula (14) | OH | H | H | H | H | H | H | H | H |
| 932 | General Formula (14) | General Formula (14) | CN | OH | General Formula (14) | H | H | H | H | H | H | H | H |
| 933 | General Formula (14) | General Formula (14) | CN | OH | OH | H | H | H | H | H | H | H | H |
| 934 | General Formula (14) | OH | CN | General Formula (14) | OH | H | H | H | H | H | H | H | H |
| 935 | OH | General Formula (14) | CN | General Formula (14) | OH | H | H | H | H | H | H | H | H |
| 936 | General Formula (14) | OH | CN | OH | OH | H | H | H | H | H | H | H | H |
| 937 | General Formula (14) | General Formula (14) | CN | Cl | General Formula (14) | H | H | H | H | H | H | H | H |
| 938 | General Formula (14) | General Formula (14) | CN | Cl | General Formula (14) | H | $CH_3$ | H | H | H | H | H | H |
| 939 | General Formula (14) | General Formula (14) | CN | Cl | General Formula (14) | H | $CH_3O$ | H | H | H | H | H | H |
| 940 | General Formula (14) | General Formula (14) | CN | Cl | General Formula (14) | H | $t\text{-}C_4H_9$ | H | H | H | H | H | H |
| 941 | General Formula (14) | General Formula (14) | CN | Cl | General Formula (14) | H | Cl | H | H | H | H | H | H |
| 942 | General Formula (14) | General Formula (14) | CN | Cl | General Formula (14) | H | F | H | H | H | H | H | H |
| 943 | General Formula (14) | General Formula (14) | CN | F | General Formula (14) | H | H | H | H | H | H | H | H |
| 944 | General Formula (14) | General Formula (14) | CN | F | General Formula (14) | H | $CH_3$ | H | H | H | H | H | H |
| 945 | General Formula (14) | General Formula (14) | CN | F | General Formula (14) | H | $CH_3O$ | H | H | H | H | H | H |
| 946 | General Formula (14) | General Formula (14) | CN | F | General Formula (14) | H | $t\text{-}C_4H_9$ | H | H | H | H | H | H |
| 947 | General Formula (14) | General Formula (14) | CN | F | General Formula (14) | H | Cl | H | H | H | H | H | H |
| 948 | General Formula (14) | General Formula (14) | CN | F | General Formula (14) | H | F | H | H | H | H | H | H |

TABLE 5-continued

| Compound No. | General Formula (1) R¹ | R² | R³ | R⁴ | R⁵ | General Formula (14) R⁵² | R⁵³ | R⁵⁴ | R⁵⁵ | R⁵⁷ | R⁵⁹ | R⁶¹ | R⁵¹, R⁵⁶, R⁵⁸, R⁶⁰, R⁶² |
|---|---|---|---|---|---|---|---|---|---|---|---|---|---|
| 949 | General Formula (14) | General Formula (14) | CN | CH₃O | General Formula (14) | H | H | H | H | H | H | H | H |
| 950 | General Formula (14) | General Formula (14) | CN | CH₃O | General Formula (14) | H | CH₃ | H | H | H | H | H | H |
| 951 | General Formula (14) | General Formula (14) | CN | CH₃O | General Formula (14) | H | CH₃O | H | H | H | H | H | H |
| 952 | General Formula (14) | General Formula (14) | CN | CH₃O | General Formula (14) | H | t-C₄H₉ | H | H | H | H | H | H |
| 953 | General Formula (14) | General Formula (14) | CN | CH₃O | General Formula (14) | H | Cl | H | H | H | H | H | H |
| 954 | General Formula (14) | General Formula (14) | CN | CH₃O | General Formula (14) | H | F | H | H | H | H | H | H |
| 955 | General Formula (14) | General Formula (14) | CN | C₂H₅O | General Formula (14) | H | H | H | H | H | H | H | H |
| 956 | General Formula (14) | General Formula (14) | CN | C₂H₅O | General Formula (14) | H | CH₃ | H | H | H | H | H | H |
| 957 | General Formula (14) | General Formula (14) | CN | C₂H₅O | General Formula (14) | H | CH₃O | H | H | H | H | H | H |
| 958 | General Formula (14) | General Formula (14) | CN | C₂H₅O | General Formula (14) | H | t-C₄H₉ | H | H | H | H | H | H |
| 959 | General Formula (14) | General Formula (14) | CN | C₂H₅O | General Formula (14) | H | Cl | H | H | H | H | H | H |
| 960 | General Formula (14) | General Formula (14) | CN | C₂H₅O | General Formula (14) | H | F | H | H | H | H | H | H |
| 961 | General Formula (14) | General Formula (14) | CN | C₆H₅O | General Formula (14) | H | H | H | H | H | H | H | H |
| 962 | General Formula (14) | General Formula (14) | CN | C₆H₅O | General Formula (14) | H | CH₃ | H | H | H | H | H | H |
| 963 | General Formula (14) | General Formula (14) | CN | C₆H₅O | General Formula (14) | H | CH₃O | H | H | H | H | H | H |
| 964 | General Formula (14) | General Formula (14) | CN | C₆H₅O | General Formula (14) | H | t-C₄H₉ | H | H | H | H | H | H |
| 965 | General Formula (14) | General Formula (14) | CN | C₆H₅O | General Formula (14) | H | Cl | H | H | H | H | H | H |
| 966 | General Formula (14) | General Formula (14) | CN | C₆H₅O | General Formula (14) | H | F | H | H | H | H | H | H |
| 967 | General Formula (14) | General Formula (14) | CN | Formula (21) | General Formula (14) | H | H | H | H | H | H | H | H |
| 968 | General Formula (14) | General Formula (14) | CN | Formula (21) | General Formula (14) | H | CH₃ | H | H | H | H | H | H |
| 969 | General Formula (14) | General Formula (14) | CN | Formula (21) | General Formula (14) | H | CH₃O | H | H | H | H | H | H |
| 970 | General Formula (14) | General Formula (14) | CN | Formula (21) | General Formula (14) | H | t-C₄H₉ | H | H | H | H | H | H |
| 971 | General Formula (14) | General Formula (14) | CN | Formula (21) | General Formula (14) | H | Cl | H | H | H | H | H | H |
| 972 | General Formula (14) | General Formula (14) | CN | Formula (21) | General Formula (14) | H | F | H | H | H | H | H | H |

TABLE 5-continued

| Compound No. | General Formula (1) | | | | | General Formula (14) | | | | | | | $R^{51}$, $R^{56}$, $R^{58}$, $R^{60}$, $R^{62}$ |
|---|---|---|---|---|---|---|---|---|---|---|---|---|---|
| | $R^1$ | $R^2$ | $R^3$ | $R^4$ | $R^5$ | $R^{52}$ | $R^{53}$ | $R^{54}$ | $R^{55}$ | $R^{57}$ | $R^{59}$ | $R^{61}$ | |
| 973 | General Formula (14) | General Formula (14) | CN | Formula (22) | General Formula (14) | H | H | H | H | H | H | H | H |
| 974 | General Formula (14) | General Formula (14) | CN | Formula (22) | General Formula (14) | H | $CH_3$ | H | H | H | H | H | H |
| 975 | General Formula (14) | General Formula (14) | CN | Formula (22) | General Formula (14) | H | $CH_3O$ | H | H | H | H | H | H |
| 976 | General Formula (14) | General Formula (14) | CN | Formula (22) | General Formula (14) | H | $t-C_4H_9$ | H | H | H | H | H | H |
| 977 | General Formula (14) | General Formula (14) | CN | Formula (22) | General Formula (14) | H | Cl | H | H | H | H | H | H |
| 978 | General Formula (14) | General Formula (14) | CN | Formula (22) | General Formula (14) | H | F | H | H | H | H | H | H |
| 979 | General Formula (14) | General Formula (14) | CN | Formula (23) | General Formula (14) | H | H | H | H | H | H | H | H |
| 980 | General Formula (14) | General Formula (14) | CN | Formula (23) | General Formula (14) | H | $CH_3$ | H | H | H | H | H | H |
| 981 | General Formula (14) | General Formula (14) | CN | Formula (23) | General Formula (14) | H | $CH_3O$ | H | H | H | H | H | H |
| 982 | General Formula (14) | General Formula (14) | CN | Formula (23) | General Formula (14) | H | $t-C_4H_9$ | H | H | H | H | H | H |
| 983 | General Formula (14) | General Formula (14) | CN | Formula (23) | General Formula (14) | H | Cl | H | H | H | H | H | H |
| 984 | General Formula (14) | General Formula (14) | CN | Formula (23) | General Formula (14) | H | F | H | H | H | H | H | H |
| 985 | General Formula (14) | General Formula (14) | CN | Formula (24) | General Formula (14) | H | H | H | H | H | H | H | H |
| 986 | General Formula (14) | General Formula (14) | CN | Formula (24) | General Formula (14) | H | $CH_3$ | H | H | H | H | H | H |
| 987 | General Formula (14) | General Formula (14) | CN | Formula (24) | General Formula (14) | H | $CH_3O$ | H | H | H | H | H | H |
| 988 | General Formula (14) | General Formula (14) | CN | Formula (24) | General Formula (14) | H | $t-C_4H_9$ | H | H | H | H | H | H |
| 989 | General Formula (14) | General Formula (14) | CN | Formula (24) | General Formula (14) | H | Cl | H | H | H | H | H | H |
| 990 | General Formula (14) | General Formula (14) | CN | Formula (24) | General Formula (14) | H | F | H | H | H | H | H | H |

TABLE 6

| Compound No. | General Formula (1) | | | | | General Formula (15) | | | | | |
|---|---|---|---|---|---|---|---|---|---|---|---|
| | $R^1$ | $R^2$ | $R^3$ | $R^4$ | $R^5$ | $R^{71}$, $R^{80}$ | $R^{72}$, $R^{79}$ | $R^{73}$, $R^{78}$ | | $R^{74}$, $R^{77}$ | $R^{75}$, $R^{76}$ |
| 1001 | General Formula (15) | General Formula (15) | CN | General Formula (15) | General Formula (15) | H | H | H | | H | H |
| 1002 | General Formula (15) | General Formula (15) | CN | General Formula (15) | General Formula (15) | H | $CH_3$ | H | | H | H |
| 1003 | General Formula (15) | General Formula (15) | CN | General Formula (15) | General Formula (15) | H | $CH_3O$ | H | | H | H |

TABLE 6-continued

| Compound No. | General Formula (1) R¹ | R² | R³ | R⁴ | R⁵ | General Formula (15) R⁷¹, R⁸⁰ | R⁷², R⁷⁹ | R⁷³, R⁷⁸ | R⁷⁴, R⁷⁷ | R⁷⁵, R⁷⁶ |
|---|---|---|---|---|---|---|---|---|---|---|
| 1004 | General Formula (15) | General Formula (15) | CN | General Formula (15) | General Formula (15) | H | $C_6H_5$ | H | H | H |
| 1005 | General Formula (15) | General Formula (15) | CN | General Formula (15) | General Formula (15) | H | $CH_3$ | H | $CH_3$ | H |
| 1006 | General Formula (15) | General Formula (15) | CN | General Formula (15) | General Formula (15) | H | $CH_3O$ | H | $CH_3O$ | H |
| 1007 | General Formula (15) | General Formula (15) | CN | General Formula (15) | General Formula (15) | H | $C_6H_5$ | H | $C_6H_5$ | H |
| 1008 | General Formula (15) | General Formula (15) | CN | General Formula (15) | General Formula (15) | H | H | $CH_3$ | H | H |
| 1009 | General Formula (15) | General Formula (15) | CN | General Formula (15) | General Formula (15) | H | H | $CH_3O$ | H | H |
| 1010 | General Formula (15) | General Formula (15) | CN | General Formula (15) | General Formula (15) | H | H | $t\text{-}C_4H_9$ | H | H |
| 1011 | General Formula (15) | General Formula (15) | CN | General Formula (15) | General Formula (15) | H | H | Cl | H | H |
| 1012 | General Formula (15) | General Formula (15) | CN | General Formula (15) | General Formula (15) | H | H | F | H | H |
| 1013 | General Formula (15) | General Formula (15) | CN | General Formula (15) | General Formula (15) | H | H | $C_6H_5$ | H | H |
| 1014 | General Formula (15) | General Formula (15) | CN | General Formula (15) | General Formula (15) | H | H | $p\text{-}C_6H_5\text{—}C_6H_4$ | H | H |
| 1015 | General Formula (15) | General Formula (15) | CN | General Formula (15) | H | H | H | H | H | H |
| 1016 | General Formula (15) | General Formula (15) | CN | H | General Formula (15) | H | H | H | H | H |
| 1017 | General Formula (15) | General Formula (15) | CN | H | H | H | H | H | H | H |
| 1018 | General Formula (15) | H | CN | General Formula (15) | H | H | H | H | H | H |
| 1019 | H | General Formula (15) | CN | General Formula (15) | H | H | H | H | H | H |
| 1020 | General Formula (15) | H | CN | H | H | H | H | H | H | H |
| 1021 | General Formula (15) | General Formula (15) | CN | General Formula (15) | F | H | H | H | H | H |
| 1022 | General Formula (15) | General Formula (15) | CN | F | General Formula (15) | H | H | H | H | H |
| 1023 | General Formula (15) | General Formula (15) | CN | F | F | H | H | H | H | H |
| 1024 | General Formula (15) | F | CN | General Formula (15) | F | H | H | H | H | H |
| 1025 | F | General Formula (15) | CN | General Formula (15) | F | H | H | H | H | H |
| 1026 | General Formula (15) | F | CN | F | F | H | H | H | H | H |
| 1027 | General Formula (15) | General Formula (15) | CN | General Formula (15) | OH | H | H | H | H | H |
| 1028 | General Formula (15) | General Formula (15) | CN | OH | General Formula (15) | H | H | H | H | H |

TABLE 6-continued

| Compound No. | General Formula (1) R$^1$ | R$^2$ | R$^3$ | R$^4$ | R$^5$ | General Formula (15) R$^{71}$, R$^{80}$ | R$^{72}$, R$^{79}$ | R$^{73}$, R$^{78}$ | R$^{74}$, R$^{77}$ | R$^{75}$, R$^{76}$ |
|---|---|---|---|---|---|---|---|---|---|---|
| 1029 | General Formula (15) | General Formula (15) | CN | OH | OH | H | H | H | H | H |
| 1030 | General Formula (15) | OH | CN | General Formula (15) | OH | H | H | H | H | H |
| 1031 | OH | General Formula (15) | CN | General Formula (15) | OH | H | H | H | H | H |
| 1032 | General Formula (15) | OH | CN | OH | OH | H | H | H | H | H |
| 1033 | General Formula (15) | General Formula (15) | CN | Cl | General Formula (15) | H | H | H | H | H |
| 1034 | General Formula (15) | General Formula (15) | CN | Cl | General Formula (15) | H | H | CH$_3$ | H | H |
| 1035 | General Formula (15) | General Formula (15) | CN | Cl | General Formula (15) | H | H | CH$_3$O | H | H |
| 1036 | General Formula (15) | General Formula (15) | CN | Cl | General Formula (15) | H | H | t-C$_4$H$_9$ | H | H |
| 1037 | General Formula (15) | General Formula (15) | CN | Cl | General Formula (15) | H | H | Cl | H | H |
| 1038 | General Formula (15) | General Formula (15) | CN | Cl | General Formula (15) | H | H | F | H | H |
| 1039 | General Formula (15) | General Formula (15) | CN | F | General Formula (15) | H | H | H | H | H |
| 1040 | General Formula (15) | General Formula (15) | CN | F | General Formula (15) | H | H | CH$_3$ | H | H |
| 1041 | General Formula (15) | General Formula (15) | CN | F | General Formula (15) | H | H | CH$_3$O | H | H |
| 1042 | General Formula (15) | General Formula (15) | CN | F | General Formula (15) | H | H | t-C$_4$H$_9$ | H | H |
| 1043 | General Formula (15) | General Formula (15) | CN | F | General Formula (15) | H | H | Cl | H | H |
| 1044 | General Formula (15) | General Formula (15) | CN | F | General Formula (15) | H | H | F | H | H |
| 1045 | General Formula (15) | General Formula (15) | CN | CH$_3$O | General Formula (15) | H | H | H | H | H |
| 1046 | General Formula (15) | General Formula (15) | CN | CH$_3$O | General Formula (15) | H | H | CH$_3$ | H | H |
| 1047 | General Formula (15) | General Formula (15) | CN | CH$_3$O | General Formula (15) | H | H | CH$_3$O | H | H |
| 1048 | General Formula (15) | General Formula (15) | CN | CH$_3$O | General Formula (15) | H | H | t-C$_4$H$_9$ | H | H |
| 1049 | General Formula (15) | General Formula (15) | CN | CH$_3$O | General Formula (15) | H | H | Cl | H | H |
| 1050 | General Formula (15) | General Formula (15) | CN | CH$_3$O | General Formula (15) | H | H | F | H | H |
| 1051 | General Formula (15) | General Formula (15) | CN | C$_2$H$_5$O | General Formula (15) | H | H | H | H | H |
| 1052 | General Formula (15) | General Formula (15) | CN | C$_2$H$_5$O | General Formula (15) | H | H | CH$_3$ | H | H |
| 1053 | General Formula (15) | General Formula (15) | CN | C$_2$H$_5$O | General Formula (15) | H | H | CH$_3$O | H | H |

TABLE 6-continued

| Compound No. | General Formula (1) | | | | | General Formula (15) | | | | |
|---|---|---|---|---|---|---|---|---|---|---|
| | $R^1$ | $R^2$ | $R^3$ | $R^4$ | $R^5$ | $R^{71}, R^{80}$ | $R^{72}, R^{79}$ | $R^{73}, R^{78}$ | $R^{74}, R^{77}$ | $R^{75}, R^{76}$ |
| 1054 | General Formula (15) | General Formula (15) | CN | $C_2H_5O$ | General Formula (15) | H | H | $t-C_4H_9$ | H | H |
| 1055 | General Formula (15) | General Formula (15) | CN | $C_2H_5O$ | General Formula (15) | H | H | Cl | H | H |
| 1056 | General Formula (15) | General Formula (15) | CN | $C_2H_5O$ | General Formula (15) | H | H | F | H | H |
| 1057 | General Formula (15) | General Formula (15) | CN | $C_6H_5O$ | General Formula (15) | H | H | H | H | H |
| 1058 | General Formula (15) | General Formula (15) | CN | $C_6H_5O$ | General Formula (15) | H | H | $CH_3$ | H | H |
| 1059 | General Formula (15) | General Formula (15) | CN | $C_6H_5O$ | General Formula (15) | H | H | $CH_3O$ | H | H |
| 1060 | General Formula (15) | General Formula (15) | CN | $C_6H_5O$ | General Formula (15) | H | H | $t-C_4H_9$ | H | H |
| 1061 | General Formula (15) | General Formula (15) | CN | $C_6H_5O$ | General Formula (15) | H | H | Cl | H | H |
| 1062 | General Formula (15) | General Formula (15) | CN | $C_6H_5O$ | General Formula (15) | H | H | F | H | H |
| 1063 | General Formula (15) | General Formula (15) | CN | Formula (21) | General Formula (15) | H | H | H | H | H |
| 1064 | General Formula (15) | General Formula (15) | CN | Formula (21) | General Formula (15) | H | H | $CH_3$ | H | H |
| 1065 | General Formula (15) | General Formula (15) | CN | Formula (21) | General Formula (15) | H | H | $CH_3O$ | H | H |
| 1066 | General Formula (15) | General Formula (15) | CN | Formula (21) | General Formula (15) | H | H | $t-C_4H_9$ | H | H |
| 1067 | General Formula (15) | General Formula (15) | CN | Formula (21) | General Formula (15) | H | H | Cl | H | H |
| 1068 | General Formula (15) | General Formula (15) | CN | Formula (21) | General Formula (15) | H | H | F | H | H |
| 1069 | General Formula (15) | General Formula (15) | CN | Formula (22) | General Formula (15) | H | H | H | H | H |
| 1070 | General Formula (15) | General Formula (15) | CN | Formula (22) | General Formula (15) | H | H | $CH_3$ | H | H |
| 1071 | General Formula (15) | General Formula (15) | CN | Formula (22) | General Formula (15) | H | H | $CH_3O$ | H | H |
| 1072 | General Formula (15) | General Formula (15) | CN | Formula (22) | General Formula (15) | H | H | $t-C_4H_9$ | H | H |
| 1073 | General Formula (15) | General Formula (15) | CN | Formula (22) | General Formula (15) | H | H | Cl | H | H |
| 1074 | General Formula (15) | General Formula (15) | CN | Formula (22) | General Formula (15) | H | H | F | H | H |
| 1075 | General Formula (15) | General Formula (15) | CN | Formula (23) | General Formula (15) | H | H | H | H | H |
| 1076 | General Formula (15) | General Formula (15) | CN | Formula (23) | General Formula (15) | H | H | $CH_3$ | H | H |
| 1077 | General Formula (15) | General Formula (15) | CN | Formula (23) | General Formula (15) | H | H | $CH_3O$ | H | H |
| 1078 | General Formula (15) | General Formula (15) | CN | Formula (23) | General Formula (15) | H | H | $t-C_4H_9$ | H | H |

TABLE 6-continued

| Compound | General Formula (1) | | | | | General Formula (15) | | | | |
|---|---|---|---|---|---|---|---|---|---|---|
| No. | $R^1$ | $R^2$ | $R^3$ | $R^4$ | $R^5$ | $R^{71}, R^{80}$ | $R^{72}, R^{79}$ | $R^{73}, R^{78}$ | $R^{74}, R^{77}$ | $R^{75}, R^{76}$ |
| 1079 | General Formula (15) | General Formula (15) | CN | Formula (23) | General Formula (15) | H | H | Cl | H | H |
| 1080 | General Formula (15) | General Formula (15) | CN | Formula (23) | General Formula (15) | H | H | F | H | H |
| 1081 | General Formula (15) | General Formula (15) | CN | Formula (24) | General Formula (15) | H | H | H | H | H |
| 1082 | General Formula (15) | General Formula (15) | CN | Formula (24) | General Formula (15) | H | H | $CH_3$ | H | H |
| 1083 | General Formula (15) | General Formula (15) | CN | Formula (24) | General Formula (15) | H | H | $CH_3O$ | H | H |
| 1084 | General Formula (15) | General Formula (15) | CN | Formula (24) | General Formula (15) | H | H | $t\text{-}C_4H_9$ | H | H |
| 1085 | General Formula (15) | General Formula (15) | CN | Formula (24) | General Formula (15) | H | H | Cl | H | H |
| 1086 | General Formula (15) | General Formula (15) | CN | Formula (24) | General Formula (15) | H | H | F | H | H |

In the case where an organic layer containing the compound represented by the general formula (1) is to be produced by vapor deposition method, for example, the molecular weight of the compound represented by the general formula (1) is preferably 1,500 or less, more preferably 1,200 or less, further preferably 1,000 or less, and still further preferably 800 or less. The lower limit of the molecular weight is generally 247 or more, and preferably 290 or more.

The compound represented by the general formula (1) may be formed into a film by a coating method irrespective of the molecular weight thereof. A film may be formed with the compound having a relatively large molecular weight by a coating method.

As an application of the invention, a compound that contains plural structures each represented by the general formula (1) in the molecule may be used in a light-emitting layer of an organic light-emitting device.

For example, a polymer that is obtained by polymerizing a polymerizable monomer having a structure represented by the general formula (1) may be used in a light-emitting layer of an organic light-emitting device. Specifically, a monomer having a polymerizable functional group in any of $R^1$ to $R^5$ in the general formula (1) may be prepared and homopolymerized or copolymerized with another monomer to provide a polymer having the repeating unit, and the polymer may be used in a light-emitting layer of an organic light-emitting device. Alternatively, compounds each having a structure represented by the general formula (1) may be coupled to form a dimer or a trimer, and the dimer or the trimer may be used in a light-emitting layer of an organic light-emitting device.

Examples of the structure of the repeating unit constituting the polymer containing the structure represented by the general formula (1) include ones having a structure, in which any of $R^1$ to $R^5$ in the general formula (1) is represented by the following general formula (17) or (18).

[Chem. 13]

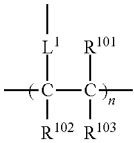

General Formula (17)

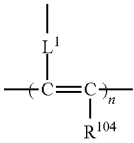

General Formula (18)

In the general formulae (17) and (18), $L^1$ and $L^2$ each represent a linking group. The linking group preferably has from 0 to 20 carbon atoms, more preferably from 1 to 15 carbon atoms, and further preferably from 2 to 10 carbon atoms. The linking group preferably has a structure represented by —$X^{11}$-$L^{11}$-, wherein $X^{11}$ represents an oxygen atom or a sulfur atom, and preferably an oxygen atom, and $L^{11}$ represents a linking group, preferably a substituted or unsubstituted alkylene group or a substituted or unsubstituted arylene group, and more preferably a substituted or unsubstituted alkylene group having from 1 to 10 carbon atoms or a substituted or unsubstituted phenylene group.

In the general formulae (17) and (18), $R^{101}$, $R^{102}$, $R^{103}$ and $R^{104}$ each independently represent a substituent, preferably a substituted or unsubstituted alkyl group having from 1 to 6 carbon atoms, a substituted or unsubstituted alkoxy group having from 1 to 6 carbon atoms, or a halogen atom, more preferably an unsubstituted alkyl group having from 1 to 3 carbon atoms, an unsubstituted alkoxy group having from 1 to 3 carbon atoms, a fluorine atom, or a chlorine atom, and further preferably an unsubstituted alkyl group having from 1 to 3 carbon atoms or an unsubstituted alkoxy group having from 1 to 3 carbon atoms.

Specific examples of the structure of the repeating unit include ones having a structure, in which any of $R^1$ to $R^5$ in the general formula (1) is the following formulae (21) to (24). Two or more of $R^1$ to $R^5$ may be the formulae (21) to (24), and it is preferred that one of $R^1$ to $R^5$ is the formulae (21) to (24).

[Chem. 14]

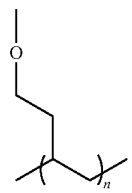

Formula (21)

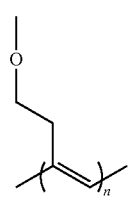

Formula (22)

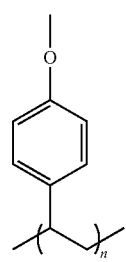

Formula (23)

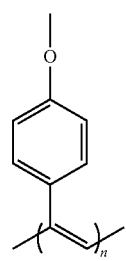

Formula (24)

The polymer having the repeating unit containing the formulae (21) to (24) may be synthesized in such a manner that with at least one of $R^1$ to $R^5$ in the general formula (1) that is a hydroxy group, the following compounds is reacted with the hydroxy group as a linker to introduce a polymerizable group thereto, and the polymerizable group is then polymerized.

[Chem. 15]

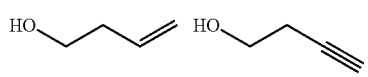

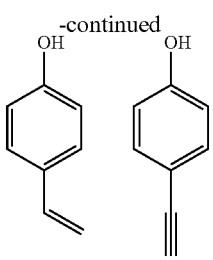

-continued

The polymer containing the structure represented by the general formula (1) in the molecule may be a polymer that is formed only of a repeating unit having the structure represented by the general formula (1), or may be a polymer that further contains a repeating unit having another structure. The repeating unit having the structure represented by the general formula (1) contained in the polymer may be formed of a single species or two or more species. Examples of the repeating unit that does not have the structure represented by the general formula (1) include ones derived from monomers that are ordinarily used in copolymerization. Examples thereof include a repeating unit derived from a monomer having an ethylenic unsaturated bond, such as ethylene and styrene.

Compound Represented by General Formula (2)

In the compound represented by the general formula (1), a compound having a structure represented by the following general formula (2) is a novel compound.

[Chem. 16]

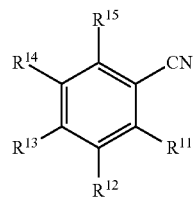

General Formula (2)

In the general formula (2), at least one of $R^{11}$, $R^{12}$, $R^{14}$ and $R^{15}$ represents a cyano group, at least three of $R^{11}$ to $R^{15}$ each represent a substituted or unsubstituted 9-carbazolyl group, a substituted or unsubstituted 1,2,3,4-tetrahydro-9-carbazolyl group, a substituted or unsubstituted 1-indolyl group or a substituted or unsubstituted diarylamino group, and the balance of $R^{11}$ to $R^{15}$ represents a hydroxy group.

In $R^{11}$ to $R^{15}$ in the general formula (2), any one of $R^{11}$ and $R^{12}$ is preferably a cyano group. At least three of $R^{11}$ to $R^{15}$ each represent a 9-carbazolyl group or the like, and these three substituents may be the same as or different from each other, and it is preferred that all of them are the same as each other. At least three of $R^{11}$ to $R^{15}$ each preferably represent a group having a structure represented by any of the general formulae (12) to (15). For specific examples and preferred ranges of the general formulae (12) to (15), reference may be made to the corresponding description for the general formula (1). In $R^{11}$ to $R^{15}$ in the general formula (2), none or one of them is a hydroxy group. In the case where one of them is a hydroxy group, the hydroxy group is preferably $R^{14}$. Examples of the case include the case where $R^{13}$ represents a cyano group, and $R^{14}$ represents a hydroxy group.

The synthesis method of the compound represented by the general formula (2) is not particularly limited. The compound represented by the general formula (2) may be synthesized by combining known synthesis methods and conditions appropriately.

Preferred examples of the synthesis method include a method of preparing tetrafluorodicyanobenzene and then reacting the same with carbazole, indole, a diarylamine or the like. According to the reaction, such a compound may be synthesized that is represented by the general formula (2), wherein any one of $R^{11}$ to $R^{15}$ represents a cyano group, and the balance thereof each represents a carbazolyl group, an indolyl group or a diarylamino group. By using trifluorotricyanobenzene as the starting material, such a compound may be synthesized that is represented by the general formula (2), wherein any two of $R^{11}$ to $R^{15}$ each represent a cyano group, and the balance thereof each represents a carbazolyl group, an indolyl group or a diarylamino group. Furthermore, a hydroxy group may be introduced to the benzene ring by performing, for example, a process of adding water and applying ultrasonic wave thereto.

For the details of the reaction, reference may be made to the synthesis examples described later. The compound represented by the general formula (2) may be synthesized by combining other known synthesis reactions.

Compound Represented by General Formula (3)

In the compound represented by the general formula (1), a compound having a structure represented by the following general formula (3) is useful as a blue light-emitting material.

[Chem. 17]

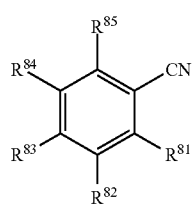

General Formula (3)

In the general formula (3) one of $R^{81}$ to $R^{85}$ represents a cyano group, two of $R^{81}$ to $R^{85}$ each represent a substituted or unsubstituted 9-carbazolyl group, and the other two thereof each represent a hydrogen atom.

Specific examples of the compound represented by the general formula (3) will be shown below, but the compound represented by the general formula (3) capable of being used in the invention is not construed as being limited to the specific examples. In the following specific examples, Cz represents a 9-carbazolyl group. Examples thereof also include compound, wherein Cz represents a 3-methylcarbazol-9-yl group or a 3,6-dimethylcarbazol-9-yl group.

[Chem. 18]

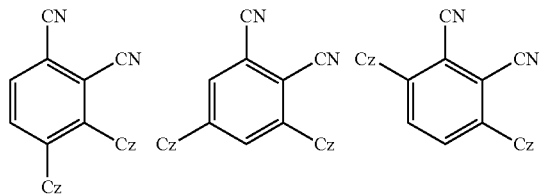

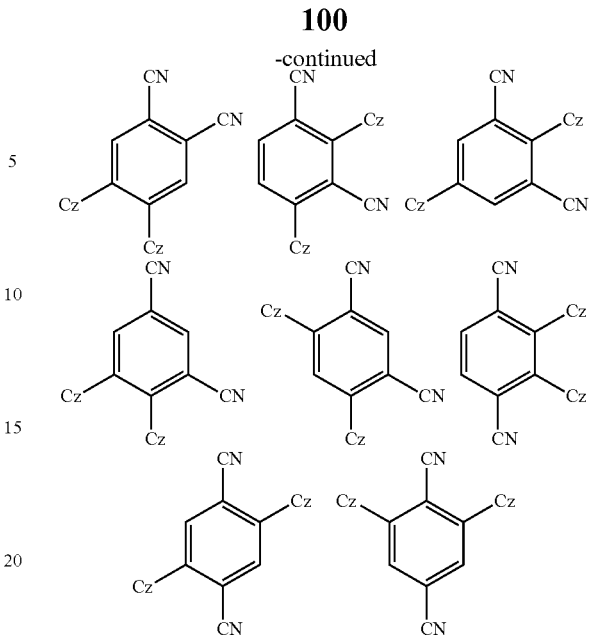

Organic Light-Emitting Device

The compound represented by the general formula (1) of the invention is useful as a light-emitting material of an organic light-emitting device. The compound represented by the general formula (1) of the invention thus may be effectively used as a light-emitting material in a light-emitting layer of an organic light-emitting device. The compound represented by the general formula (1) includes a delayed fluorescent material emitting delayed fluorescent light (i.e. delayed fluorescent emitter). Accordingly, the invention also relates to an invention of a delayed fluorescent emitter having a structure represented by the general formula (1), an invention of the use of the compound represented by the general formula (1) as a delayed fluorescent emitter, and an invention of a method of emitting delayed fluorescent light with the compound represented by the general formula (1). An organic light-emitting device using the compound as a light-emitting material has features that the device emits delayed fluorescent light and has a high light emission efficiency. The principle of the features will be described as follows for an organic electroluminescent device as an example.

In an organic electroluminescent device, carriers are injected from an anode and a cathode to a light-emitting material to form an excited state for the light-emitting material, with which light is emitted. In the case of a carrier injection type organic electroluminescent device, in general, excitons that are excited to the excited singlet state are 25% of the total excitons generated, and the remaining 75% thereof are excited to the excited triplet state. Accordingly, the use of phosphorescence, which is light emission from the excited triplet state, provides a high energy utilization. However, the excited triplet state has a long lifetime and thus causes saturation of the excited state and deactivation of energy through mutual action with the excitons in the excited triplet state, and therefore the quantum efficiency of phosphorescence may generally be often not high. A delayed fluorescent material emits fluorescent light through the mechanism that the energy of excitons transits to the excited triplet state through intersystem crossing or the like, and then transits to the excited singlet state through reverse intersystem crossing due to triplet-triplet annihilation or absorption of thermal energy, thereby emitting fluorescent light. It is considered that among the materials, a thermal activation type delayed fluorescent material emitting light through absorption of thermal energy is particularly useful for an organic electroluminescent device. In the case where a delayed fluorescent material is used in an organic electroluminescent device, the excitons in the excited singlet state normally emit fluorescent light. On the other hand, the excitons in the excited triplet state emit fluorescent light through intersystem crossing to the excited singlet state by absorbing the heat generated by the device. At this time, the light emitted through reverse intersystem crossing from the excited triplet state to the excited single state has the same wavelength as fluorescent light since it is light emission from the excited single state, but has a longer lifetime (light emission lifetime) than the normal fluorescent light and phosphorescent light, and thus the light is observed as fluorescent light that is delayed from the normal fluorescent light and phosphorescent light. The light may be defined as delayed fluorescent light. The use of the thermal activation type exciton transition mechanism may raise the proportion of the compound in the excited single state, which is generally formed in a proportion only of 25%, to 25% or more through the absorption of the thermal energy after the carrier injection. A compound that emits strong fluorescent light and delayed fluorescent light at a low temperature of lower than 100° C. undergoes the intersystem crossing from the excited triplet state to the excited singlet state sufficiently with the heat of the device, thereby emitting delayed fluorescent light, and thus the use of the compound may drastically enhance the light emission efficiency.

The use of the compound represented by the general formula (1) of the invention as a light-emitting material of a light-emitting layer may provide an excellent organic light-emitting device, such as an organic photoluminescent device (organic PL device) and an organic electroluminescent device (organic EL device). The organic photoluminescent device has a structure containing a substrate having formed thereon at least a light-emitting layer. The organic electroluminescent device has a structure containing at least an anode, a cathode and an organic layer formed between the anode and the cathode. The organic layer contains at least a light-emitting layer, and may be formed only of a light-emitting layer, or may have one or more organic layer in addition to the light-emitting layer. Examples of the organic layer include a hole transporting layer, a hole injection layer, an electron barrier layer, a hole barrier layer, an electron injection layer, an electron transporting layer and an exciton barrier layer. The hole transporting layer may be a hole injection and transporting layer having a hole injection function, and the electron transporting layer may be an electron injection and transporting layer having an electron injection function. A specific structural example of an organic electroluminescent device is shown in FIG. 1. In FIG. 1, the numeral 1 denotes a substrate, 2 denotes an anode, 3 denotes a hole injection layer, 4 denotes a hole transporting layer, 5 denotes a light-emitting layer, 6 denotes an electron transporting layer, and 7 denotes a cathode.

The members and the layers of the organic electroluminescent device will be described below. The descriptions for the substrate and the light-emitting layer may also be applied to the substrate and the light-emitting layer of the organic photoluminescent device.

Substrate

The organic electroluminescent device of the invention is preferably supported by a substrate. The substrate is not particularly limited and may be those that have been commonly used in an organic electroluminescent device, and examples thereof used include those formed of glass, transparent plastics, quartz and silicon.

Anode

The anode of the organic electroluminescent device used is preferably formed of as an electrode material a metal, an alloy or an electroconductive compound each having a large work function (4 eV or more), or a mixture thereof. Specific examples of the electrode material include a metal, such as Au, and an electroconductive transparent material, such as CuI, indium tin oxide (ITO), $SnO_2$ and ZnO. A material that is amorphous and is capable of forming a transparent electroconductive film, such as IDIXO ($In_2O_3$—ZnO), may also be used. The anode may be formed in such a manner that the electrode material is formed into a thin film by such a method as vapor deposition or sputtering, and the film is patterned into a desired pattern by a photolithography method, or in the case where the pattern may not require high accuracy (for example, approximately 100 μm or more), the pattern may be formed with a mask having a desired shape on vapor deposition or sputtering of the electrode material. In alternative, in the case where a material capable of being applied as a coating, such as an organic electroconductive compound, is used, a wet film forming method, such as a printing method and a coating method, may be used. In the case where emitted light is to be taken out through the anode, the anode preferably has a transmittance of more than 10%, and the anode preferably has a sheet resistance of several hundred Ohm per square or less. The thickness thereof may be generally selected from a range of from 10 to 1,000 nm, and preferably from 10 to 200 nm, while depending on the material used.

Cathode

The cathode is preferably formed of as an electrode material a metal (referred to as an electron injection metal), an alloy or an electroconductive compound each having a small work function (4 eV or less), or a mixture thereof. Specific examples of the electrode material include sodium, a sodium-potassium alloy, magnesium, lithium, a magnesium-copper mixture, a magnesium-silver mixture, a magnesium-aluminum mixture, a magnesium-indium mixture, an aluminum-aluminum oxide ($Al_2O_3$) mixture, indium, a lithium-aluminum mixture, and a rare earth metal. Among these, a mixture of an electron injection metal and a second metal that is a stable metal having a larger work function than the electron injection metal, for example, a magnesium-silver mixture, a magnesium-aluminum mixture, a magnesium-indium mixture, an aluminum-aluminum oxide ($Al_2O_3$) mixture, a lithium-aluminum mixture, and aluminum, are preferred from the standpoint of the electron injection property and the durability against oxidation and the like. The cathode may be produced by forming the electrode material into a thin film by such a method as vapor deposition or sputtering. The cathode preferably has a sheet resistance of several hundred Ohm per square or less, and the thickness thereof may be generally selected from a range of from 10 nm to 5 μm, and preferably from 50 to 200 nm. For transmitting the emitted light, any one of the anode and the cathode of the organic electroluminescent device is preferably transparent or translucent, thereby enhancing the light emission luminance.

The cathode may be formed with the electroconductive transparent materials described for the anode, thereby forming a transparent or translucent cathode, and by applying the cathode, a device having an anode and a cathode, both of which have transmittance, may be produced.

Light-Emitting Layer

The light-emitting layer is a layer, in which holes and electrons injected from the anode and the cathode, respectively, are recombined to form excitons, and then the layer emits light. A light-emitting material may be solely used as the light-emitting layer, but the light-emitting layer preferably contains a light-emitting material and a host material. The light-emitting material used may be one kind or two or more kinds selected from the group of compounds represented by the general formula (1) of the invention. In order that the organic electroluminescent device and the organic photoluminescent device of the invention exhibit a high light emission efficiency, it is important that the singlet excitons and the triplet excitons generated in the light-emitting material are confined in the light-emitting material. Accordingly, a host material is preferably used in addition to the light-emitting material in the light-emitting layer. The host material used may be an organic compound that has excited singlet energy and excited triplet energy, at least one of which is higher than those of the light-emitting material of the invention. As a result, the singlet excitons and the triplet excitons generated in the light-emitting material of the invention are capable of being confined in the molecules of the light-emitting material of the invention, thereby eliciting the light emission efficiency thereof sufficiently. There may be cases where a high light emission efficiency is obtained even though the singlet excitons and the triplet excitons may not be confined sufficiently, and therefore a host material capable of achieving a high light emission efficiency may be used in the invention without any particular limitation. In the organic light-emitting device and the organic electroluminescent device of the invention, the light emission occurs in the light-emitting material of the invention contained in the light-emitting layer. The emitted light contains both fluorescent light and delayed fluorescent light. However, a part of the emitted light may contain emitted light from the host material, or the emitted light may partially contain emitted light from the host material.

In the case where the host material is used, the amount of the compound of the invention as the light-emitting material contained in the light-emitting layer is preferably 0.1% by weight or more, and more preferably 1% by weight or more, and is preferably 50% by weight or less, more preferably 20% by weight or less, and further preferably 10% by weight or less.

The host material in the light-emitting layer is preferably an organic compound that has a hole transporting function and an electron transporting function, prevents the emitted light from being increased in wavelength, and has a high glass transition temperature.

Injection Layer

The injection layer is a layer that is provided between the electrode and the organic layer, for decreasing the driving voltage and enhancing the light emission luminance, and includes a hole injection layer and an electron injection layer, which may be provided between the anode and the light-emitting layer or the hole transporting layer and between the cathode and the light-emitting layer or the electron transporting layer. The injection layer may be provided depending on necessity.

Barrier Layer

The barrier layer is a layer that is capable of inhibiting charges (electrons or holes) and/or excitons present in the light-emitting layer from being diffused outside the light-emitting layer. The electron barrier layer may be disposed between the light-emitting layer and the hole transporting layer, and inhibits electrons from passing through the light-emitting layer toward the hole transporting layer. Similarly, the hole barrier layer may be disposed between the light-emitting layer and the electron transporting layer, and inhibits holes from passing through the light-emitting layer toward the electron transporting layer. The barrier layer may also be used for inhibiting excitons from being diffused outside the light-emitting layer. Thus, the electron barrier layer and the hole barrier layer each may also have a function as an exciton barrier layer. The electron barrier layer or the exciton barrier layer referred herein means a layer that has both the functions of an electron barrier layer and an exciton barrier layer by one layer.

Hole Barrier Layer

The hole barrier layer has the function of an electron transporting layer in a broad sense. The hole barrier layer has a function of inhibiting holes from reaching the electron transporting layer while transporting electrons, and thereby enhances the recombination probability of electrons and holes in the light-emitting layer. As the material for the hole barrier layer, the materials for the electron transporting layer described later may be used depending on necessity.

Electron Barrier Layer

The electron barrier layer has the function of transporting holes in a broad sense. The electron barrier layer has a function of inhibiting electrons from reaching the hole transporting layer while transporting holes, and thereby enhances the recombination probability of electrons and holes in the light-emitting layer.

Exciton Barrier Layer

The exciton barrier layer is a layer for inhibiting excitons generated through recombination of holes and electrons in the light-emitting layer from being diffused to the charge transporting layer, and the use of the layer inserted enables effective confinement of excitons in the light-emitting layer, and thereby enhances the light emission efficiency of the device. The exciton barrier layer may be inserted adjacent to the light-emitting layer on any of the side of the anode and the side of the cathode, and on both the sides. Specifically, in the case where the exciton barrier layer is present on the side of the anode, the layer may be inserted between the hole transporting layer and the light-emitting layer and adjacent to the light-emitting layer, and in the case where the layer is inserted on the side of the cathode, the layer may be inserted between the light-emitting layer and the cathode and adjacent to the light-emitting layer. Between the anode and the exciton barrier layer that is adjacent to the light-emitting layer on the side of the anode, a hole injection layer, an electron barrier layer and the like may be provided, and between the cathode and the exciton barrier layer that is adjacent to the light-emitting layer on the side of the cathode, an electron injection layer, an electron transporting layer, a hole barrier layer and the like may be provided. In the case where the barrier layer is provided, the material used for the barrier layer preferably has excited singlet energy and excited triplet energy, at least one of which is higher than the excited singlet energy and the excited triplet energy of the light-emitting material, respectively.

Hole Transporting Layer

The hole transporting layer is formed of a hole transporting material having a function of transporting holes, and the hole transporting layer may be provided as a single layer or plural layers.

The hole transporting material has one of injection or transporting property of holes and barrier property of electrons, and may be any of an organic material and an inorganic material. Examples of known hole transporting materials that may be used herein include a triazole derivative, an oxadiazole derivative, an imidazole derivative, a carbazole derivative, an indolocarbazole derivative, a polyarylalkane derivative, a pyrazoline derivative, a pyrazolone derivative, a phenylenediamine derivative, an arylamine derivative, an amino-substituted chalcone derivative, an oxazole derivative, a styrylanthracene derivative, a fluorenone derivative, a hydrazone derivative, a stilbene derivative, a silazane derivative, an aniline copolymer and an electroconductive polymer oligomer, particularly a thiophene oligomer. Among these, a porphyrin compound, an aromatic tertiary amine compound and a styrylamine compound are preferably used, and an aromatic tertiary amine compound is more preferably used.

Electron Transporting Layer

The electron transporting layer is formed of a material having a function of transporting electrons, and the electron transporting layer may be provided as a single layer or plural layers.

The electron transporting material (which may also function as a hole barrier material in some cases) may have a function of transporting electrons, which are injected from the cathode, to the light-emitting layer. Examples of the electron transporting layer that may be used herein include a nitro-substituted fluorene derivative, a diphenylquinone derivative, a thiopyran dioxide derivative, carbodiimide, a fluorenylidene methane derivative, anthraquinodimethane and anthrone derivatives, and an oxadiazole derivative. The electron transporting material used may be a thiadiazole derivative obtained by replacing the oxygen atom of the oxadiazole ring of the oxadiazole derivative by a sulfur atom, or a quinoxaline derivative having a quinoxaline ring, which is known as an electron attracting group. Furthermore, polymer materials having these materials introduced to the polymer chain or having these materials used as the main chain of the polymer may also be used.

In the production of the organic electroluminescent device, the compound represented by the general formula (1) may be used not only in the light-emitting layer but also in the other layers than the light-emitting layer. In this case, the compound represented by the general formula (1) used in the light-emitting layer and the compound represented by the general formula (1) used in the other layers than the light-emitting layer may be the same as or different from each other. For example, the compound represented by the general formula (1) may be used in the injection layer, the barrier layer, the hole barrier layer, the electron barrier layer, the exciton barrier layer, the hole transporting layer, the electron transporting layer and the like described above. The film forming method of the layers are not particularly limited, and the layers may be produced by any of a dry process and a wet process.

Specific examples of preferred materials that may be used in the organic electroluminescent device are shown below, but the materials that may be used in the invention are not construed as being limited to the example compounds. The compound that is shown as a material having a particular function may also be used as a material having another function. In the structural formulae of the example compounds, R, R' and $R_1$ to $R_{10}$ each independently represent a hydrogen atom or a substituent; X represents a carbon atom or a heteroatom that forms a cyclic structure; n represents an integer of from 3 to 5; Y represents a substituent; and m represents an integer of 0 or more.

Preferred examples of a compound that may also be used as the host material of the light-emitting layer are shown below.

[Chem. 19]

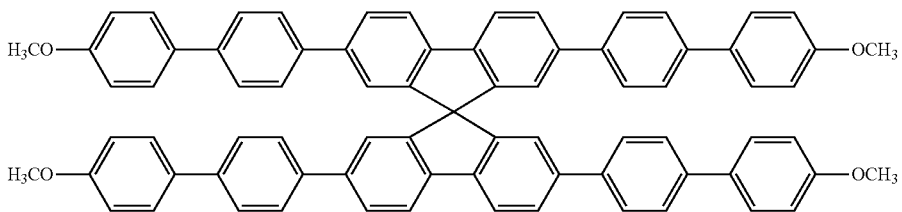

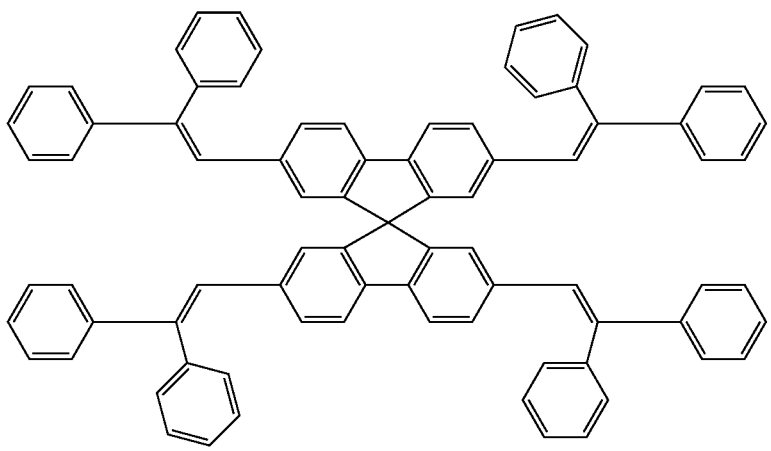

-continued
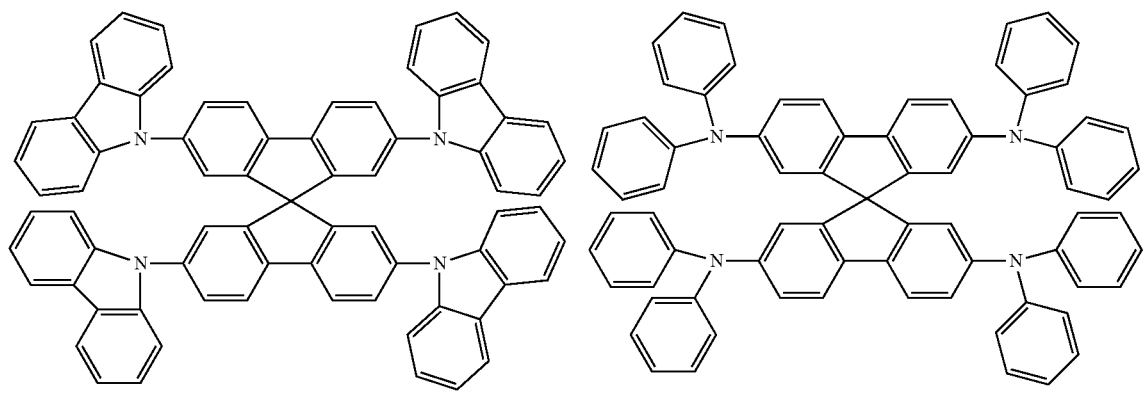
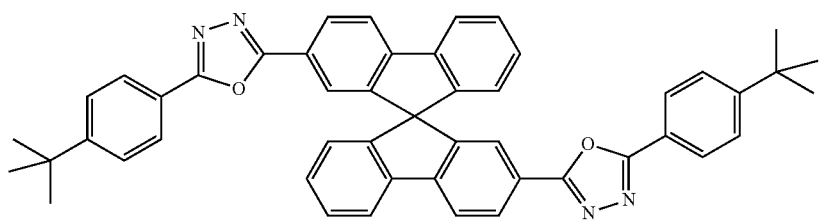
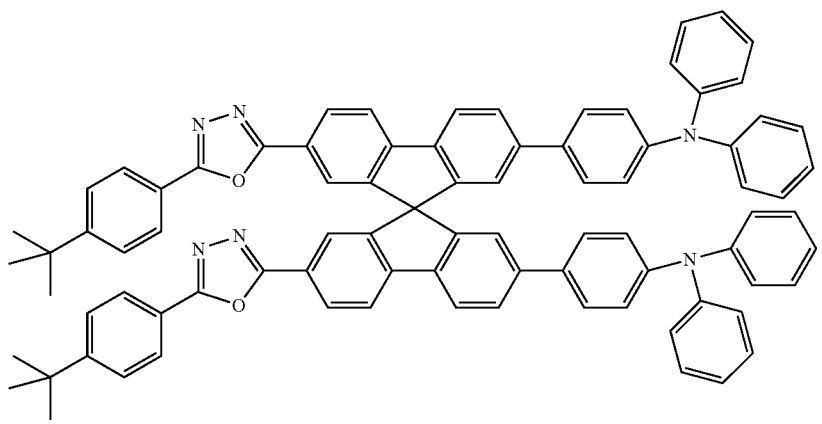
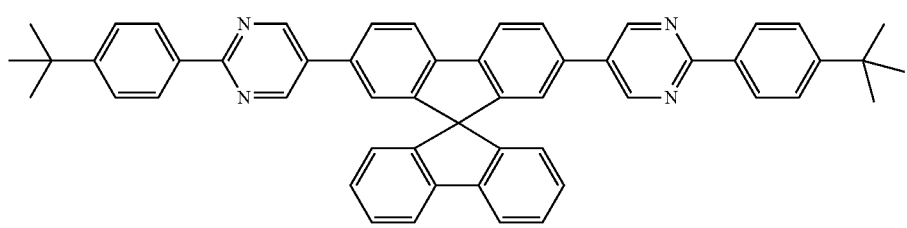
[Chem. 20]
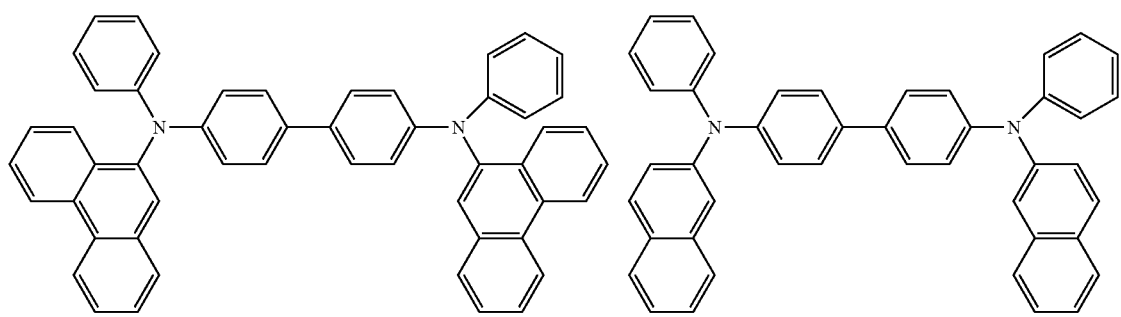

-continued
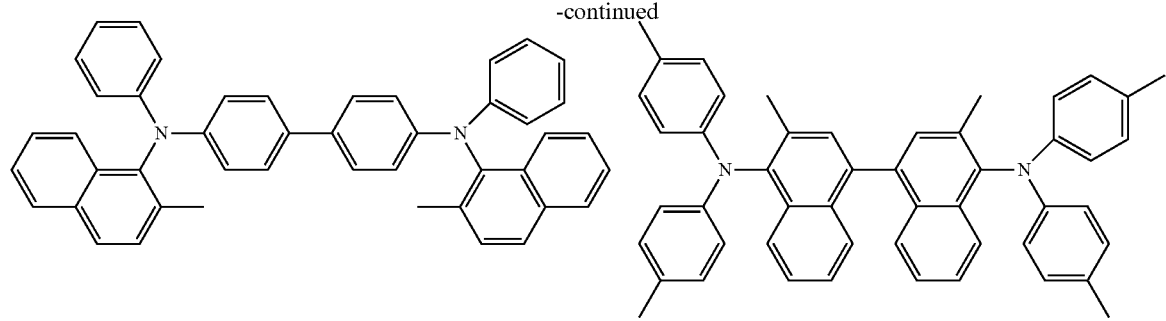
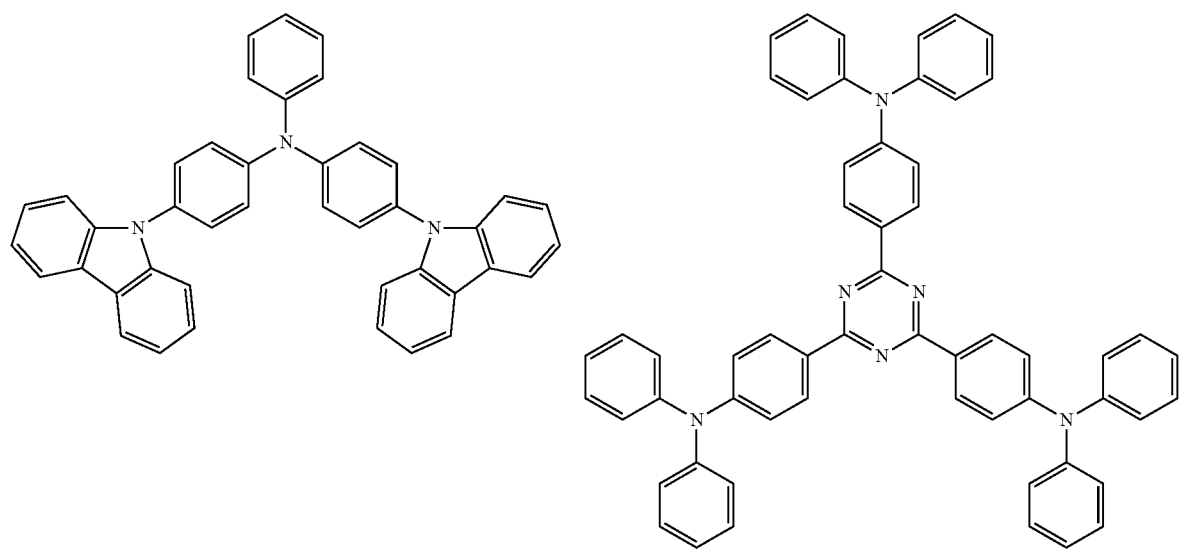
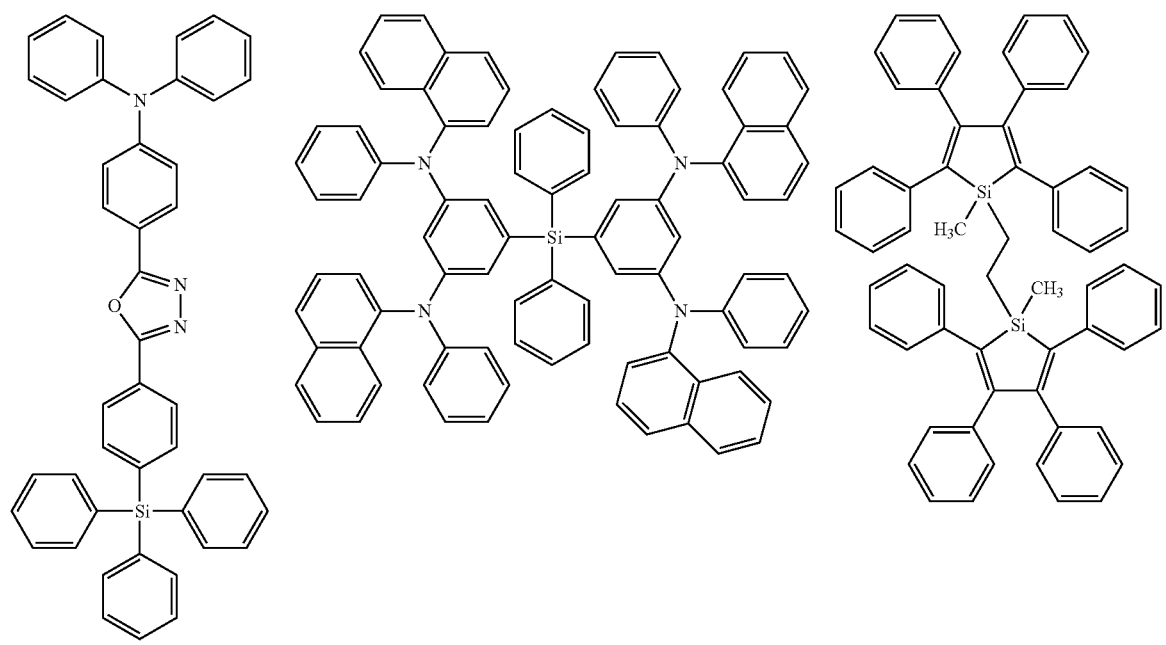

111 112
-continued
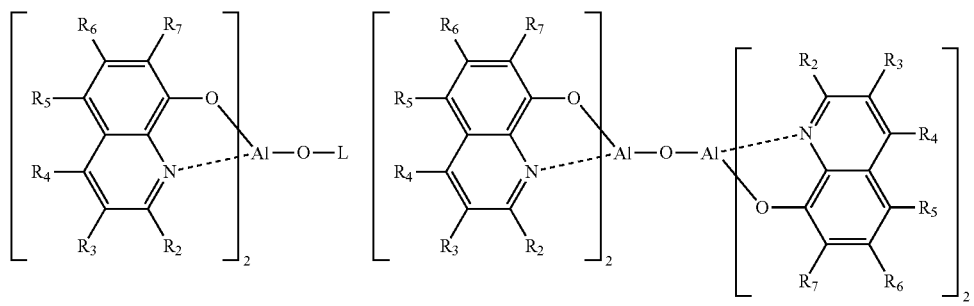
[Chem. 21]
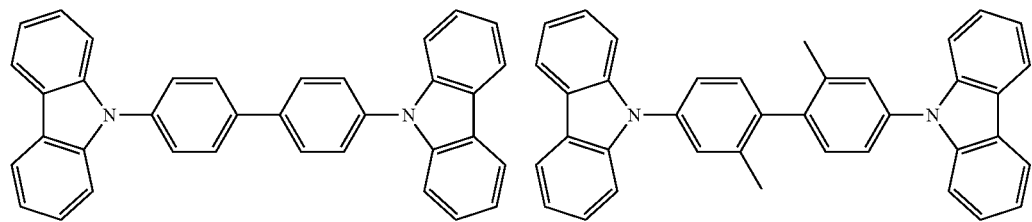
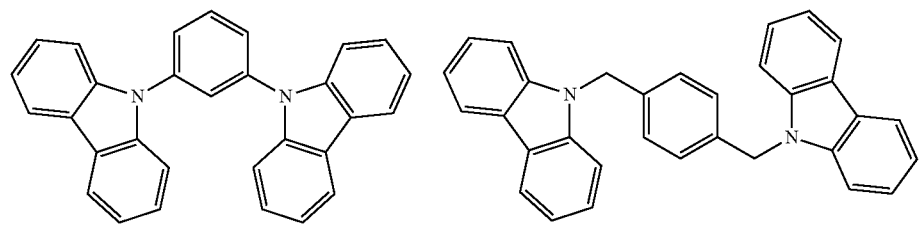
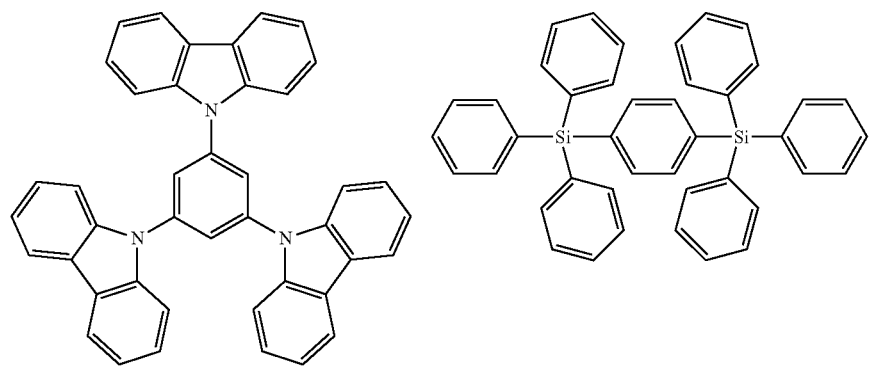
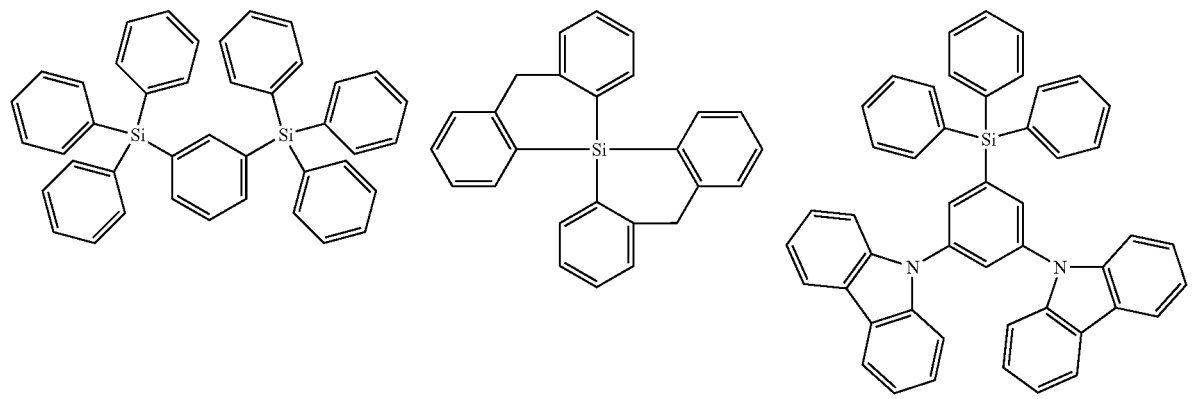

-continued
[Chem. 22]
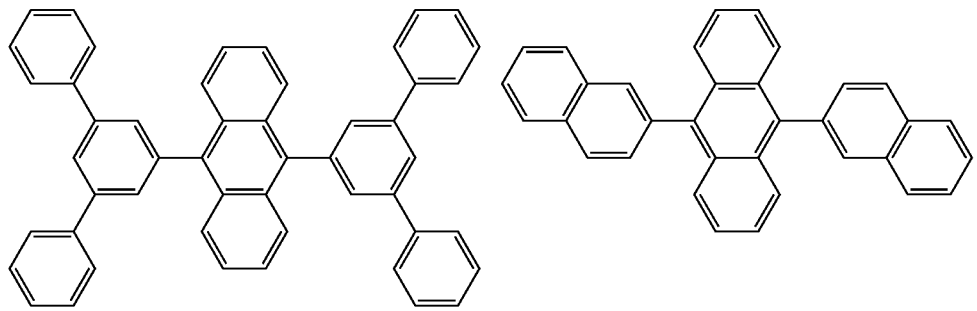

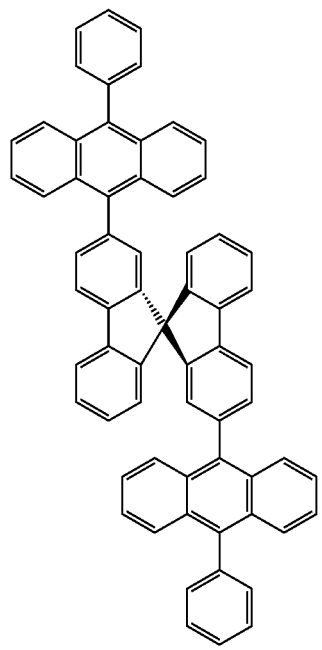
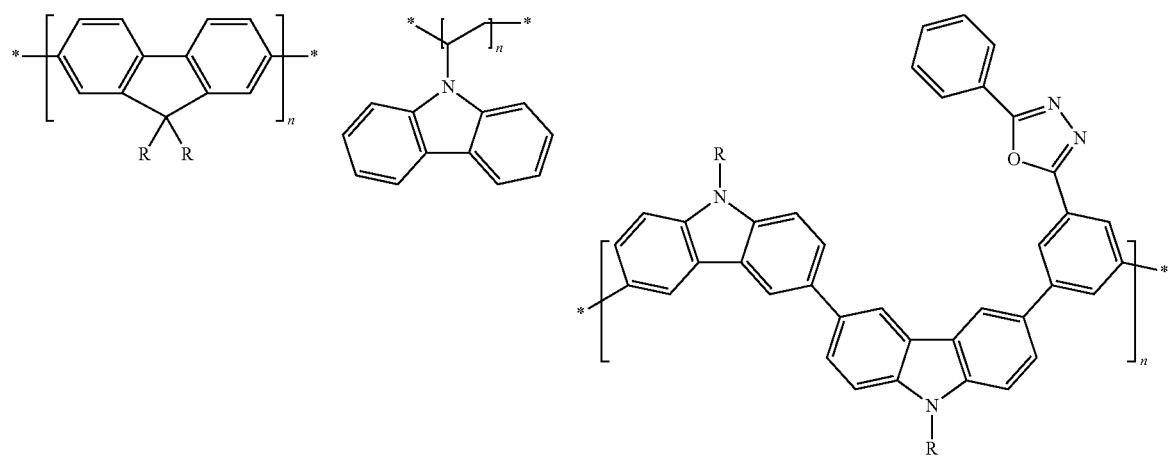
[Chem. 23]
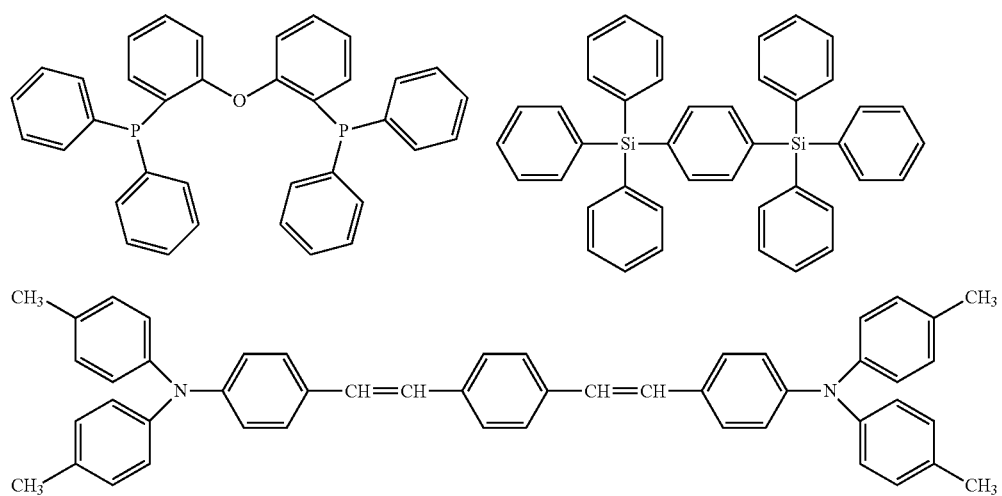

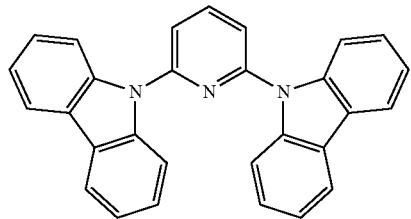
Preferred examples of a compound that may be used as the hole injection material are shown below.
[Chem. 24]
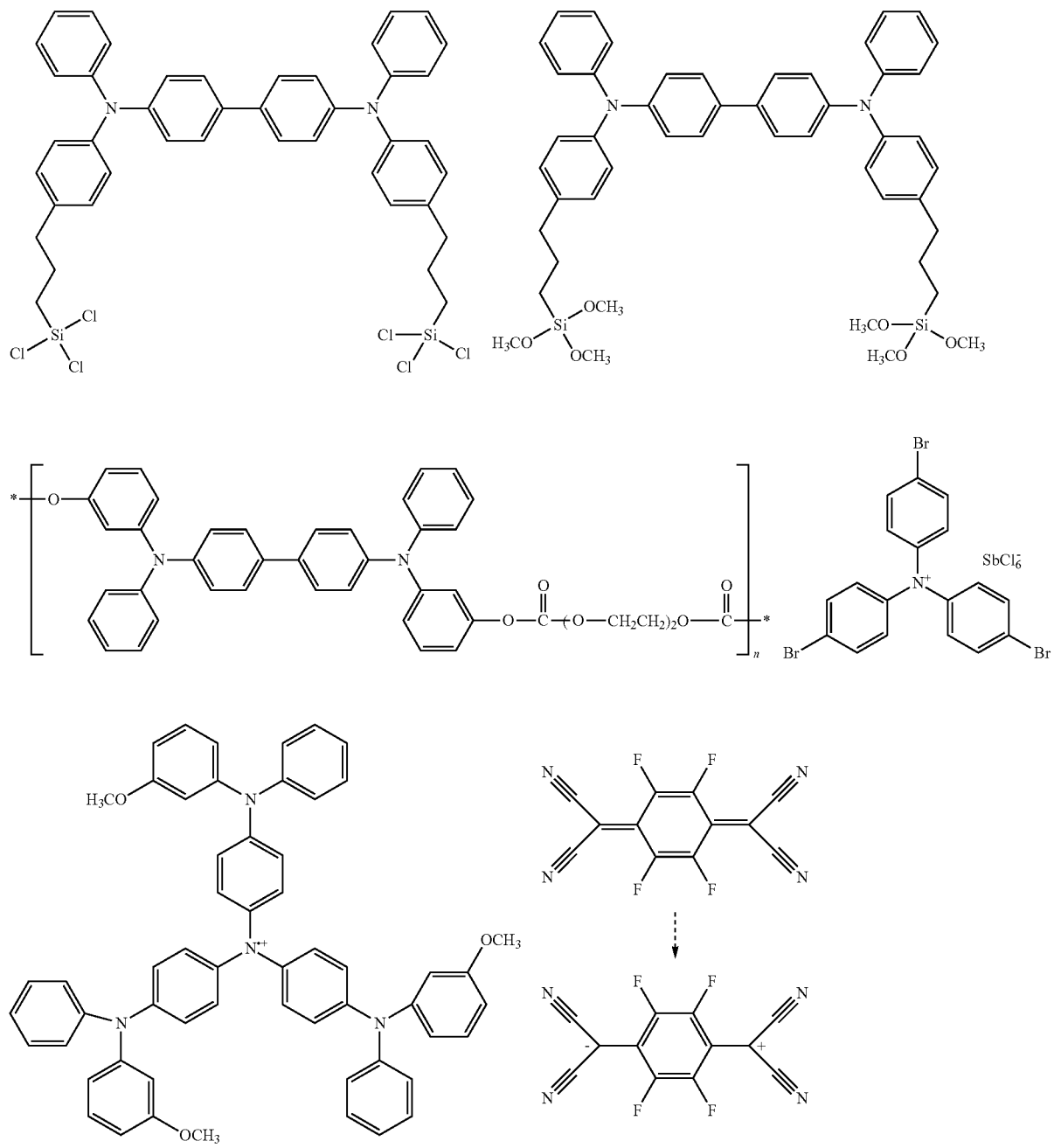

119
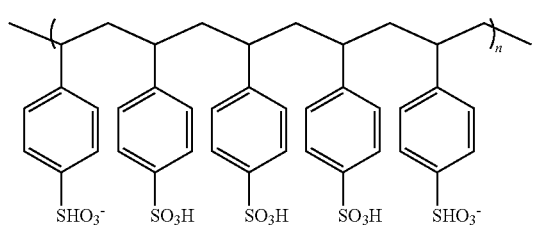
120
-continued
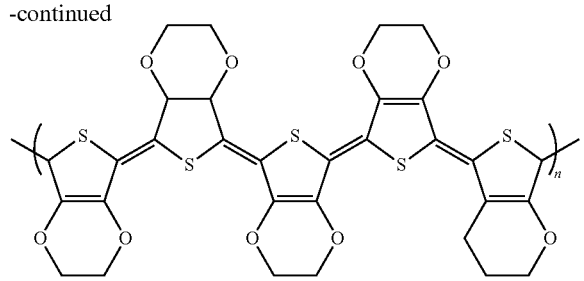
Preferred examples of a compound that may be used as the hole transporting material are shown below.
[Chem. 25]
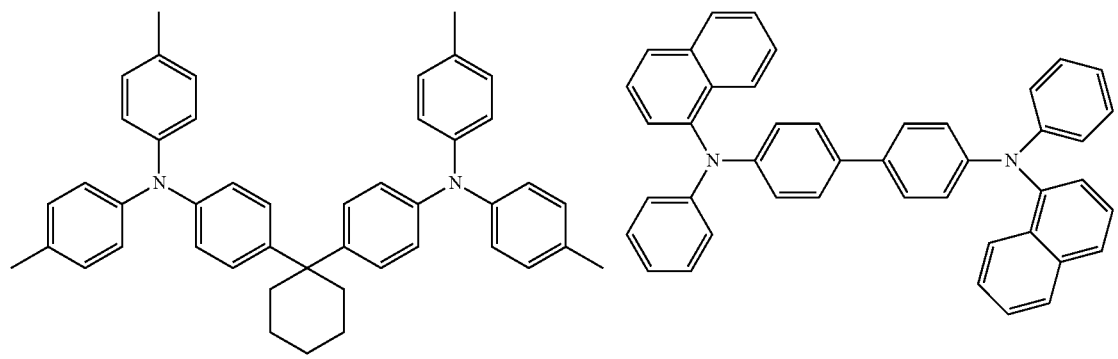
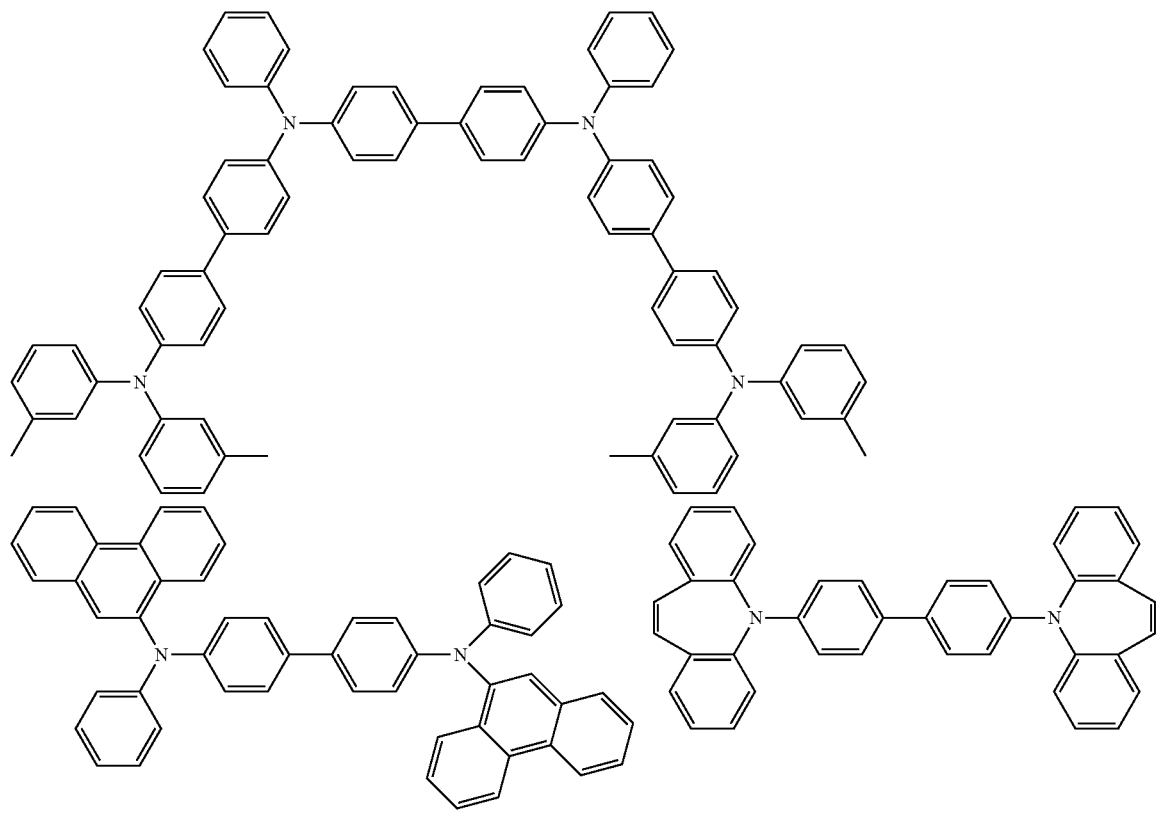

[Chem. 26]
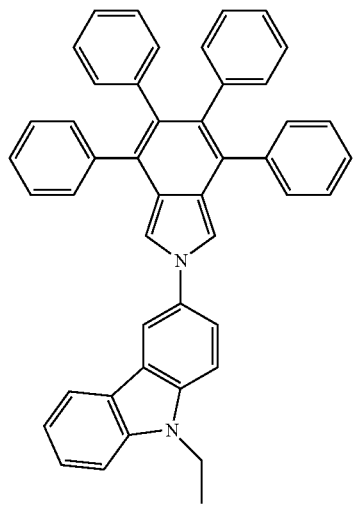
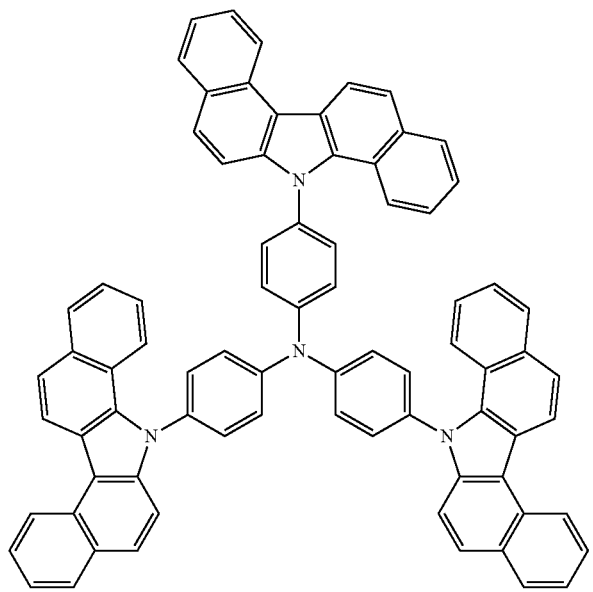
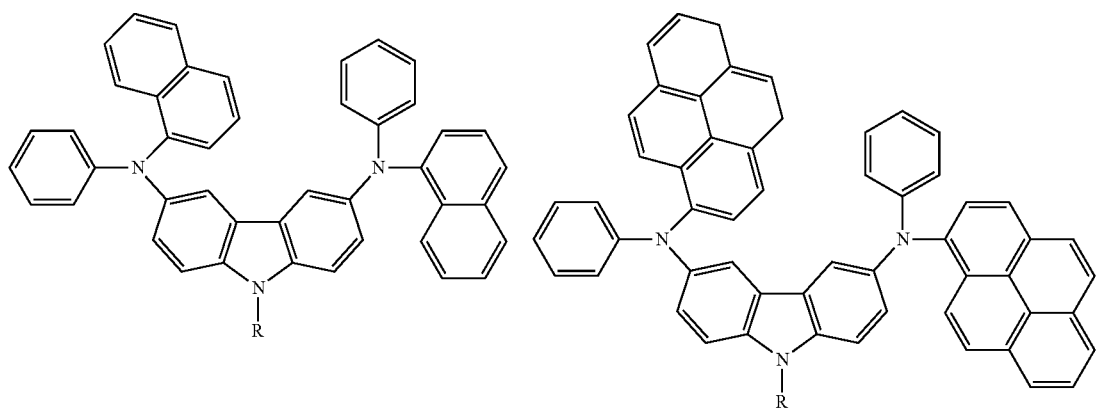
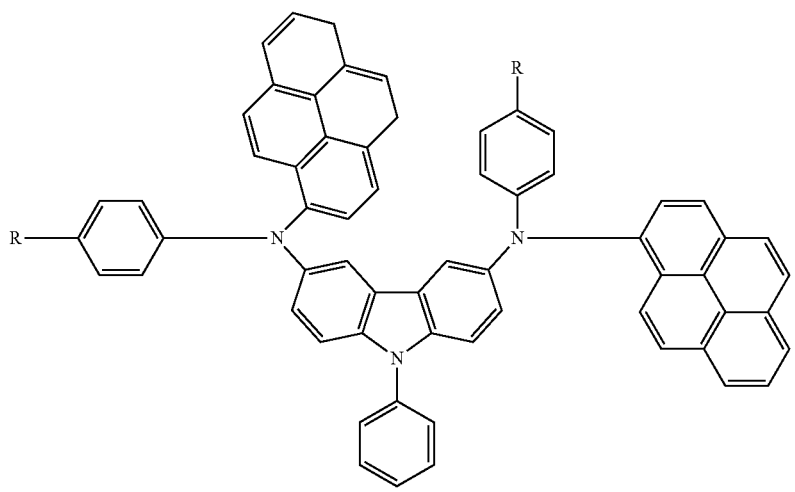

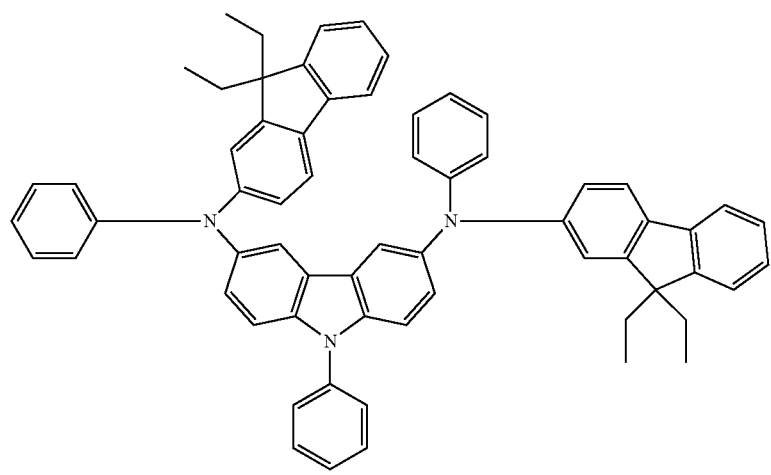
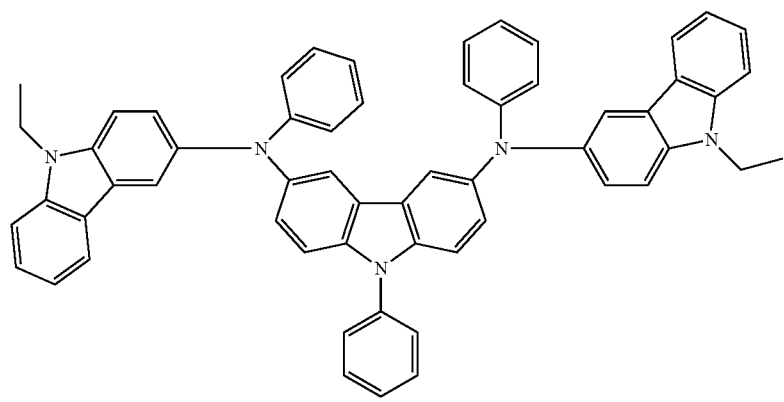
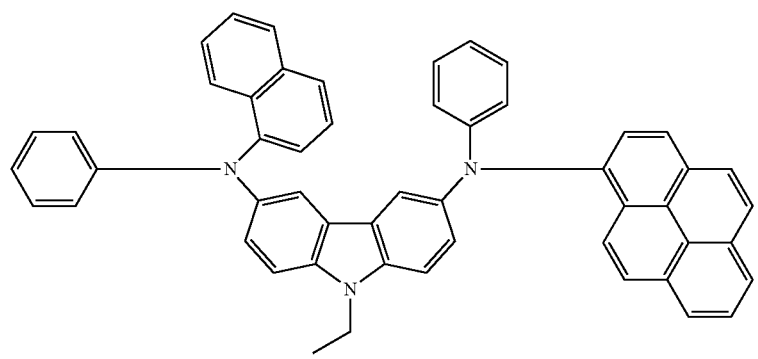

[Chem. 27]
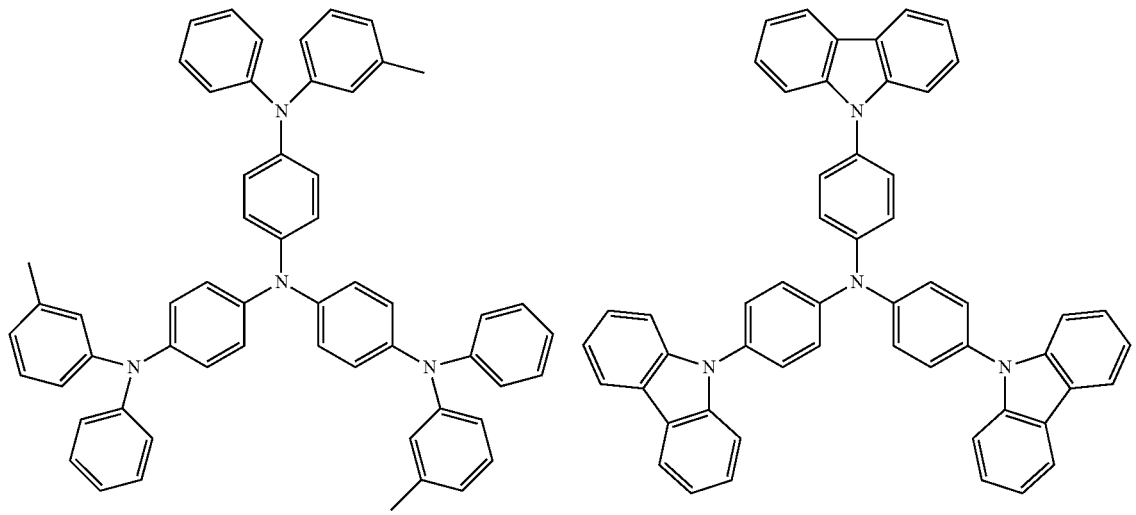
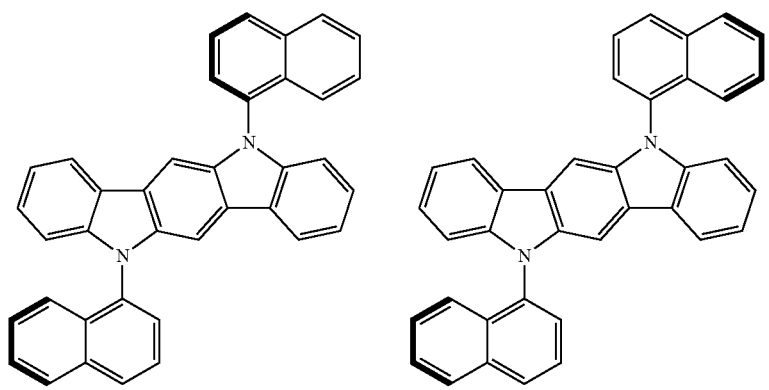
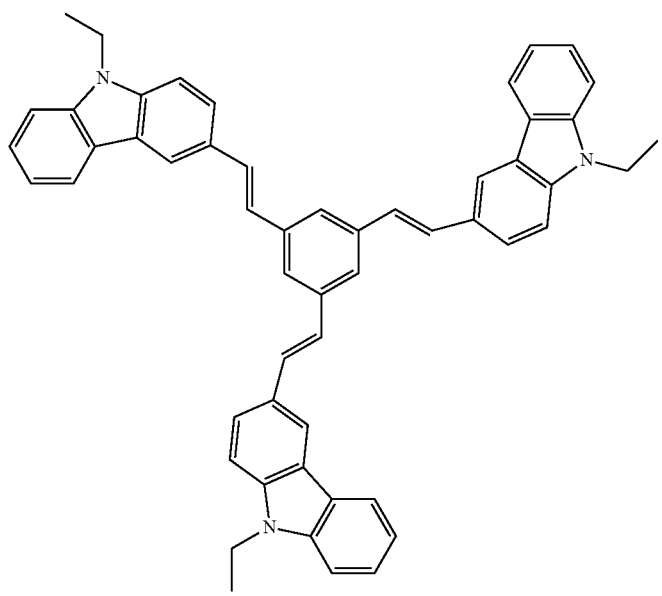

-continued
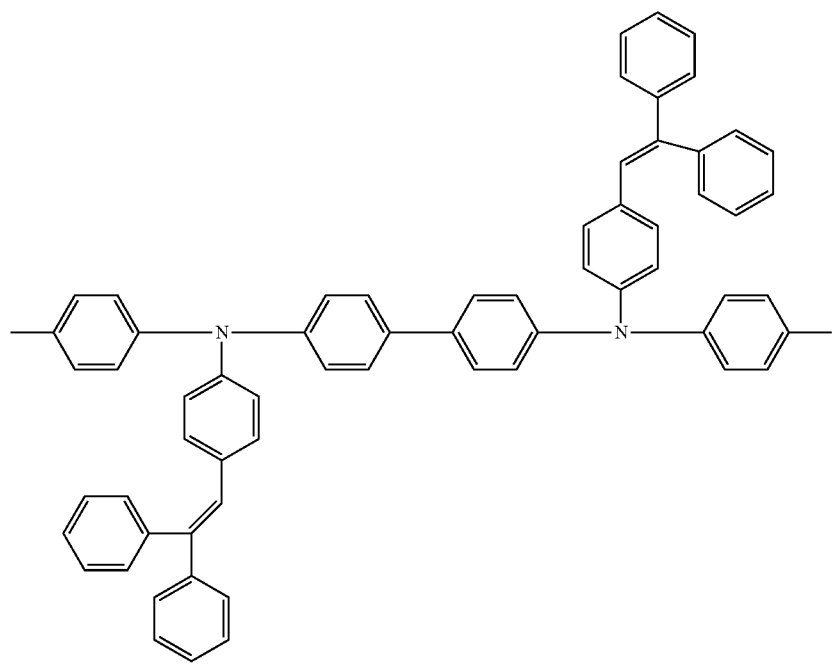
[Chem. 28]
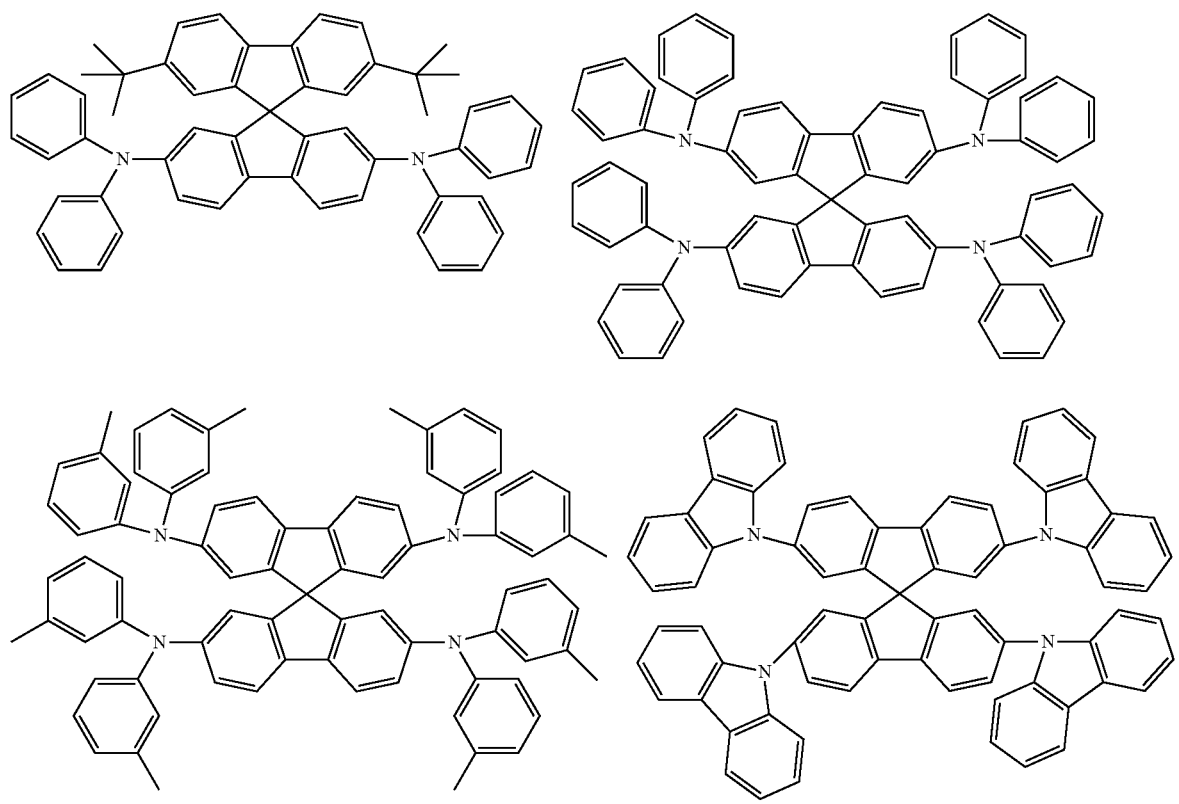
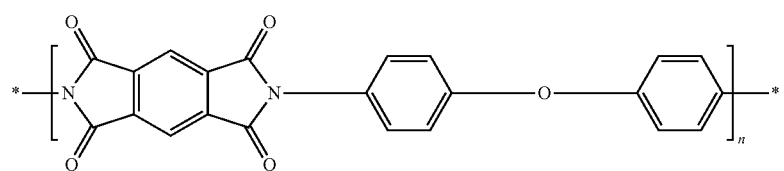

-continued
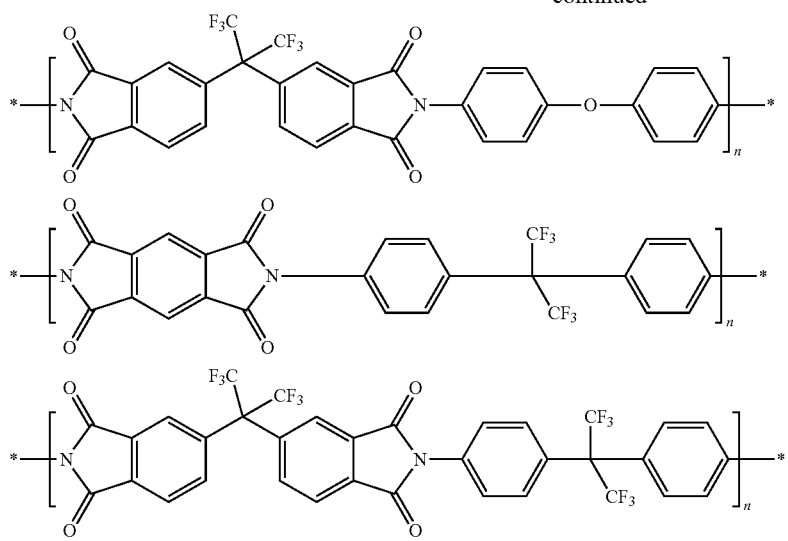
[Chem. 29]
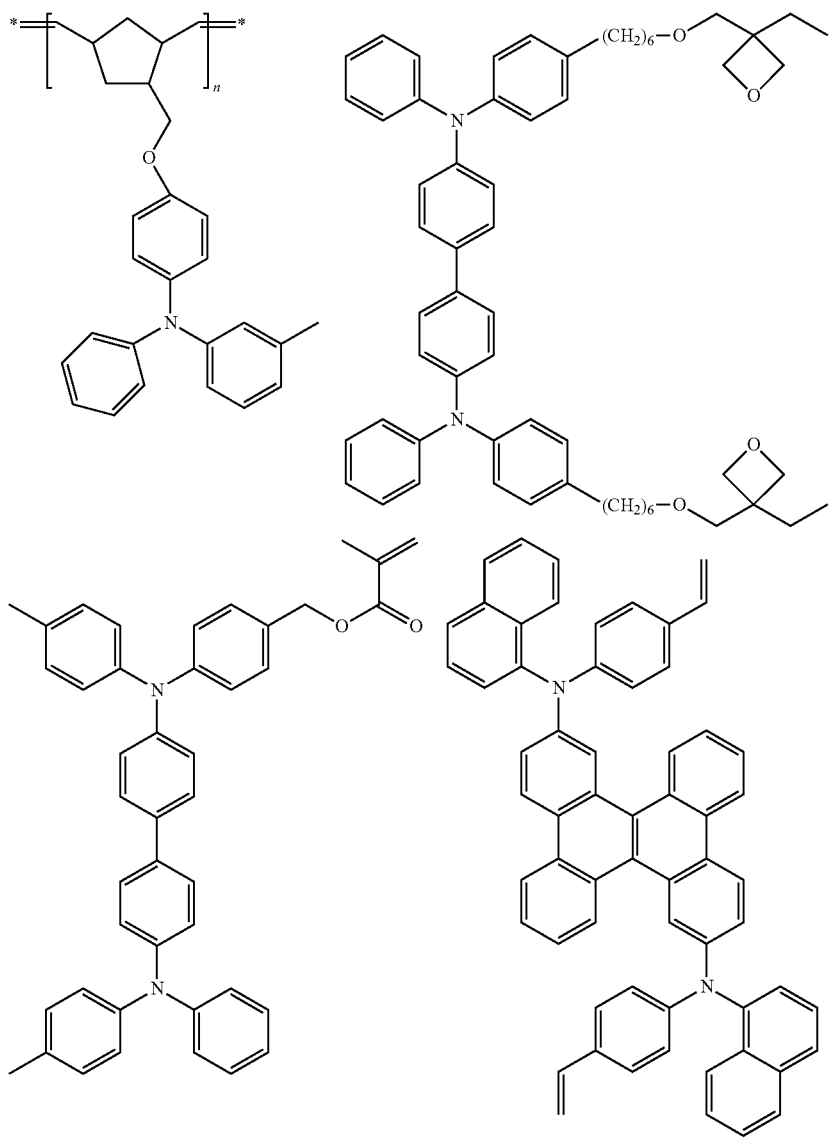

-continued
R =
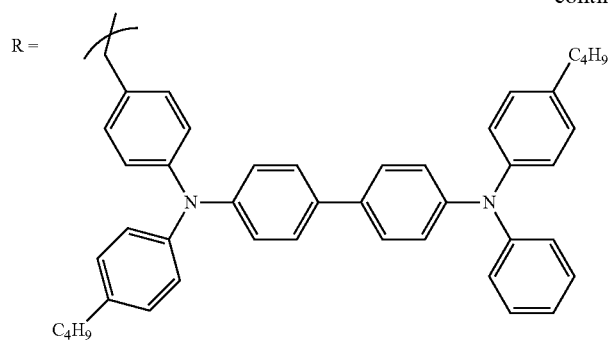
[Chem. 30]
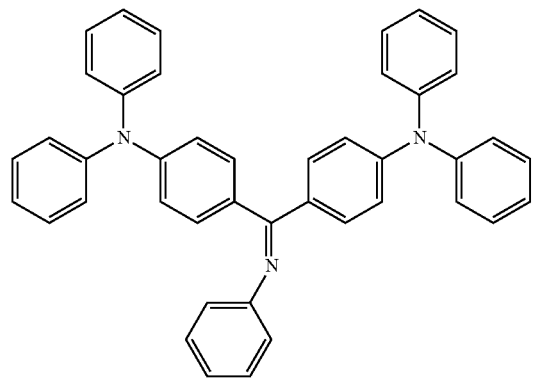
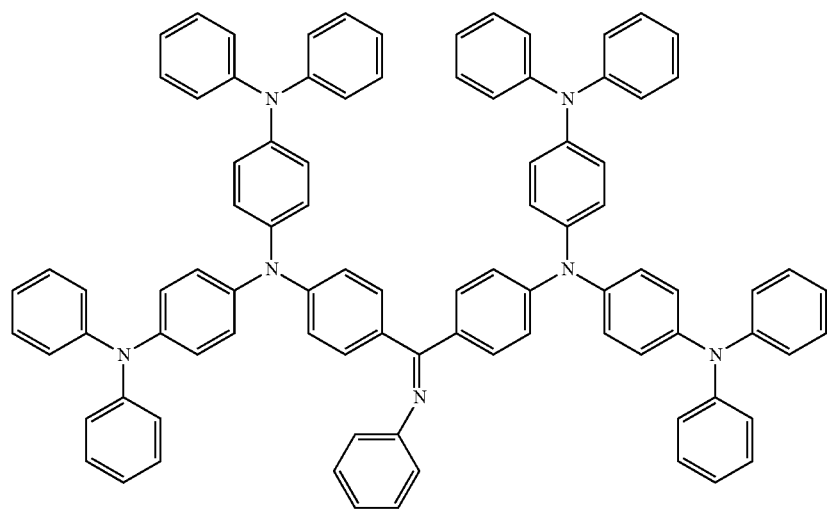

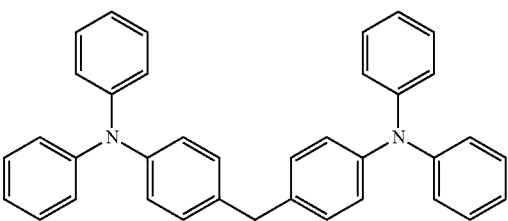
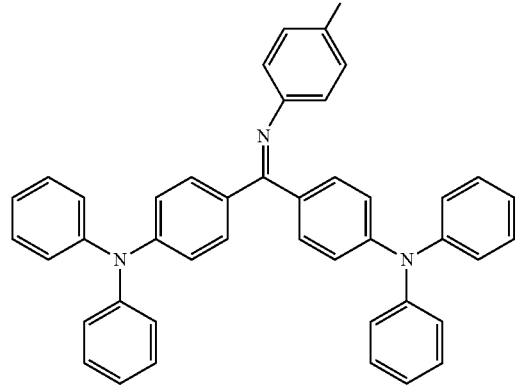
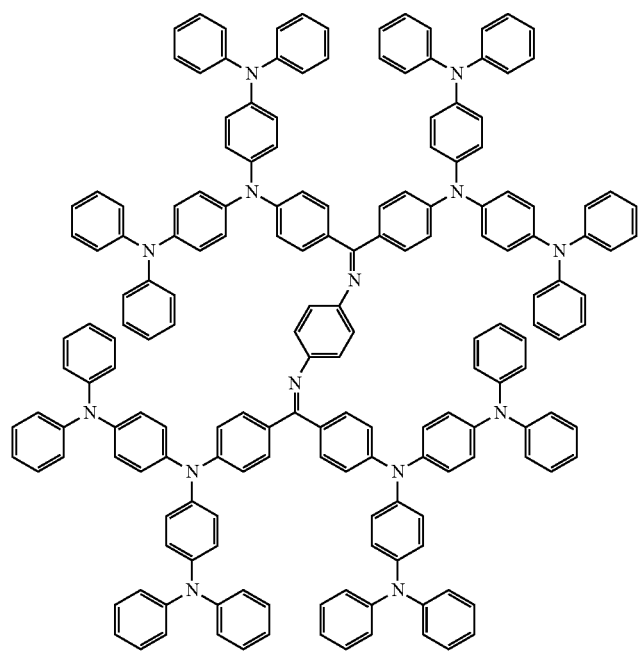 [SMILES: c1ccc(N(c2ccccc2)c2ccc(N(c3ccc(C(=Nc4ccc(N=C(c5ccc(N(c6ccc(N(c7ccccc7)c7ccccc7)cc6)c6ccc(N(c7ccccc7)c7ccccc7)cc6)cc5)c5ccc(N(c6ccc(N(c7ccccc7)c7ccccc7)cc6)c6ccc(N(c7ccccc7)c7ccccc7)cc6)cc5)cc4)c4ccc(N(c5ccc(N(c6ccccc6)c6ccccc6)cc5)c5ccc(N(c6ccccc6)c6ccccc6)cc5)cc4)cc3)c3ccc(N(c4ccccc4)c4ccccc4)cc3)cc2)cc1]

Preferred examples of a compound that may be used as the electron barrier material are shown below.
[Chem. 31]
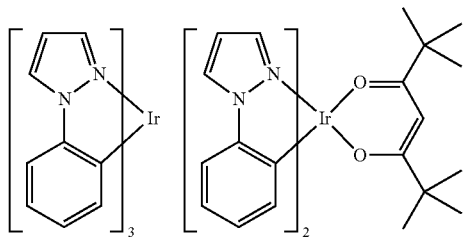
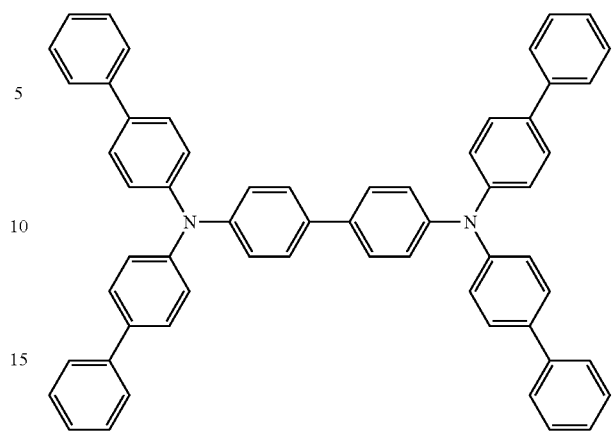
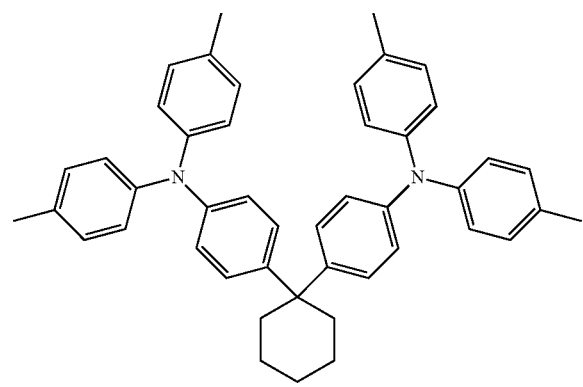
Preferred examples of a compound that may be used as the hole barrier material are shown below.
[Chem. 32]
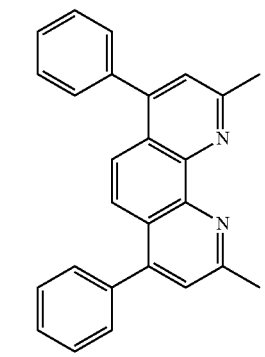
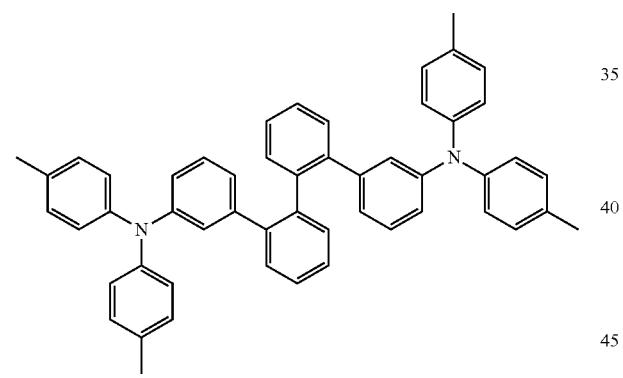
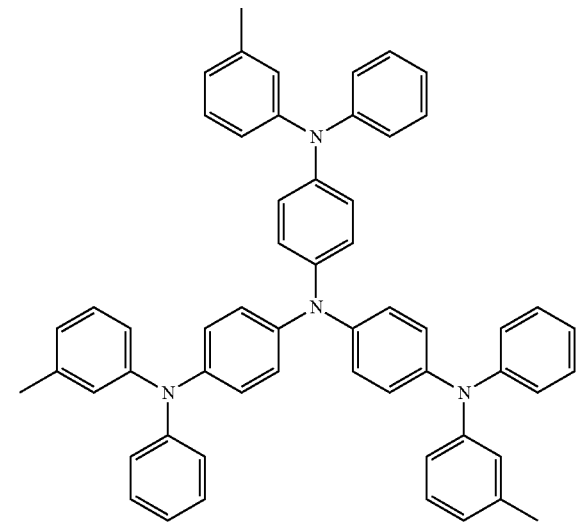
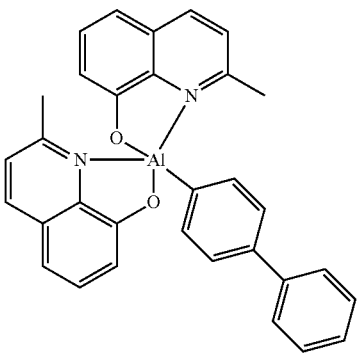

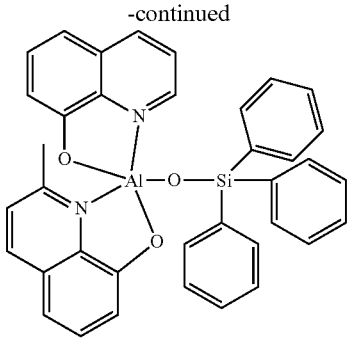
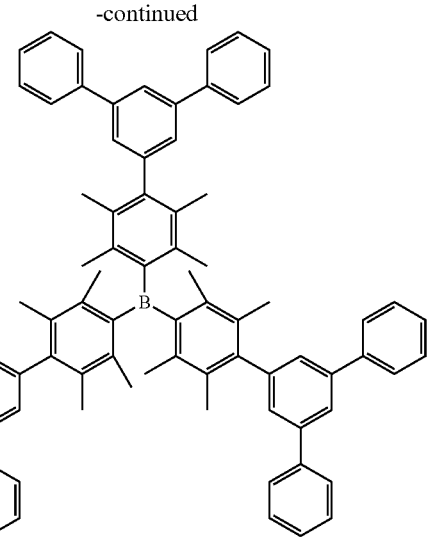
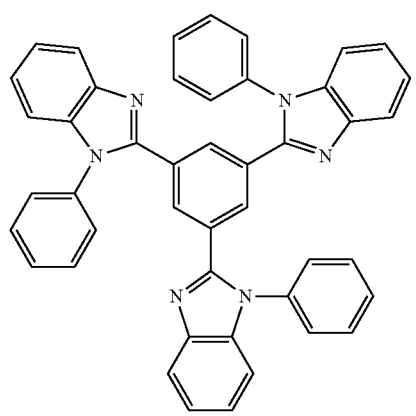
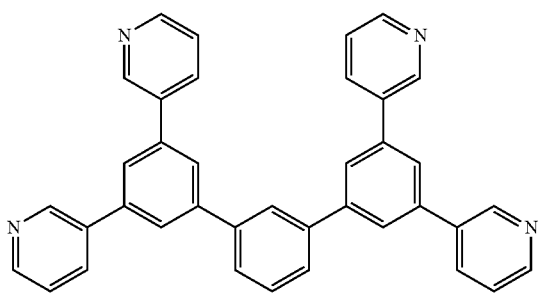
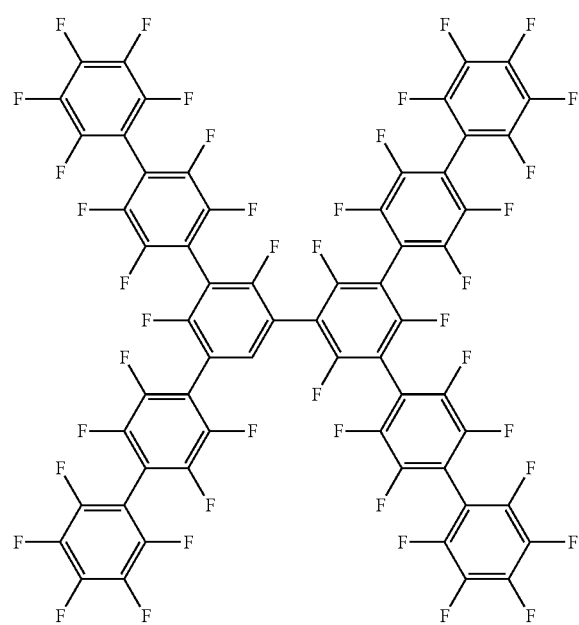
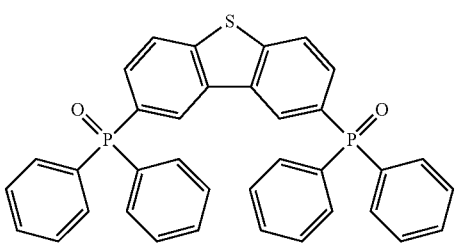
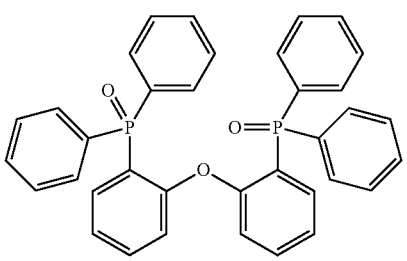 [SMILES: O=P(c1ccccc1)(c1ccccc1)c1ccccc1Oc1ccccc1P(=O)(c1ccccc1)c1ccccc1]
Preferred examples of a compound that may be used as the electron transporting material are shown below.

[Chem. 33]
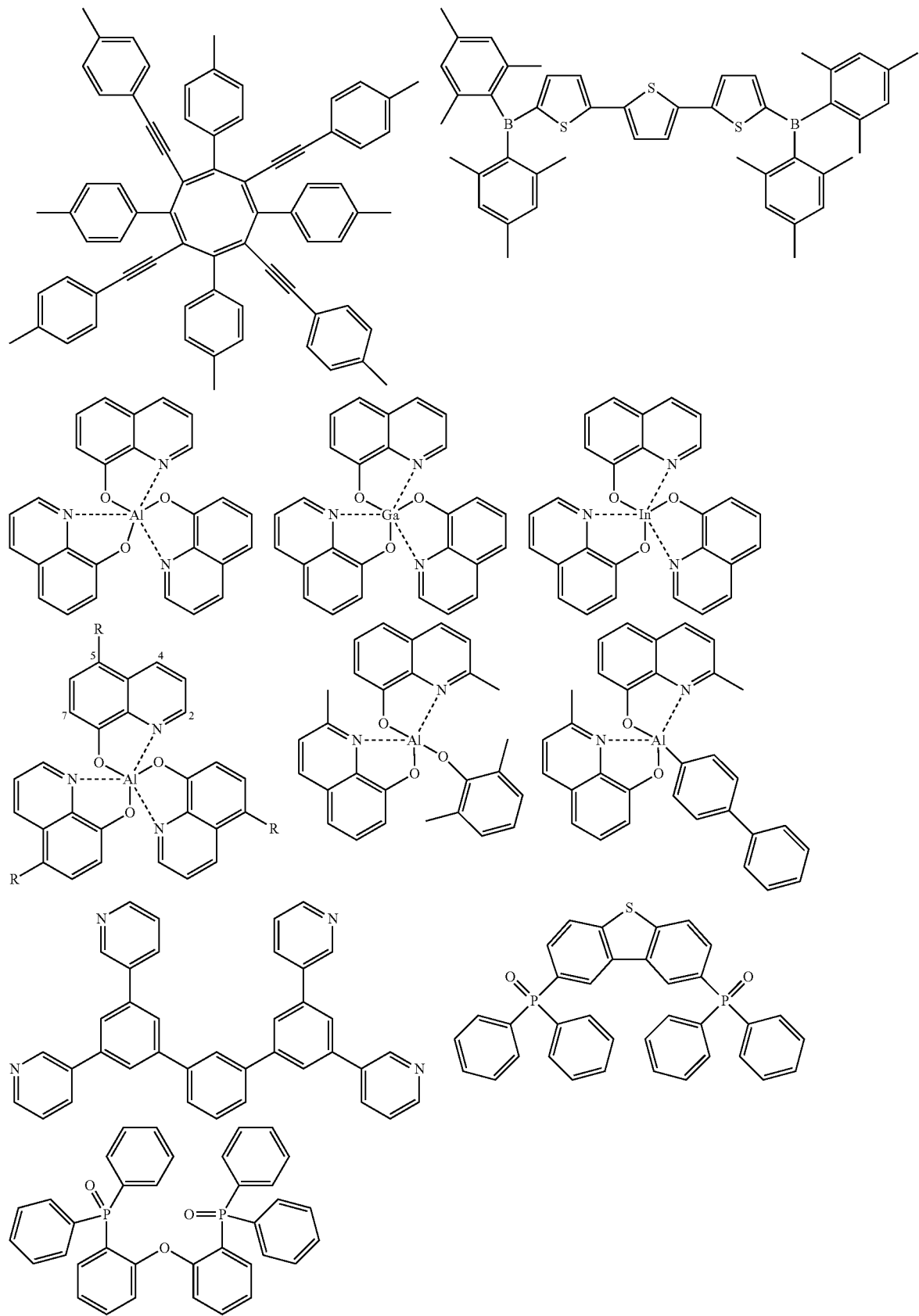

[Chem. 34]
-continued
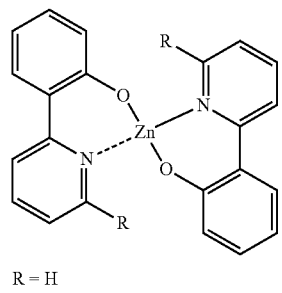
R = H
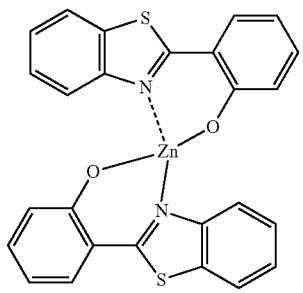
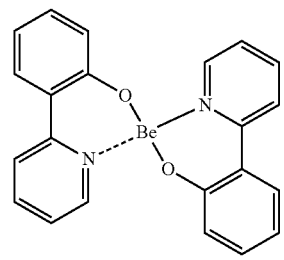
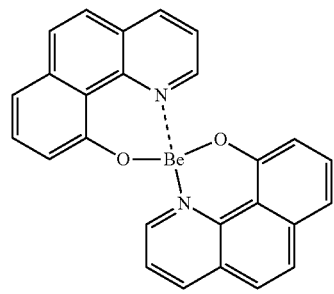
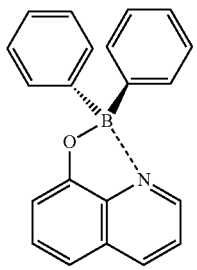
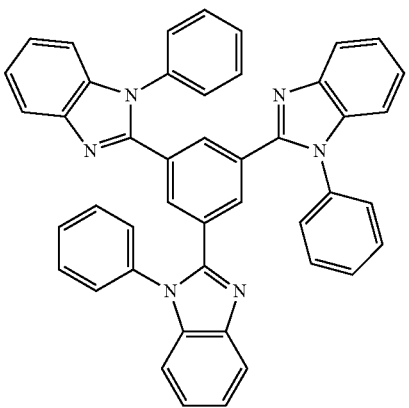
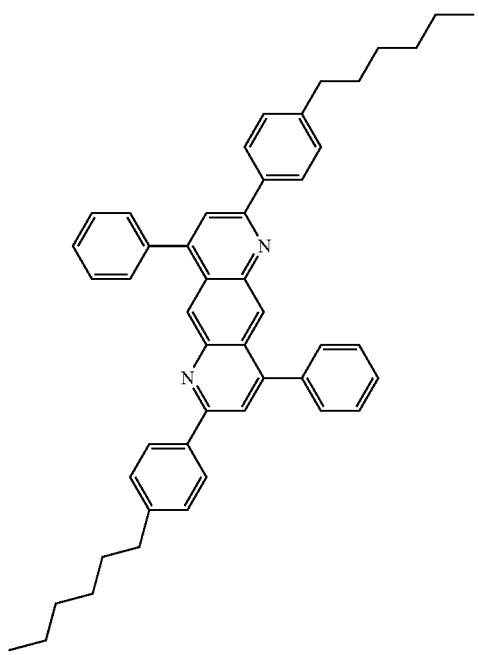

143
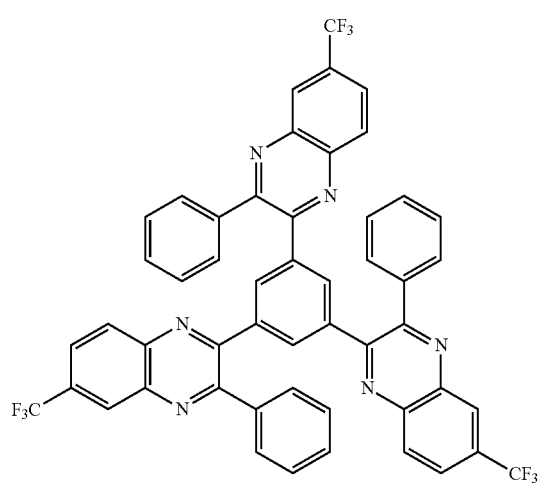
144
-continued
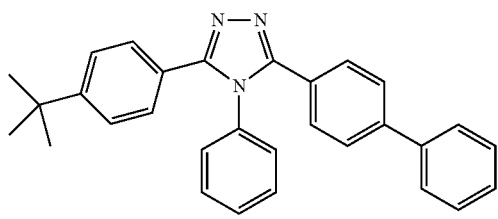
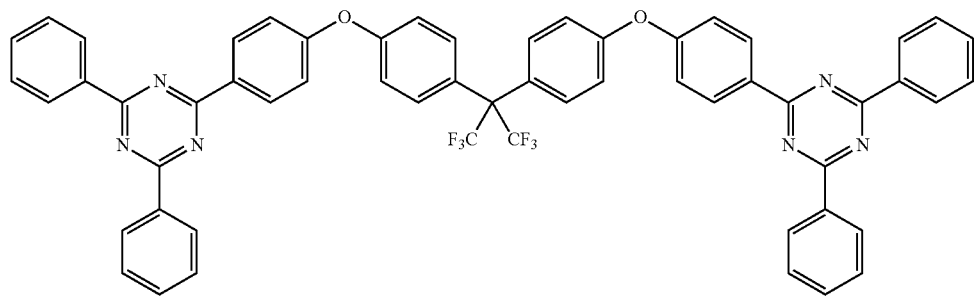
[Chem. 35]
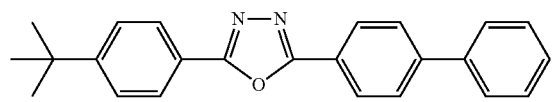
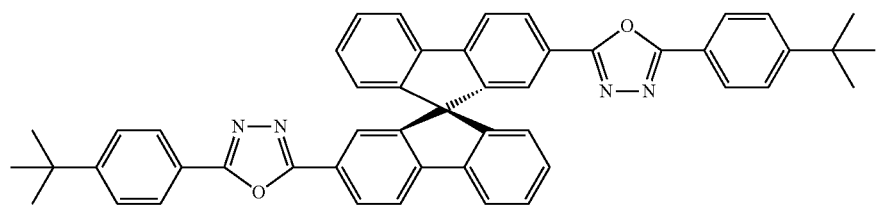

-continued
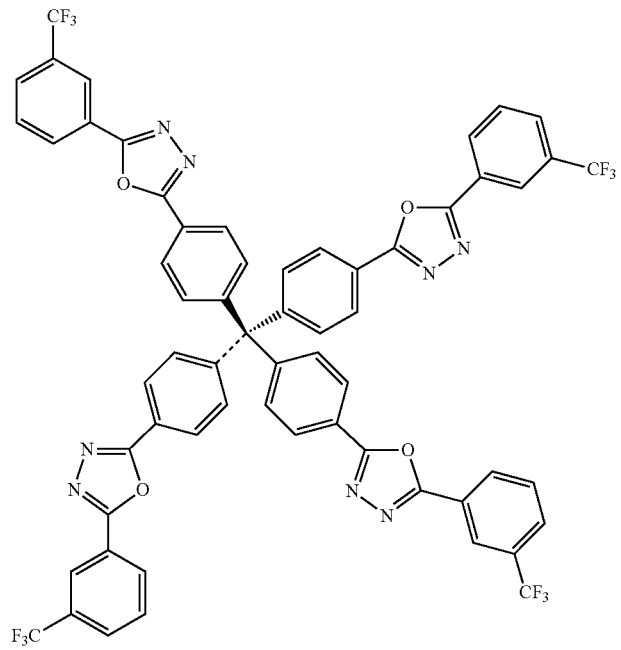
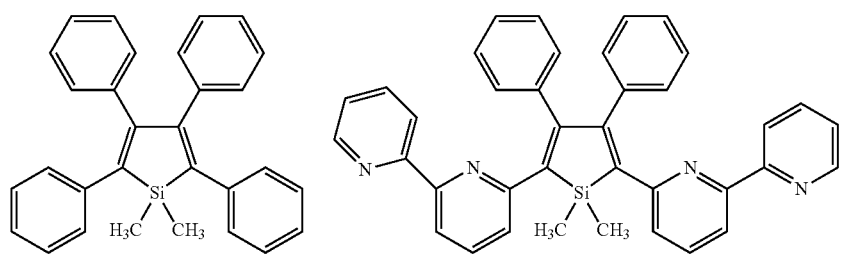
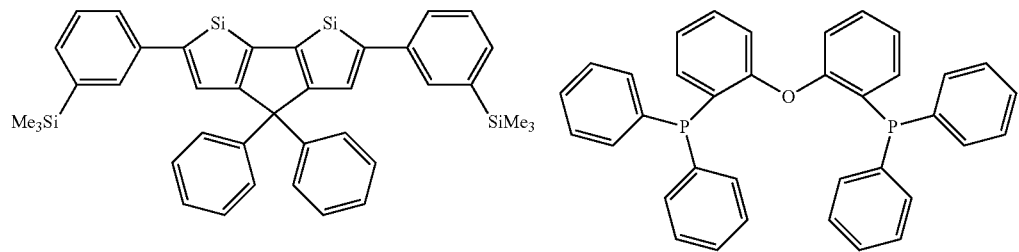
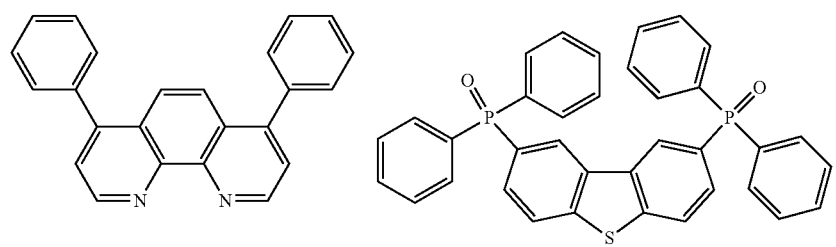

Preferred examples of a compound that may be used as the electron injection material are shown below.

[Chem. 36]

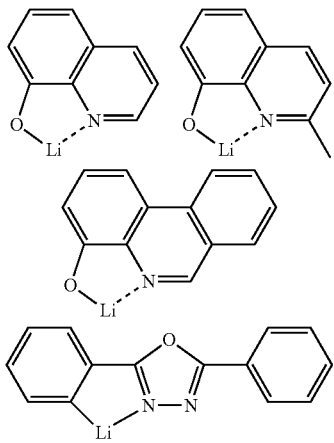

Preferred examples of a compound as a material that may be added are shown below. For example, the compound may be added as a stabilizing material.

[Chem. 37]

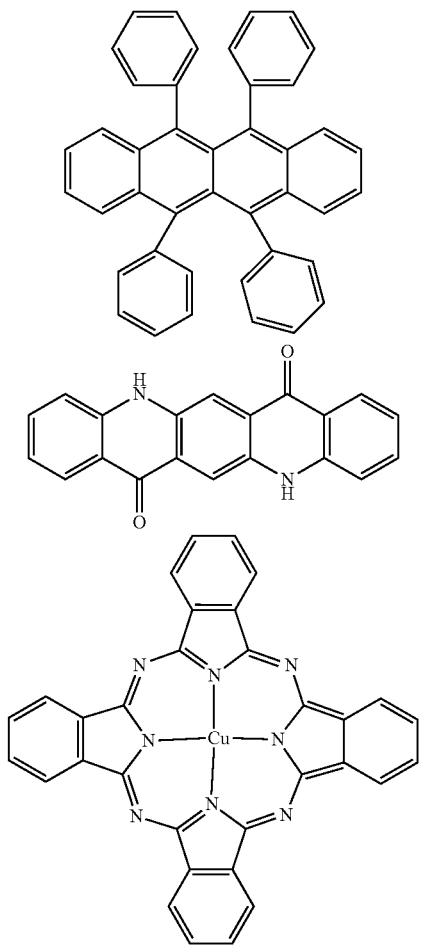

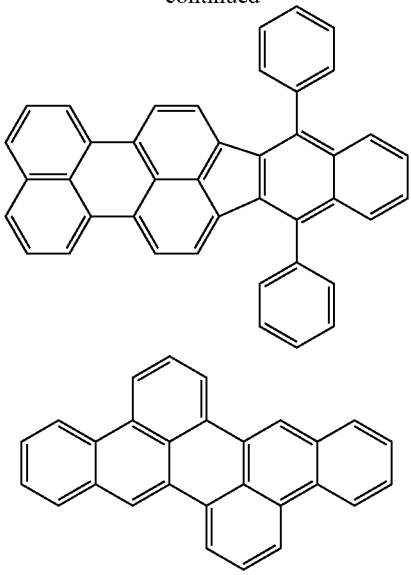

The organic electroluminescent device thus produced by the aforementioned method emits light on application of an electric field between the anode and the cathode of the device. In this case, when the light emission is caused by the excited single energy, light having a wavelength that corresponds to the energy level thereof may be confirmed as fluorescent light and delayed fluorescent light. When the light emission is caused by the excited triplet energy, light having a wavelength that corresponds to the energy level thereof may be confirmed as phosphorescent light. The normal fluorescent light has a shorter light emission lifetime than the delayed fluorescent light, and thus the light emission lifetime may be distinguished between the fluorescent light and the delayed fluorescent light.

The phosphorescent light may substantially not observed with a normal organic compound, such as the compound of the invention, at room temperature since the excited triplet energy is converted to heat or the like due to the instability thereof, and is immediately deactivated with a short lifetime. The excited triplet energy of the normal organic compound may be measured by observing light emission under an extremely low temperature condition.

The organic electroluminescent device of the invention may be applied to any of a single device, a device having a structure with plural devices disposed in an array, and a device having anodes and cathodes disposed in an X-Y matrix. According to the invention, an organic light-emitting device that is largely improved in light emission efficiency may be obtained by adding the compound represented by the general formula (1) in the light-emitting layer. The organic light-emitting device, such as the organic electroluminescent device, of the invention may be applied to a further wide range of purposes. For example, an organic electroluminescent display apparatus may be produced with the organic electroluminescent device of the invention, and for the details thereof, reference may be made to S. Tokito, C. Adachi and H. Murata, "Yuki EL Display" (Organic EL Display) (Ohmsha, Ltd.). In particular, the organic electroluminescent device of the invention may be applied to organic electroluminescent illumination and backlight which are highly demanded.

Example

The features of the invention will be described more specifically with reference to synthesis examples and working examples below. The materials, processes, procedures and the like shown below may be appropriately modified unless they deviate from the substance of the invention. Accordingly, the scope of the invention is not construed as being limited to the specific examples shown below.

Synthesis Example 1

In this synthesis example, a compound 1 was synthesized according to the following scheme. Cz represents a 9-carbazolyl group.

[Chem. 38]

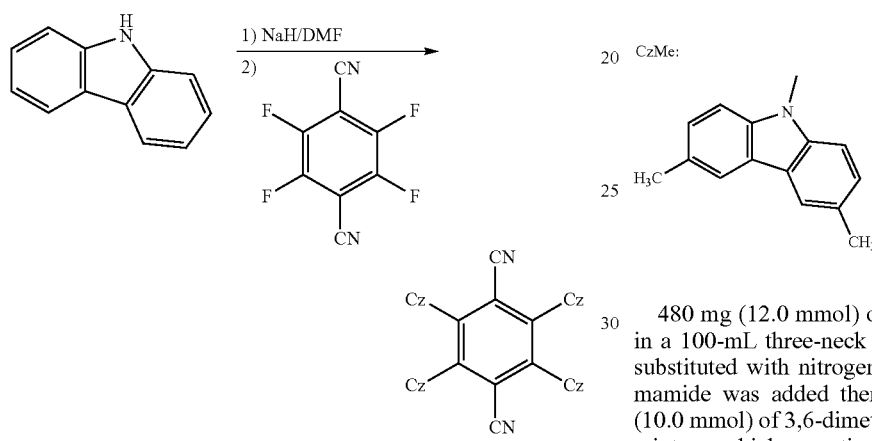

480 mg (12.0 mmol) of 60% sodium hydride was placed in a 100-mL three-neck flask, the interior of the flask was substituted with nitrogen, and 80 mL of N,N-dimethylformamide was added thereto, followed by stirring. 1.67 g (10.0 mmol) of 9H-carbazole was added to the mixture, which was stirred under a nitrogen stream at room temperature for 30 minutes. After stirring, 400 mg (2.00 mmol) of tetrafluoroterephthalonitrile was added to the mixture, and the mixture was stirred under a nitrogen atmosphere at 60° C. for 10 hours. After stirring, 5.0 mL of water was added to the mixture, which was then stirred. After stirring, N,N-dimethylformamide was removed from the mixture. After the removal, 200 mL of water was added to the mixture, to which ultrasonic waves were applied. After the application, the mixture was suction-filtered to provide a solid matter. The resulting solid matter was purified by silica gel column chromatography. In the column chromatography, chloroform was firstly used as a developing solvent, and then acetone was used as a developing solvent. The resulting fraction was concentrated to provide a solid matter, which was then rinsed with a mixed solvent of chloroform and acetone, thereby providing a yellow powdered solid matter in a yield amount of 1.05 g and a yield of 66.5%.

$^1$H-NMR (500 MHz, DMSO-d$_6$, ppm): δ 7.93-7.89 (m, 16H), 7.26 (t, J=7.8 Hz, 8H), 7.16 (t, J=7.8 Hz, 8H)

Elemental analysis: calculated: C, 85.26, H, 4.09, N, 10.65; found: C, 85.28, H, 4.11, N, 10.61.

Synthesis Example 2

In this synthesis example, a compound 4 was synthesized according to the following scheme.

[Chem. 39]

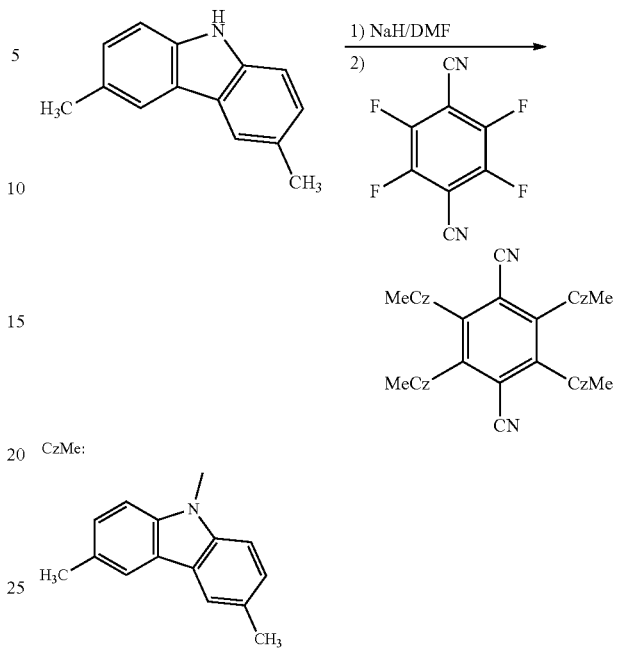

480 mg (12.0 mmol) of 60% sodium hydride was placed in a 100-mL three-neck flask, the interior of the flask was substituted with nitrogen, and 40 mL of N,N-dimethylformamide was added thereto, followed by stirring. 1.95 g (10.0 mmol) of 3,6-dimethyl-9H-carbazole was added to the mixture, which was stirred under a nitrogen stream at room temperature for 30 minutes. After stirring, 400 mg (2.00 mmol) of tetrafluoroterephthalonitrile was added to the mixture, and the mixture was stirred under a nitrogen stream at 60° C. for 10 hours. After stirring, the mixture was added to 400 mL of water, which was then stirred. After stirring, the mixture was suction-filtered to provide a solid matter. The resulting solid matter was rinsed with methanol, thereby providing an orange powdered solid matter in a yield amount of 1.68 g and a yield of 93.2%.

$^1$H NMR (500 MHz, DMSO-d$_6$, ppm): δ 7.81 (d, J=8.5 Hz, 8H), 7.71 (s, 8H), 7.11 (d, J=8.5 Hz, 8H), 2.37 (s, 24H)

Elemental analysis: calculated for C$_{64}$H$_{48}$N$_6$: C, 85.30, H, 5.37, N, 9.33%; found: C, 85.39, H, 5.36, N, 9.35%.

Synthesis Example 3

In this synthesis example, a compound 6 was synthesized according to the following scheme.

[Chem. 40]

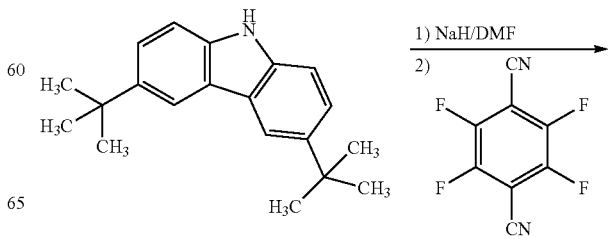

151
-continued

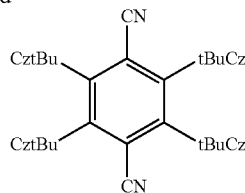

tBuCz:

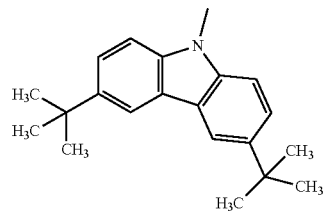

480 mg (12.0 mmol) of 60% sodium hydride was placed in a 100-mL three-neck flask, the interior of the flask was substituted with nitrogen, and 40 mL of N,N-dimethylformamide was added thereto, followed by stirring. 2.79 g (10.0 mmol) of 3,6-di-tert-butyl-9H-carbazole was added to the mixture, which was stirred under a nitrogen stream at room temperature for 30 minutes. After stirring, 400 mg (2.00 mmol) of tetrafluoroterephthalonitrile was added to the mixture, and the mixture was stirred under a nitrogen atmosphere at 60° C. for 1.0 hours. After stirring, the mixture was added to 400 mL of water, which was then stirred. After stirring, the mixture was suction-filtered to provide a solid matter. The resulting solid matter was purified by silica gel column chromatography. In the column chromatography, chloroform was firstly used as a developing solvent, and then acetone was used as a developing solvent. The resulting fraction was concentrated to provide a solid matter, which was then rinsed with a mixed solvent of chloroform and acetone, thereby providing an orange powdered solid matter in a yield amount of 400 mg and a yield of 16.1%.

$^1$H NMR (500 MHz, DMSO-$d_6$, ppm): δ 7.77 (d, J=1.5 Hz, 8H), 7.43 (d, J=8.5 Hz, 8H), 7.08 (dd, J=8.8 Hz, 1.5 Hz, 8H), 1.35 (s, 72H)

Elemental analysis: calculated for $C_{38}H_{36}N_6$: C, 85.39, H, 7.82, N, 6.79%; found: C, 85.38, H, 7.82, N, 6.78%.

Synthesis Example 4

In this synthesis example, a compound 301 was synthesized according to the following scheme.

[Chem. 41]

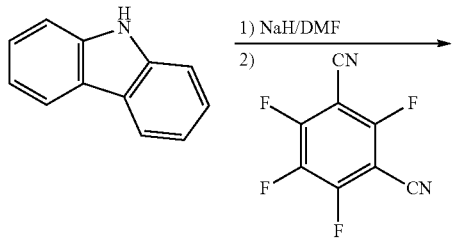

152
-continued

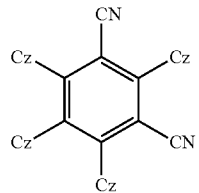

480 mg (12.0 mmol) of 60% sodium hydride was placed in a 100-mL three-neck flask, the interior of the flask was substituted with nitrogen, and 40 mL of N,N-dimethylformamide was added thereto, followed by stirring. 1.67 g (10.0 mmol) of 9H-carbazole was added to the mixture, which was stirred under a nitrogen stream at room temperature for 30 minutes. After stirring, 400 mg (2.00 mmol) of tetrafluoroisophthalonitrile was added to the mixture, and the mixture was stirred under a nitrogen atmosphere at 60° C. for 10 hours. After stirring, 5.0 mL of water was added to the mixture, which was then stirred. After stirring, N,N-dimethylformamide was removed from the mixture. After the removal, 200 mL of water was added to the mixture, to which ultrasonic waves were applied. After the application, the mixture was suction-filtered to provide a solid matter. The resulting solid matter was purified by silica gel column chromatography. In the column chromatography, a mixed solvent of chloroform and hexane (1/5) was firstly used as a developing solvent, and then a mixed solvent of chloroform and hexane (1/2) was used as a developing solvent. The resulting fraction was concentrated to provide a solid matter, which was then recrystallized from a mixed solvent of acetone and hexane, thereby providing a yellow powdered solid matter in a yield amount of 311 mg and a yield of 19.7%.

$^1$H NMR (500 MHz, acetone-$d_6$, ppm): δ 8.33 (d, J=7.7 Hz, 2H), 8.06 (d, J=8.2 Hz, 2H), 7.84-7.82 (m, 4H), 7.71-7.66 (m, 6H), 7.49-7.45 (m, 4H), 7.43 (d, J=7.6 Hz, 2H), 7.14-7.08 (m, 8H), 6.816 (t, J=7.3 Hz, 2H), 6.71 (t, J=7.7 Hz, 2H)

Elemental analysis: calculated: C, 85.26, H, 4.09, N, 10.65; found: C, 85.22, H, 4.03, N, 10.62.

Synthesis Example 5

In this synthesis example, a compound 392 was synthesized according to the following scheme.

[Chem. 42]

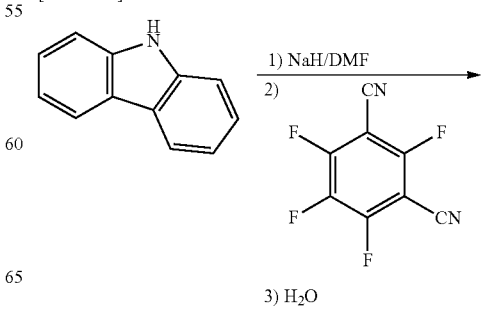

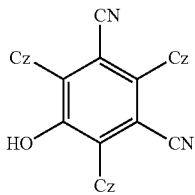

480 mg (12.0 mmol) of 60% sodium hydride was placed in a 100-mL three-neck flask, the interior of the flask was substituted with nitrogen, and 40 mL of N,N-dimethylformamide was added thereto, followed by stirring. 1.67 g (10.0 mmol) of 9H-carbazole was added to the mixture, which was stirred under a nitrogen stream at room temperature for 30 minutes. After stirring, 400 mg (2.00 mmol) of tetrafluoroisophthalonitrile was added to the mixture, and the mixture was stirred under a nitrogen atmosphere at 60° C. for 10 hours. After stirring, 5.0 mL of water was added to the mixture, which was then stirred. After stirring, N,N-dimethylformamide was removed from the mixture. After the removal, 200 mL of water was added to the mixture, to which ultrasonic waves were applied. After the application, the mixture was suction-filtered to provide a solid matter. The resulting solid matter was purified by silica gel column chromatography. In the column chromatography, chloroform was firstly used as a developing solvent, and then a mixed solvent of chloroform and acetone (1/2) was used as a developing solvent. The resulting fraction was concentrated to provide a solid matter, which was then rinsed with methanol, thereby providing a pale yellow powdered solid matter in a yield amount of 600 mg and a yield of 46.9%.

Synthesis Example 6

In this synthesis example, a compound 501 was synthesized according to the following scheme. Cz represents a 9-carbazolyl group.

[Chem. 43]

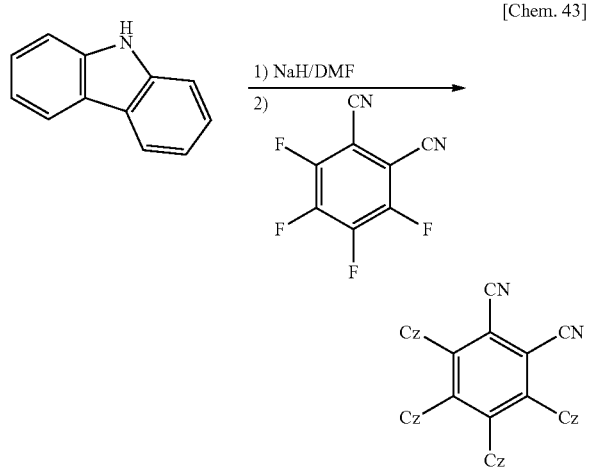

480 mg (12.0 mmol) of 60% sodium hydride was placed in a 100-mL three-neck flask, the interior of the flask was substituted with nitrogen, and 40 mL of N,N-dimethylformamide was added thereto, followed by stirring. 1.67 g (10.0 mmol) of 9H-carbazole was added to the mixture, which was stirred under a nitrogen stream at room temperature for 30 minutes. After stirring, 400 mg (2.00 mmol) of tetrafluorophthalonitrile was added to the mixture, and the mixture was stirred under a nitrogen atmosphere at 60° C. for 10 hours. After stirring, 5.0 mL of water was added to the mixture, which was then stirred. After stirring, N,N-dimethylformamide was removed from the mixture. After the removal, 200 mL of water was added to the mixture, to which ultrasonic waves were applied. After the application, the mixture was suction-filtered to provide a solid matter. The resulting solid matter was purified by silica gel column chromatography. In the column chromatography, chloroform was firstly used as a developing solvent, and then a mixed solvent of acetone and chloroform (1/2) was used as a developing solvent. The resulting fraction was concentrated to provide a solid matter, which was then recrystallized from a mixed solvent of chloroform and methanol, thereby providing a yellow powdered solid matter in a yield amount of 450 mg and a yield of 28.5%.

$^1$H NMR (500 MHz, DMSO-$d_6$, ppm): δ 7.90-7.87 (m, 4H), 7.72-7.70 (m, 4H), 7.40-7.37 (m, 8H), 7.16-7.10 (m, 8H), 6.74 (t, J=7.7 Hz, 4H), 6.60 (t, J=7.7 Hz, 4H)

Elemental analysis: calculated: C, 85.26, H, 4.09, N, 10.65; found: C, 85.16, H, 4.02, N, 10.55.

Synthesis Example 7

In this synthesis example, a compound 504 was synthesized according to the following scheme.

[Chem. 44]

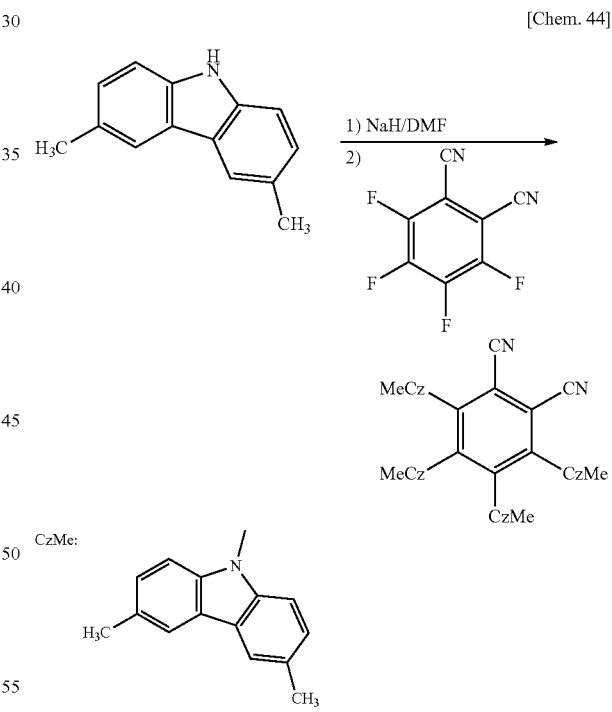

480 mg (12.0 mmol) of 60% sodium hydride was placed in a 100-mL three-neck flask, the interior of the flask was substituted with nitrogen, and 40 mL of N,N-dimethylformamide was added thereto, followed by stirring. 1.95 g (10.0 mmol) of 3,6-dimethyl-9H-carbazole was added to the mixture, which was stirred under a nitrogen stream at room temperature for 30 minutes. After stirring, 400 mg (2.00 mmol) of tetrafluorophthalonitrile was added to the mixture, and the mixture was stirred under a nitrogen atmosphere at 60° C. for 10 hours. After stirring, the mixture was added to 400 mL of water, which was then stirred. After stirring, the mixture was suction-filtered to provide a solid matter. The resulting solid matter was purified by silica gel column chromatography. In the column chromatography, chloroform was firstly used as a developing solvent, and then a mixed solvent of chloroform and acetone (1/2) was used as a developing solvent. The resulting fraction was concentrated to provide a solid matter, which was then rinsed with acetone, thereby providing an orange powdered solid matter in a yield amount of 515 mg and a yield of 28.6%.

$^1$H NMR (500 MHz, DMSO-$d_6$, ppm): δ 7.64 (s, 4H), 7.54 (d, J=8.5 Hz, 4H), 7.27 (d, J=8.5 Hz, 4H), 7.15 (s, 4H), 6.95 (dd, J=8.3 Hz, 1.5 Hz, 4H), 6.44 (dd, J=8.5 Hz, 2.5 Hz, 4H), 2.34 (s, 12H), 2.10 (s, 12H)

Elemental analysis: calculated: C, 85.30, H, 5.37, N, 9.33; found: C, 85.34, H, 5.35, N, 9.30.

Synthesis Example 8

In this synthesis example, a compound 901 was synthesized according to the following scheme.

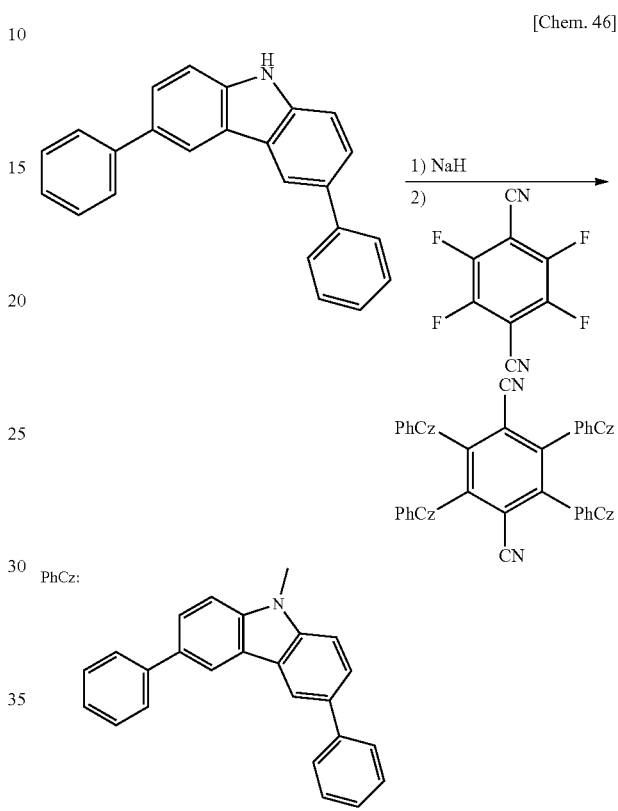

[Chem. 45]

480 mg (12.0 mmol) of 60% sodium hydride was placed in a 100-mL three-neck flask, the interior of the flask was substituted with nitrogen, and 40 mL of N,N-dimethylformamide was added thereto, followed by stirring. 1.71 g (10.0 mmol) of 1,2,3,4-tetrahydrocarbazole was added to the mixture, which was stirred under a nitrogen stream at room temperature for 30 minutes. After stirring, 400 mg (2.00 mmol) of tetrafluoroterephthalonitrile was added to the mixture, and the mixture was stirred under a nitrogen atmosphere at 60° C. for 10 hours. After stirring, the mixture was added to 400 mL of water, which was then stirred. After stirring, the mixture was suction-filtered to provide a solid matter. The resulting solid matter was purified by silica gel column chromatography. In the column chromatography, chloroform was firstly used as a developing solvent, and then acetone was used as a developing solvent. The resulting fraction was concentrated to provide a solid matter, which was then rinsed with a mixed solvent of chloroform and acetone, thereby providing an orange powdered solid matter in a yield amount of 120 mg and a yield of 7.4%.

Synthesis Example 9

In this synthesis example, a compound 252 was synthesized according to the following scheme.

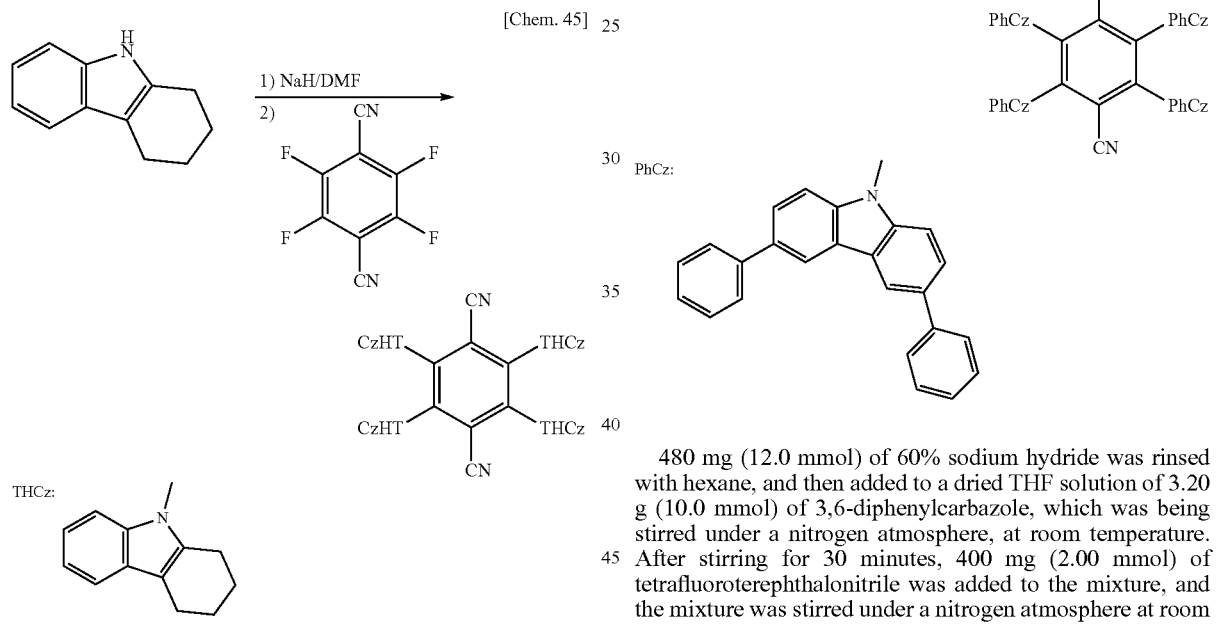

[Chem. 46]

480 mg (12.0 mmol) of 60% sodium hydride was rinsed with hexane, and then added to a dried THF solution of 3.20 g (10.0 mmol) of 3,6-diphenylcarbazole, which was being stirred under a nitrogen atmosphere, at room temperature. After stirring for 30 minutes, 400 mg (2.00 mmol) of tetrafluoroterephthalonitrile was added to the mixture, and the mixture was stirred under a nitrogen atmosphere at room temperature for 10 hours. Thereafter, the reaction was terminated with 5 mL of water, and the mixture was concentrated under reduced pressure to provide a yellow solid matter. The resulting solid matter was purified by silica gel chromatography with chloroform as a developing solvent, thereby providing an orange powdered solid matter in a yield amount of 2.20 g and a yield of 79%.

$^1$H NMR (500 MHz, DMSO-$d_6$, ppm): δ 8.37 (d, J=1.5 Hz, 8H), 8.05 (d, J=8.5 Hz, 8H), 7.70 (m, 16H), 7.62 (dd, J=8.5, 1.5 Hz, 8H), 7.45 (m, 16H), 7.36 (m, 8H)

IR (KBr, cm$^{-1}$): 2,236, 2,228, 1,600, 1,476, 1,456, 1,441, 1,290, 1,226

MALDI-TOFMS (m/z): [M]$^+$ $C_{104}H_{64}N_6$: calculated: 1,396.52; found: 1,396.66.

Elemental analysis: calculated: C, 89.37, H, 4.62, N, 6.01; found: C, 89.26, H, 4.53, N, 5.95.

Synthesis Example 10

In this synthesis example, a compound 523 was synthesized according to the following scheme.

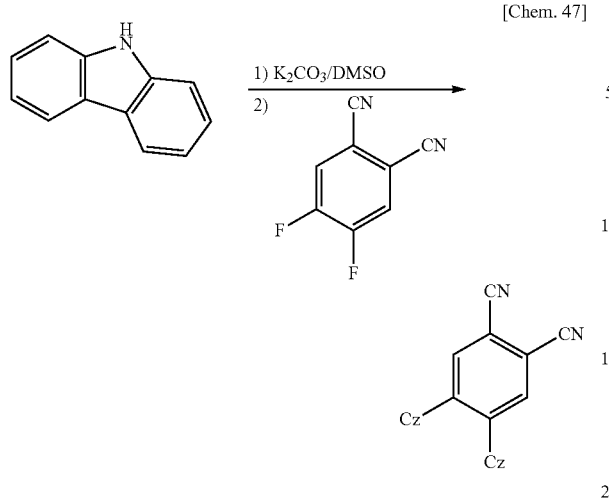

1.52 g (9.14 mmol) of 9H-carbazole and 1.91 g (13.7 mmol) of potassium carbonate were placed in a 50-mL recovery flask, and the interior of the flask was substituted with nitrogen. 15 mL of dimethylsulfoxide was added to the mixture, which was stirred under a nitrogen stream at room temperature for 1 hour. 0.500 g (3.05 mmol) of 4,5-difluorophthalonitrile was added to the mixture. The mixture was stirred under a nitrogen stream at room temperature for 3 hours and then at 50° C. for 20 hours. Thereafter, the mixture was added to water, followed by stirring. The mixture was extracted with toluene. After the extraction, the extracted solution was rinsed with a saturated sodium chloride aqueous solution. After rinsing, an organic layer and an aqueous layer were separated, and the organic layer was dried by adding magnesium sulfate thereto. After drying, the mixture was suction-filtered to provide a filtrate. The resulting filtrate was concentrated to provide a solid matter, which was purified by silica gel column chromatography. In the purification, a mixed solvent of toluene and hexane (1/4) was firstly used as a developing solvent, then a mixed solvent of toluene and hexane (7/3) was used, and then toluene was used as a developing solvent (the developing ratio was gradually changed). The resulting fraction was concentrated to provide a solid matter, which was then rinsed by reslurry with a mixed solvent of acetone and methanol, thereby providing a pale yellow powdered solid matter in a yield amount of 1.20 g and a yield of 85.8%.

$^1$H NMR (500 MHz, acetone-$d_6$, ppm): δ 8.73 (s, 2H), 7.91-7.89 (m, 4H), 7.40-7.38 (m, 4H), 7.13-7.09 (m, 8H)

MS (MALDI): m/z calculated: 458.15 [M+H]$^+$; found: 458.12.

Synthesis Example 11

In this synthesis example, a compound 31 was synthesized according to the following scheme.

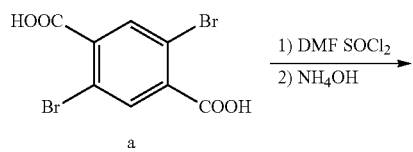

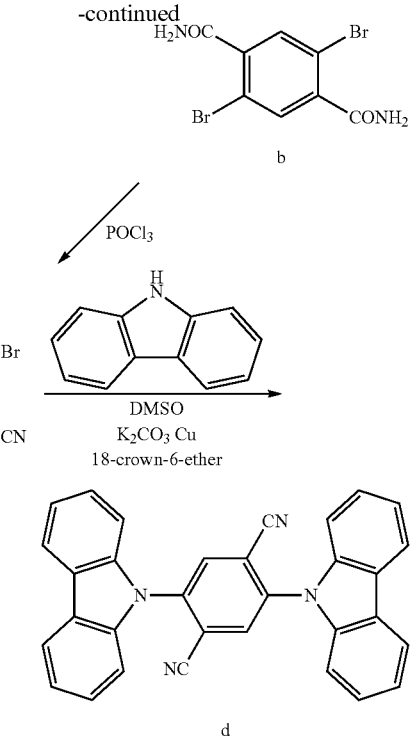

The compound b and the compound c were synthesized in the same manner as in J.-Z. Cheng et al., tetrahedron, 67 (2011), 734.

2,5-Dibromoterephthalonitrile as the compound c (1.44 g, 5.0 mol), 9H-carbazole (1.89 q, 11.3 mol), copper powder 0.64 g, 10 mol), potassium carbonate (2.79 g, 20 mol), 18-crown-6 (0.25 g, 0.94 mol) and DMSO (5 mL) were placed in a two-neck flask under a nitrogen atmosphere, and stirred at 140° C. for 9 hours. Thereafter, impurities were removed from the reaction product by dissolving the product in chloroform, followed by filtering, and the reaction product was rinsed with water and dried over magnesium sulfate. Thereafter, the reaction product was purified by column chromatography (chloroform), thereby providing yellow powder in a yield amount of 0.53 g and a yield of 23%.

Synthesis Example 12

In this synthesis example, a compound 716 was synthesized according to the following scheme.

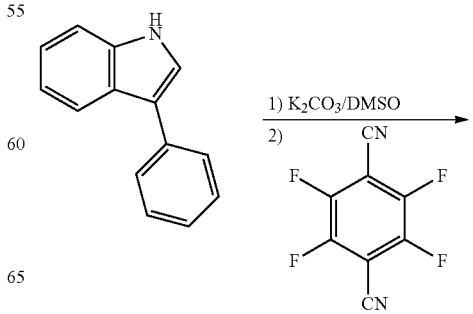

-continued

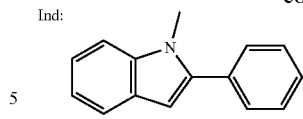

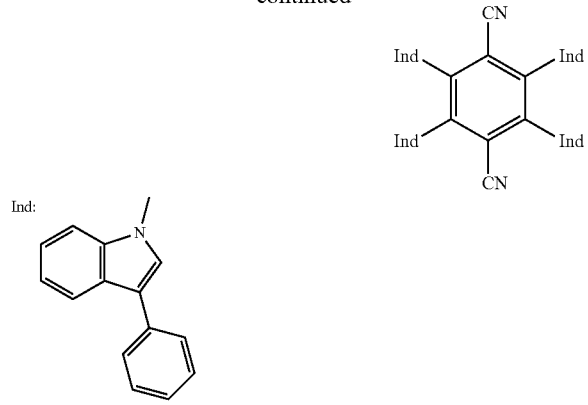

4.01 g (20.8 mmol) of 3-phenyl-1H-indole and 5.72 g (41.4 mmol) of potassium carbonate were placed in a 50 mL three-neck flask, and the interior of the flask was substituted by nitrogen. 20 mL of dimethylsulfoxide was added to the mixture, which was then stirred at room temperature for 1 hour. After cooling the mixture with an ice bath, 0.696 g (3.49 mmol) of tetrafluoroterephthalonitrile was added to the mixture, and the mixture was then stirred at a temperature of 0° C., which was gradually increased to room temperature. The mixture was stirred under a nitrogen atmosphere at room temperature for 24 hours. After stirring, the mixture was added to approximately 300 mL of water, followed by stirring. After stirring, the mixture was suction-filtered to provide a solid matter. The resulting solid matter was dissolved and purified by silica gel column chromatography. In the column chromatography, a mixed solvent of toluene and hexane (1/5) was firstly used as a developing solvent, and then toluene was used as a developing solvent. The resulting fraction was concentrated to provide a solid matter, which was then rinsed with a mixed solvent of acetone and methanol, thereby providing an orange powdered solid matter in a yield amount of 2.02 g and a yield of 65.0%.

$^1$H NMR (500 MHz, DMSO-$d_6$, ppm): δ 7.73 (s, 4H), 7.67 (d, J=8.0 Hz, 4H), 7.51-7.33 (m, 24H), 7.09 (t, J=7.8 Hz, 4H), 7.02 (t, J=7.5 Hz, 4H)

Synthesis Example 13

In this synthesis example, a compound 728 was synthesized according to the following scheme.

[Chem. 50]

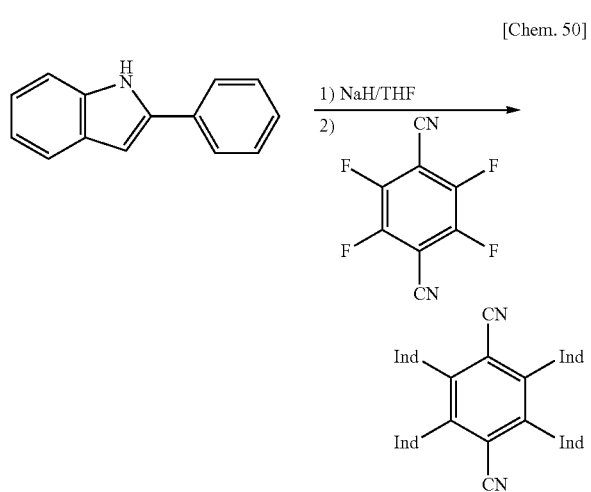

-continued

Ind:

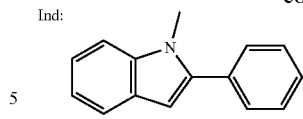

2.40 g (60.0 mmol) of 60% sodium hydride was placed in a 200-mL three-neck flask, the interior of the flask was substituted with nitrogen, and 100 mL of tetrahydrofuran was added thereto, followed by stirring. 9.65 g (50.0 mmol) of 2-phenyl-1H-indole was added to the mixture, which was stirred under a nitrogen stream at room temperature for 30 minutes. 2.00 g (10.0 mmol) of tetrafluoroterephthalonitrile was added to the mixture, and the mixture was stirred under a nitrogen atmosphere at room temperature for 24 hours. After stirring, approximately 50 mL of water was gradually added to the mixture, followed by stirring. After stirring, an organic layer and an aqueous layer were separated, and the aqueous layer was extracted with toluene. The organic layer and the extracted solution were combined to each other and rinsed with a saturated sodium chloride aqueous solution. After rinsing, the organic layer was dried by adding magnesium sulfate thereto. After drying, the mixture was suction-filtered to provide a filtrate. The resulting filtrate was concentrated to provide a solid matter, which was dissolved in chloroform, and the solution was suction-filtered through Celite and silica gel to provide a filtrate. The resulting filtrate was concentrated to provide a solid matter, which was rinsed with isopropanol. After rinsing, the solid matter was rinsed with ethyl acetate, thereby providing an orange powdered solid matter in a yield amount of 1.70 g and a yield of 19.0%.

$^1$H NMR (500 MHz, DMSO-$d_6$, ppm): δ 7.48 (d, J 8.0 Hz, 4H), 7.33 (t, J=7.0 Hz, 4H), 7.26 (t, J=7.0 Hz, 8H), 7.09 (t, J=7.0 Hz, 4H), 6.99 (d, J=8.0 Hz, 4H), 6.81 (t, J=8.0 Hz, 4H), 6.65 (s, 4H), 6.53 (d, J=7.0 Hz, 8H)

Example 1

Figure 2:
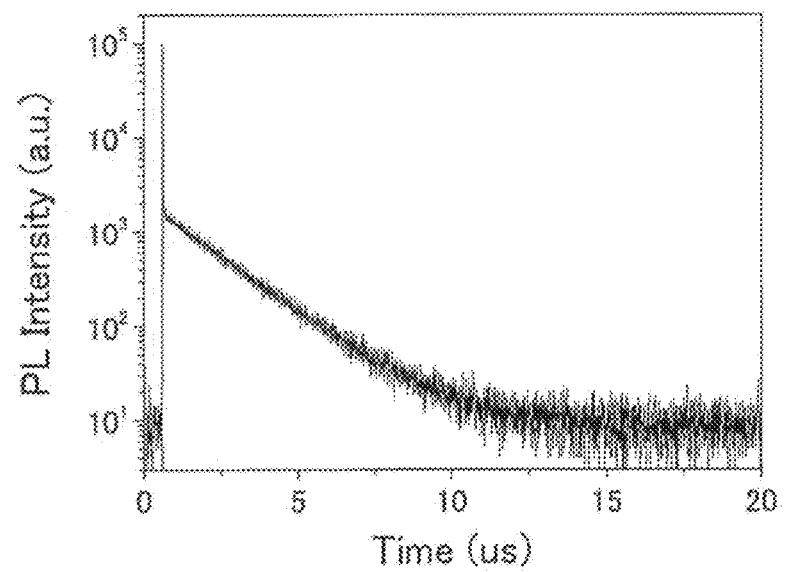
FIG. 2 is a time resolved spectrum of a toluene solution of the compound 1 of Example 1.

In this example, a toluene solution of the compound 1 synthesized in Synthesis Example 1 was prepared and irradiated with light having a wavelength of 280 nm at 300 K under bubbling with nitrogen, and thus the light emission wavelength shown in Table 7 was observed. The time resolved spectrum was obtained with Streak Camera, Model. C4334, produced by Hamamatsu Photonics K.K., and the component with a short light emission lifetime was designated as fluorescent light, whereas the component with a long light emission lifetime was designated as delayed fluorescent light (FIG. 2). The lifetimes of the fluorescent light component and the delayed fluorescent light component were as shown in Table 7.

The results of the same evaluation with the compounds synthesized in Synthesis Examples 2 to 7, instead of the compound 1 are also shown in Table 7. The compound 392 and the compound 901 were measured without bubbling with nitrogen.

TABLE 7

| Compound | Light emission wavelength (nm) | Fluorescent light component (ns) | Delayed fluorescent light component (µs) |
|---|---|---|---|
| Compound 1 | 537 | 8.76 | 1.91 |
| Compound 4 | 556 | 9.58 | 1.53 |
| Compound 6 | 553 | 3.53 | 8.46 |
| Compound 31 | 480 | 22.5 | 65.5 |

TABLE 7-continued

| Compound | Light emission wavelength (nm) | Fluorescent light component (ns) | Delayed fluorescent light component (μs) |
|---|---|---|---|
| Compound 252 | 577 | 9.0 | 1.10 |
| Compound 301 | 508 | 3.77 | 4.89 |
| Compound 392 | 488 | 10.78 | 3.65 |
| Compound 501 | 525 | 12.96 | 13.43 |
| Compound 504 | 521 | 18.81 | 6.57 |
| Compound 523 | 473 | 28.52 | 129.67 |
| Compound 901 | 556 | 10.00 | 3.54 |

In this example, an organic photoluminescent device having a light-emitting layer formed of the compound 1 and a host material was produced and evaluated for the characteristics thereof.

Figure 3:
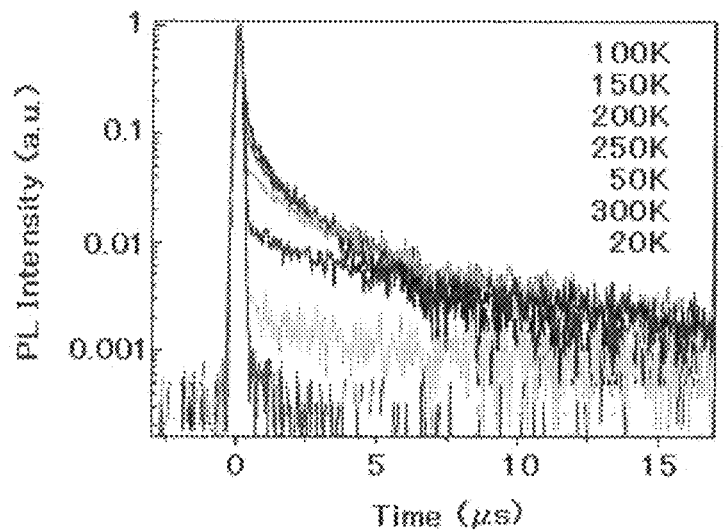
FIG. 3 is a graph showing the change of the light emission lifetime depending on temperature of the organic photoluminescent device using the compound 1 of Example 2.

On a silicon substrate, the compound 1 and mCP were vapor-deposited from separate vapor deposition sources respectively by a vacuum vapor deposition method under condition of a vacuum degree of $5.0\times10^{-6}$ Pa, thereby forming a thin film having a thickness of 100 nm and a concentration of the compound 1 of 6.0% by weight at a rate of 0.3 nm/sec, which was designated as an organic photoluminescent device. The light emission spectrum of the thin film on irradiating the device with light having a wavelength of 337 nm with an $N_2$ laser was evaluated at 300 K with Absolute Quantum Yield Measurement System, Model C9920-02, produced by Hamamatsu Photonics K.K., and thus light emission with a wavelength of 548 nm was observed with a photoluminescence quantum efficiency of 47%. Subsequently, the time resolved spectra on irradiating the device with light having a wavelength of 337 nm with an $N_2$ laser at temperatures of 20 K, 50 K, 100 K, 150 K, 200 K, 250 K and 300 K were evaluated with a streak camera, Model C4334, produced by Hamamatsu Photonics K.K., and the component with a short light emission lifetime was designated as fluorescent light, whereas the component with a long light emission lifetime was designated as delayed fluorescent light. As a result, the fluorescent light component and the delayed fluorescent light component were observed in a range of from 50 to 500 K (FIG. 3). The light emission lifetime of the fluorescent light component was from 12 to 16 nm, and that of the delayed fluorescent light component was 11 μs at 100 K and 8.8 μs at 150 K.

The same test was performed with organic photoluminescent devices produced with the compound 501 and the compound 289 instead of the compound 1, and as a result, the fluorescent light component and the delayed fluorescent light component were similarly observed.

Example 3

In this example, an organic electroluminescent device having a light-emitting layer formed of the compound 1 and CBP was produced and evaluated for the characteristics thereof.

Thin films each were formed by a vacuum vapor deposition method at a vacuum degree of $5.0\times10^{-4}$ Pa on a glass substrate having formed thereon an anode formed of indium tin oxide (ITO) having a thickness of 100 nm. First, α-NPD was formed to a thickness of 35 nm on ITO. The compound 1 and CBP were then vapor-deposited from separate vapor deposition sources respectively to form a layer having a thickness of 15 nm, which was designated as a light-emitting layer. The concentration of the compound 1 herein was 6.0% by weight. TPBi was then formed to a thickness of 65 nm, lithium fluoride (LiF) was further vapor-deposited to a thickness of 0.8 nm, and then aluminum (Al) was vapor-deposited to a thickness of 80 nm, which was designated as a cathode, thereby completing an organic electroluminescent device.

Figure 4:
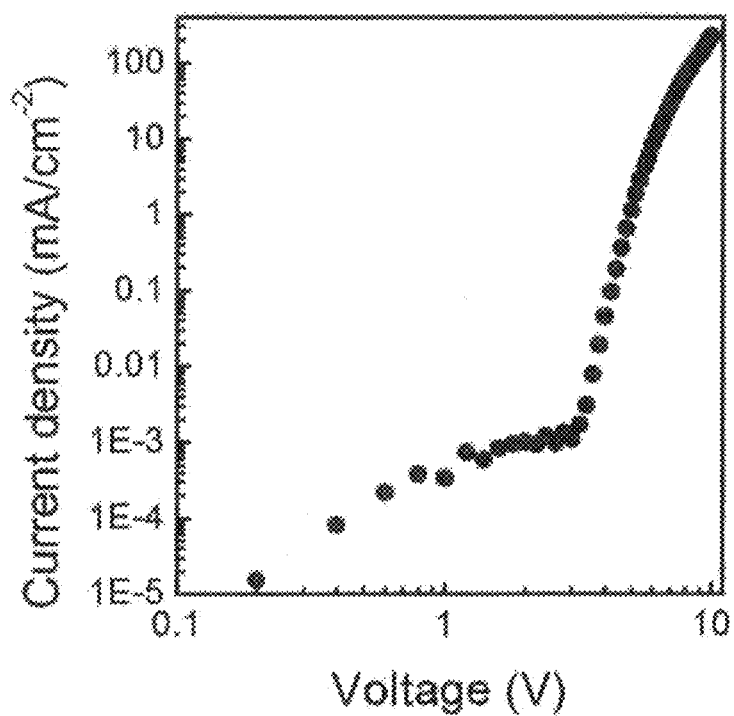
FIG. 4 is a graph showing the electric current density-voltage characteristics of the organic electroluminescent device using the compound 1 of Example 3.
Figure 5:
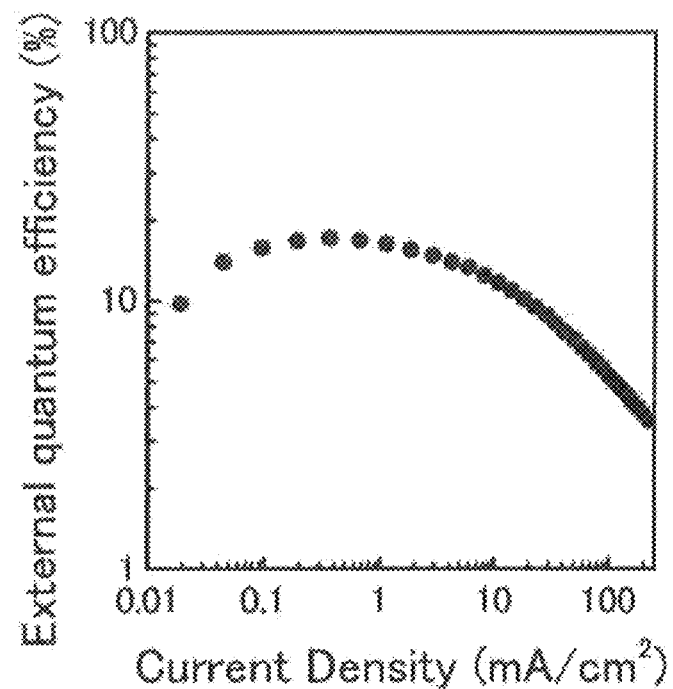
FIG. 5 is a graph showing the external quantum efficiency-electric current density characteristics of the organic electroluminescent device using the compound 1 of Example 3.

The organic electroluminescent device thus produced was measured with Semiconductor Parameter Analyzer (E5273A, produced by Agilent Technologies, Inc.), Optical Power Meter (1930C, produced by Newport Corporation) and Fiber Optic Spectrometer (USB2000, produced by Ocean Optics, Inc.), and thus light emission of a wavelength of 544 nm was observed. The electric current density-voltage (J-V) characteristics are shown in FIG. 4, and the electric current density-external quantum efficiency characteristics are shown in FIG. 5. The organic electroluminescent device using the compound 1 as a light emission material achieved a high external quantum efficiency of 17.06%.

Example 4

Figure 6:
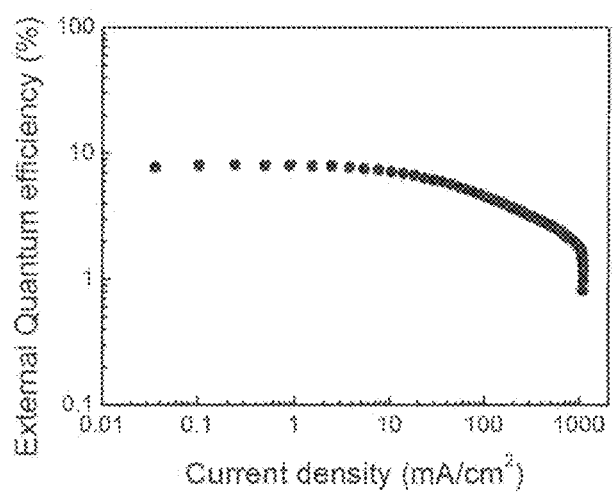
FIG. 6 is a graph showing the external quantum efficiency-electric current density characteristics of the organic electroluminescent device using the compound 6 of Example 4.

An organic photoluminescent device was produced by using the compound 6 instead of the compound 1 in Example 3 and subjected to the same test, and thus light emission of a wavelength of 553 nm was observed. The electric current density-external quantum efficiency characteristics are shown in FIG. 6.

Example 5

Figure 7:
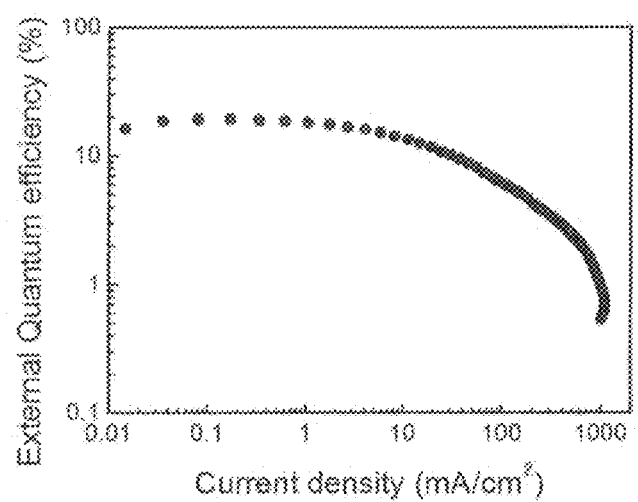
FIG. 7 is a graph showing the external quantum efficiency-electric current density characteristics of the organic electroluminescent device using the compound 301 of Example 5.

An organic photoluminescent device was produced by using the compound 301 instead of the compound 1 in Example 3 and subjected to the same test, and thus light emission of a wavelength of 513 nm was observed. The electric current density-external quantum efficiency characteristics are shown in FIG. 7. The organic electroluminescent device using the compound 301 as a light emission material achieved a high external quantum efficiency of 19.32%.

Example 6

Figure 8:
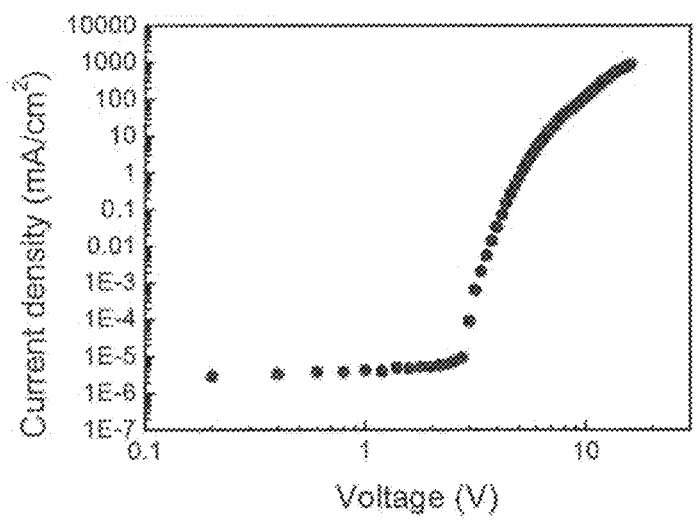
FIG. 8 is a graph showing the electric current density-voltage characteristics of the organic electroluminescent device using the compound 501 of Example 6.
Figure 9:
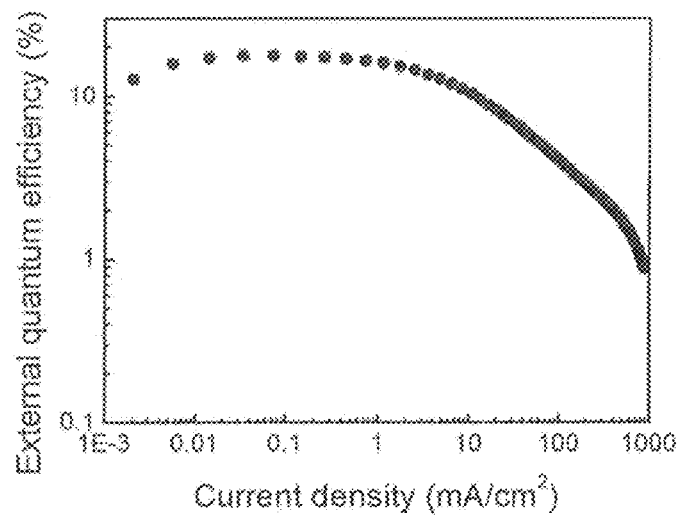
FIG. 9 is a graph showing the external quantum efficiency-electric current density characteristics of the organic electroluminescent device using the compound 503 of Example 6.

An organic photoluminescent device was produced by using the compound 501 instead of the compound 1 in Example 3 and subjected to the same test, and thus light emission of a wavelength of 530 nm was observed. The electric current density-voltage (J-V) characteristics are shown in FIG. 8, and the electric current density-external quantum efficiency characteristics are shown in FIG. 9. The organic electroluminescent device using the compound 501 as a light emission material achieved a high external quantum efficiency of 17.84%.

Example 7

In this example, an organic electroluminescent device having a light-emitting layer containing the compound 252 synthesized in Synthesis Example 9 as a light-emitting material was produced and evaluated for the characteristics thereof.

Thin films each were formed by a vacuum vapor deposition method at a vacuum degree of $5.0\times10^{-4}$ Pa on a glass substrate having formed thereon an anode formed of indium tin oxide (ITO) having a thickness of 100 nm. First, α-NPD was formed to a thickness of 35 nm on ITO. The compound 252 and CBP were then vapor-deposited from separate vapor deposition sources respectively to form a layer having a thickness of 15 nm, which was designated as a light-emitting layer. The concentration of the compound 252 herein was 6.0% by weight. TPBi was then formed to a thickness of 65 nm, lithium fluoride (LiF) was further vapor-deposited to a thickness of 0.8 nm, and then aluminum (Al) was vapor-deposited to a thickness of 80 nm, which was designated as a cathode, thereby completing an organic electroluminescent device.

Figure 10:
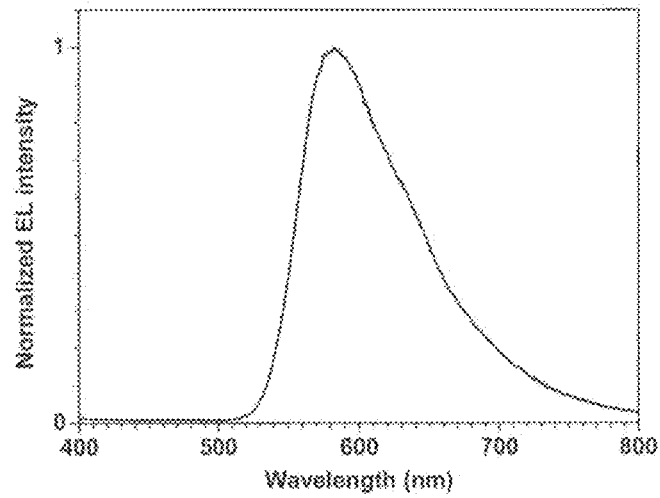
FIG. 10 is a light emission spectrum of the organic electroluminescent device using the compound 252 of Example 7.
Figure 11:
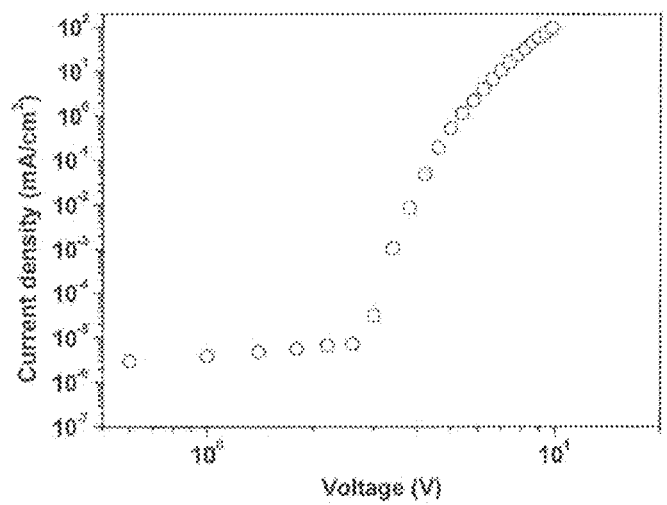
FIG. 11 is a graph showing the electric current density-voltage characteristics of the organic electroluminescent device using the compound 22 of Example 7.
Figure 12:
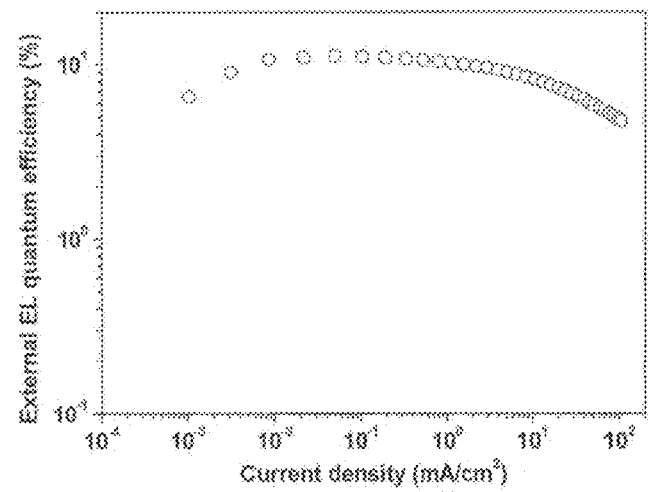
FIG. 12 is a graph showing the external quantum efficiency-electric current density characteristics of the organic electroluminescent device using the compound 252 of Example 7.

The organic electroluminescent device thus produced was measured with Semiconductor Parameter Analyzer (E5273A, produced by Agilent Technologies, Inc.), Optical Power Meter (1930C, produced by Newport Corporation) and Fiber Optic Spectrometer (USB2000, produced by Ocean Optics, Inc.), and thus the light emission spectrum shown in FIG. 10 was observed. The electric current density-voltage (J-V) characteristics are shown in FIG. 11, and the electric current density-external quantum efficiency characteristics are shown in FIG. 12.

Example 8

In this example, an organic electroluminescent device having a light-emitting layer containing the compound 523 synthesized in Synthesis Example 10 as a light-emitting material was produced and evaluated for the characteristics thereof.

Thin films each were formed by a vacuum vapor deposition method at a vacuum degree of $5.0 \times 10^{-4}$ Pa on a glass substrate having formed thereon an anode formed of indium tin oxide (ITO) having a thickness of 100 nm. First, α-NPD was formed to a thickness of 40 nm on ITO, and then mCP was formed to a thickness of 10 nm. The compound 523 and PPT were then vapor-deposited from separate vapor deposition sources respectively to form a layer having a thickness of 20 nm, which was designated as a light-emitting layer. The concentration of the compound 523 herein was 6.0% by weight. PPT was then formed to a thickness of 40 nm, lithium fluoride (LiF) was further vapor-deposited to a thickness of 0.8 nm, and then aluminum (Al) was vapor-deposited to a thickness of 80 nm, which was designated as a cathode, thereby completing an organic electroluminescent device.

Figure 13:
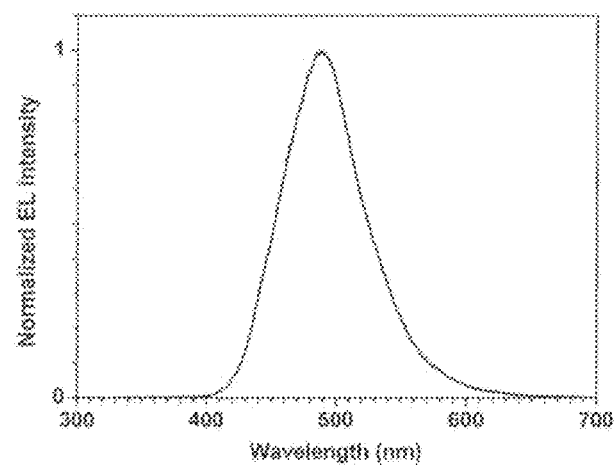
FIG. 13 is a light emission spectrum of the organic electroluminescent device using the compound 523 of Example 8.
Figure 14:
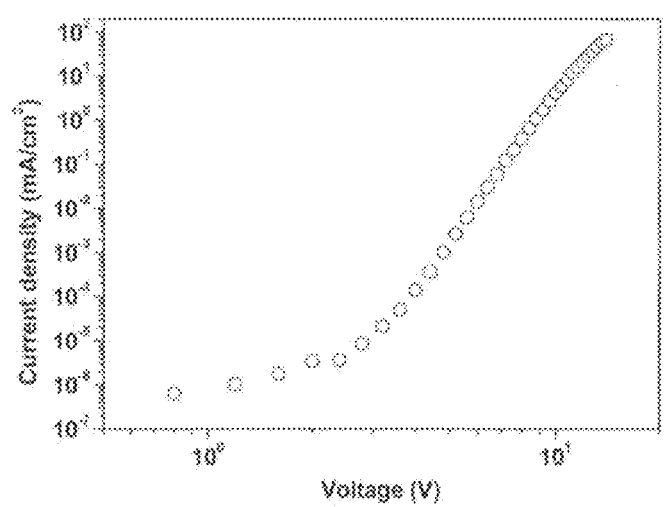
FIG. 14 is a graph showing the electric current density-voltage characteristics of the organic electroluminescent device using the compound 523 of Example 8.
Figure 15:
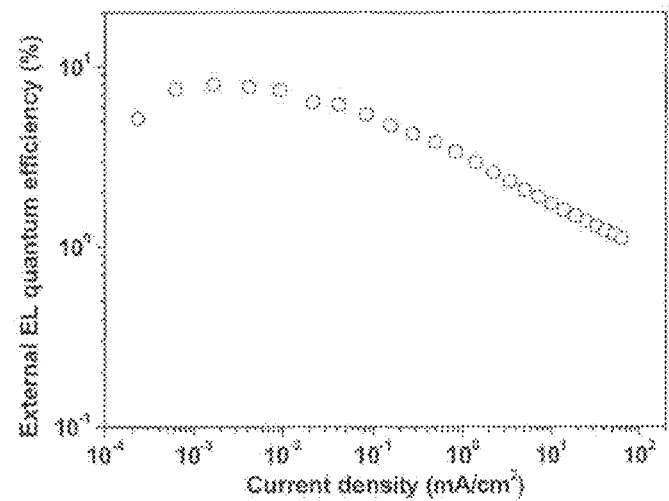
FIG. 15 is a graph showing the external quantum efficiency-electric current density characteristics of the organic electroluminescent device using the compound 523 of Example 8.

The organic electroluminescent device thus produced was measured with Semiconductor Parameter Analyzer (E5273A, produced by Agilent Technologies, Inc.), Optical Power Meter (1930C, produced by Newport Corporation) and Fiber Optic Spectrometer (USB2000, produced by Ocean Optics, Inc.), and thus the light emission spectrum shown in FIG. 13 was observed. The electric current density-voltage (J-V) characteristics are shown in FIG. 14, and the electric current density-external quantum efficiency characteristics are shown in FIG. 15.

Example 9

In this example, an organic electroluminescent device having a light-emitting layer containing the compound 31 synthesized in Synthesis Example 11 as a light-emitting material was produced and evaluated for the characteristics thereof.

Thin films each were formed by a vacuum vapor deposition method at a vacuum degree of $5.0 \times 10^{-4}$ Pa on a glass substrate having formed thereon an anode formed of indium tin oxide (ITO) having a thickness of 100 nm. First, α-NPD was formed to a thickness of 35 nm on ITO, and then mCP was formed to a thickness of 10 nm. The compound 31 and mCP were then vapor-deposited from separate vapor deposition sources respectively to form a layer having a thickness of 15 nm, which was designated as a light-emitting layer. The concentration of the compound 31 herein was 3.0% by weight. PPT was then formed to a thickness of 10 nm, TPBi was formed thereon to a thickness of 40 nm, lithium fluoride (LiF) was further vapor-deposited to a thickness of 0.8 nm, and then aluminum (Al) was vapor-deposited to a thickness of 100 nm, which was designated as a cathode, thereby completing an organic electroluminescent device.

Figure 16:
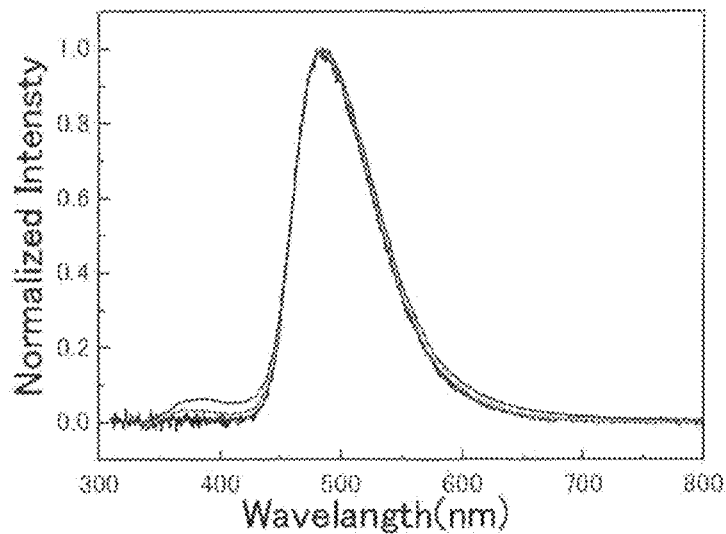
FIG. 16 is a light emission spectrum of the organic electroluminescent device using the compound 31 of Example 9.
Figure 17:
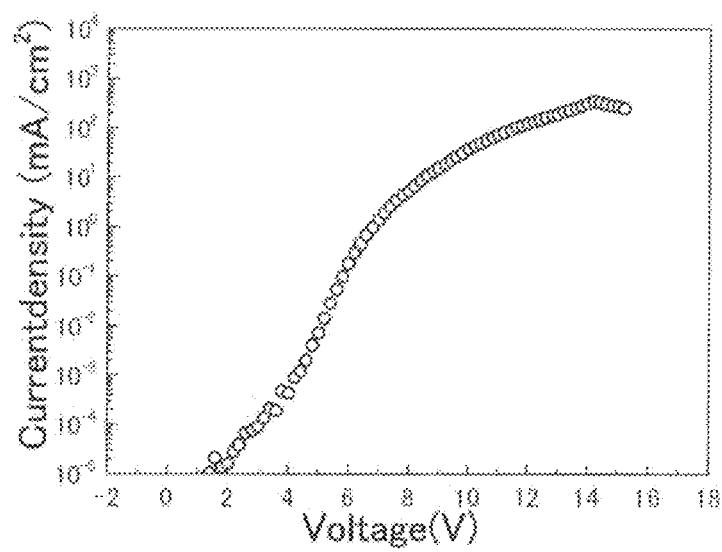
FIG. 17 is a graph showing the electric current density-voltage characteristics of the organic electroluminescent device using the compound 31 of Example 9.
Figure 18:
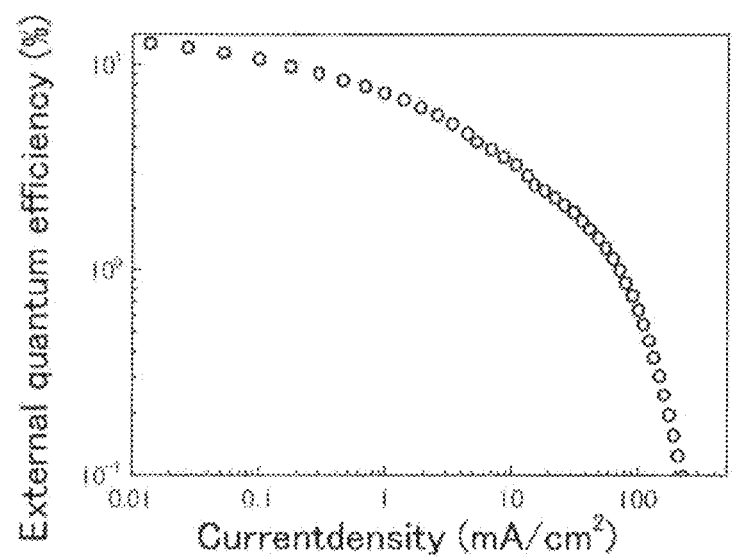
FIG. 18 is a graph showing the external quantum efficiency-electric current density characteristics of the organic electroluminescent device using the compound 31 of Example 9.

The organic electroluminescent device thus produced was measured with Semiconductor Parameter Analyzer (E5273A, produced by Agilent Technologies, Inc.), Optical Power Meter (1930C, produced by Newport Corporation) and Fiber Optic Spectrometer (USB2000, produced by Ocean Optics, Inc.), and thus the light emission spectrum shown in FIG. 16 was observed. The electric current density-voltage (J-V) characteristics are shown, in FIG. 17, and the electric current density-external quantum efficiency characteristics are shown in FIG. 18.

Example 10

In this example, organic electroluminescent devices having a light-emitting layer containing the compound 1 as a light-emitting material in various concentrations were produced and evaluated for the characteristics thereof.

Figure 19:
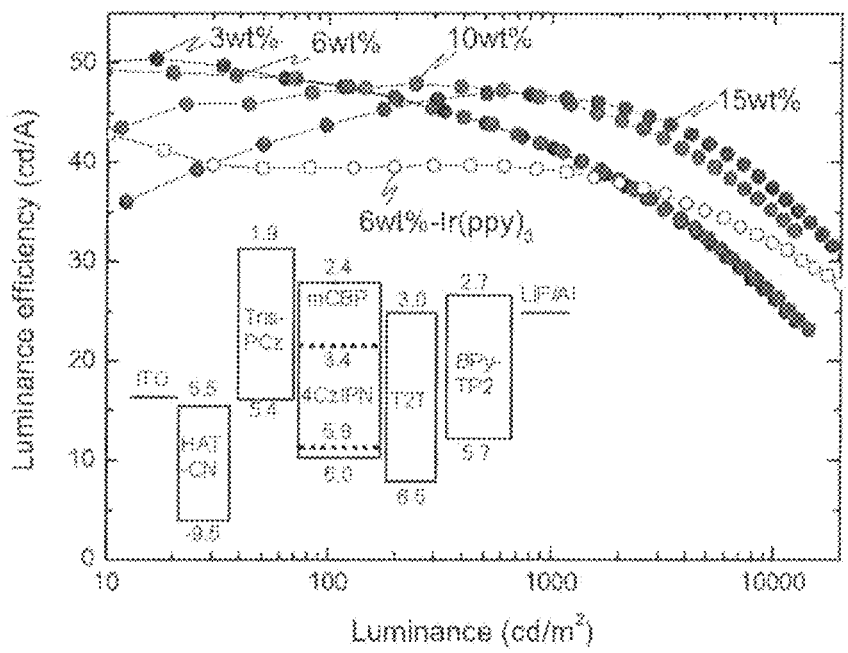
FIG. 19 is a graph showing the luminance efficiency-luminance characteristics of the organic electroluminescent device using the compound 301 of Example 10.
Figure 20:
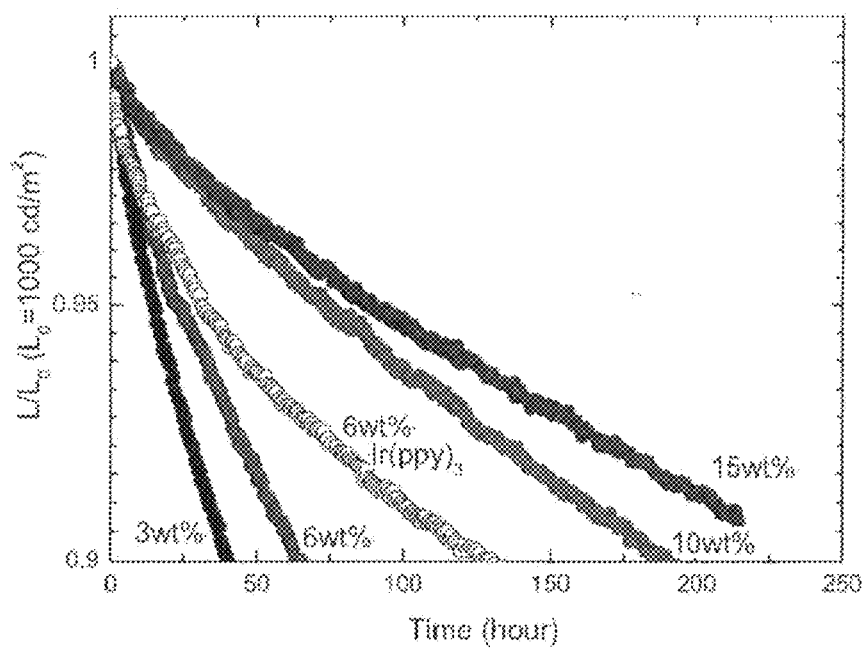
FIG. 20 is a graph showing the luminance deterioration characteristics of the organic electroluminescent device using the compound 301 of Example 10.

Thin films each were formed by a vacuum vapor deposition method at a vacuum degree of $5.0 \times 10^{-4}$ Pa on a glass substrate having formed thereon an anode formed of indium tin oxide (ITO) having a thickness of 100 nm. First, HAT-CN was formed to a thickness of 10 nm on ITO, and then Tris-PCz was formed to a thickness of 30 nm. The compound 1 and mCBP were then vapor-deposited from separate vapor deposition sources respectively to form a layer having a thickness of 30 nm, which was designated as a light-emitting layer. The concentration of the compound 1 herein was 3% by weight, 6% by weight, 10% by weight or 15% by weight. T2T was then formed to a thickness of 10 nm, BPy-TP2 was formed thereon to a thickness of 40 nm, lithium fluoride (LiF) was further vapor-deposited to a thickness of 0.8 nm, and then aluminum (Al) was vapor-deposited to a thickness of 100 nm, which was designated as a cathode, thereby completing an organic electroluminescent device. For comparison, an organic electroluminescent device, in which the compound 1 in the light-emitting layer was changed to 6% by weight of Ir(ppy)$_3$, was produced. The organic electroluminescent devices were measured with the same equipments as in Example 3. The luminance-light emission efficiency characteristics are shown in FIG. 19, and the luminance deterioration characteristics are shown in FIG. 20. The external quantum efficiency achieved was 17.0% for the case where the concentration of the compound 1 was 0.3% by weight, 15.6% for the case of 6% by weight, 14.2% for the case of 10% by weight, and 14.0% for the case of 15% by weight. In the case where the concentration of the compound 1 is 10% by weight, a high external quantum efficiency (13.8%) was achieved at 1,000 cd/m$^2$.

[Chem. 51]

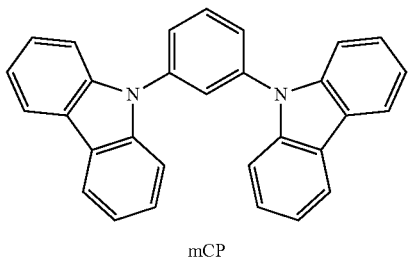

mCP

-continued

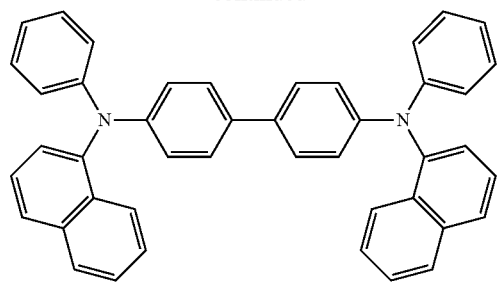

α-NPD

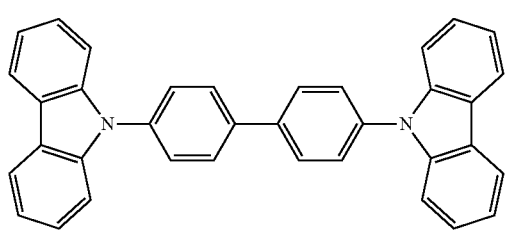

CBP

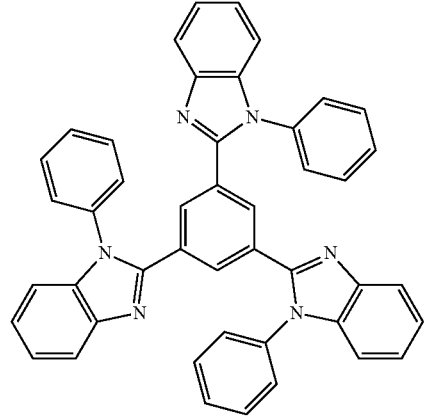

TPBi

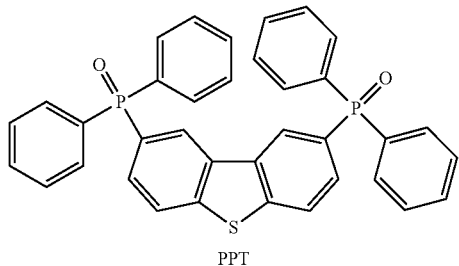

PPT

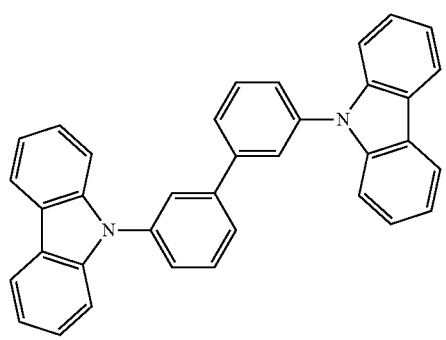

mCBP

-continued

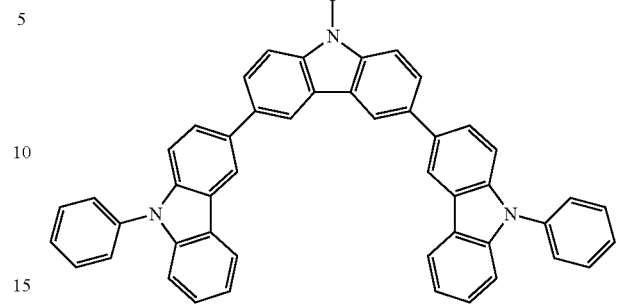

Tris-PCz

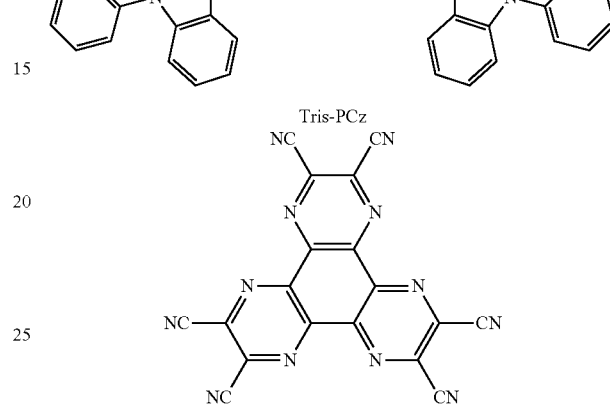

HAT-CN

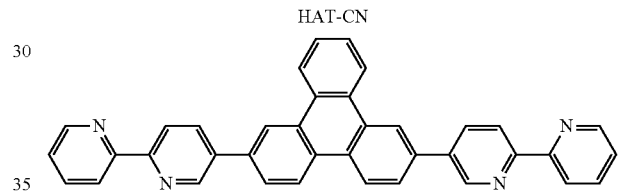

BPy-TP2

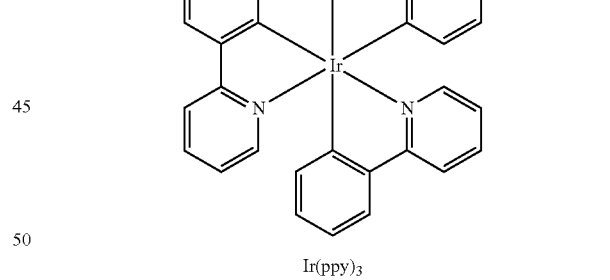

Ir(ppy)$_3$

INDUSTRIAL APPLICABILITY

The organic light-emitting device of the invention is capable of achieving a high light emmission efficiency. The compound of the invention is useful as a light-emitting material of the organic light-emitting device. Accordingly, the invention has high industrial applicability.

REFERENCE SIGNS LIST

1 substrate
2 anode
3 hole inject ion layer 4 hole transporting layer
5 light-emitting layer
6 electron transporting layer
7 cathode

The invention claimed is:
1. A method for emitting a light from a composition comprising a compound represented by the following formula (1), comprising irradiating the composition with a light or injecting carriers to the composition, provided that when the composition is a film comprising the compound, the film further comprises a host material;

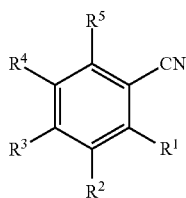

Formula (1)

wherein at least one of $R^1$ to $R^5$ represents a cyano group, at least one of $R^1$ to $R^5$ represents a group represented by the following formula (11), and the balance of $R^1$ to $R^5$ represents a hydrogen atom or a substituent;

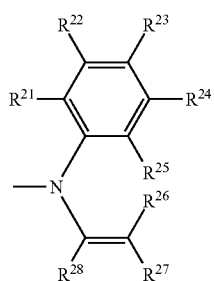

Formula (11)

wherein $R^{21}$ to $R^{28}$ each independently represent a hydrogen atom or a substituent, provided that at least one of the following requirements (A) and (B) is satisfied:
(A) $R^{25}$ and $R^{26}$ jointly form a single bond, and
(B) $R^{27}$ and $R^{28}$ jointly form an atomic group that is required for forming a substituted or unsubstituted benzene ring.

2. The method according to claim 1, wherein the composition is a solution of a compound represented by the formula (1).

3. The method according to claim 1, which emits a delayed fluorescent light from the solution of a compound represented by the formula (1).

4. The method according to claim 2, which comprises irradiating the solution with a light.

5. The method according to claim 1, wherein the composition is a film of a compound represented by the formula (1).

6. The method according to claim 5, which emits a delayed fluorescent light from the film of a compound represented by the formula (1).

7. The method according to claim 5, which comprises irradiating the film with a light.

8. The method according to claim 5, which comprises injecting carriers to the film.

9. The method according to claim 8, which comprises injecting carriers to the film from a cathode and an anode.

10. The method according to claim 1, wherein at least one of $R^1$ to $R^5$ in the formula (1) represents a substituted or unsubstituted 9-carbazolyl group, a substituted or unsubstituted 1,2,3,4-tetrahydro-9-carbazolyl group, a substituted or unsubstituted 1-indolyl group or a substituted or unsubstituted diarylamino group.

11. The method according to claim 1, wherein at least two of $R^1$ to $R^5$ in the formula (1) represent a substituted or unsubstituted 9-carbazolyl group, a substituted or unsubstituted 1,2,3,4-tetrahydro-9-carbazolyl group, a substituted or unsubstituted 1-indolyl group or a substituted or unsubstituted diarylamino group.

12. The method according to claim 1, wherein at least one of $R^1$ to $R^5$ in the formula (1) represents a cyano group, and the balance of $R^1$ to $R^5$ each independently represents any of a hydroxy group, a halogen atom, a substituted or unsubstituted 9-carbazolyl group, a substituted or unsubstituted 1,2,3,4-tetrahydro-9-carbazolyl group, a substituted or unsubstituted 1-indolyl group or a substituted or unsubstituted diarylamino group.

13. The method according to claim 1, wherein at least one of $R^1$ to $R^5$ in the formula (1) represents a cyano group, and the balance of $R^1$ to $R^5$ each independently represents any of a substituted or unsubstituted 9-carbazolyl group, a substituted or unsubstituted 1,2,3,4-tetrahydro-9-carbazolyl group, a substituted or unsubstituted 1-indolyl group or a substituted or unsubstituted diarylamino group.

14. The method according to claim 1, wherein at least one of $R^1$ to $R^5$ in the formula (1) represents a cyano group, and the balance of $R^1$ to $R^5$ each represents a substituted or unsubstituted 9-carbazolyl group.

15. The method according to claim 1, wherein at least one of $R^1$ to $R^5$ in the formula (1) represents a hydroxy group, at least one of $R^1$ to $R^5$ represents a cyano group, and the balance of $R^1$ to $R^5$ each represents a substituted or unsubstituted 9-carbazolyl group.

16. The method according to claim 1, wherein at least one of $R^1$ to $R^5$ in the formula (1) represents a group represented by any of the following formulae (12) to (15):

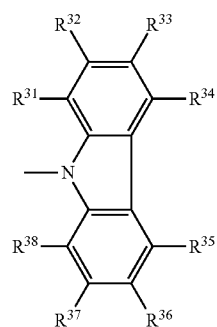

Formula (12)

wherein $R^{31}$ to $R^{38}$ each independently represent a hydrogen atom or a substituent;

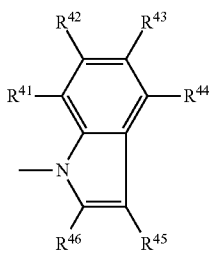

Formula (13)

wherein $R^{41}$ to $R^{46}$ each independently represent a hydrogen atom or a substituent;

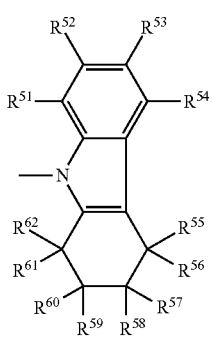

Formula (14)

wherein $R^{51}$ to $R^{62}$ each independently represent a hydrogen atom or a substituent;

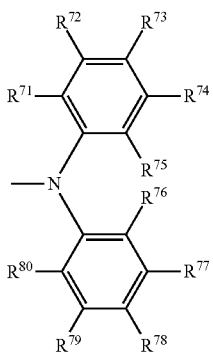

Formula (15)

wherein $R^{71}$ to $R^{80}$ each independently represent a hydrogen atom or a substituent.

17. The method according to claim 1, wherein the compound is represented by the following formula (2):

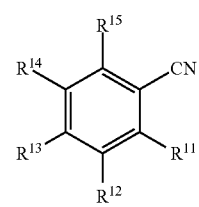

Formula (2)

wherein at least one of $R^{11}$, $R^{12}$, $R^{14}$ and $R^{15}$ represents a cyano group, at least three of $R^{11}$ to $R^{15}$ each represent a substituted or unsubstituted 9-carbazolyl group, a substituted or unsubstituted 1,2,3,4-tetrahydro-9-carbazolyl group, a substituted or unsubstituted 1-indolyl group or a substituted or unsubstituted diarylamino group, and the balance of $R^{11}$ to $R^{15}$ represents a hydroxy group.

18. The method according to claim 17, wherein $R^{12}$ in the formula (2) is not a cyano group when $R^{14}$ in the formula (2) is a cyano group.

19. The method according to claim 1, wherein the compound is represented by the following formula (3):

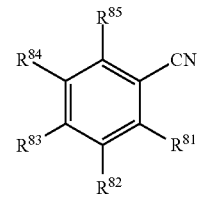

Formula (3)

wherein one of $R^{81}$ to $R^{85}$ represents a cyano group, two of $R^{81}$ to $R^{85}$ each represent a substituted or unsubstituted 9-carbazolyl group, and the other two thereof each represent a hydrogen atom.

* * * * *